(12) United States Patent
Issakani et al.

(10) Patent No.: US 7,022,493 B2
(45) Date of Patent: *Apr. 4, 2006

(54) UBIQUITIN CONJUGATION ASSAYS

(75) Inventors: Sarkiz D. Issakani, San Jose, CA (US);
Jianing Huang, Foster City, CA (US);
Julie Sheung, San Francisco, CA (US);
Todd R. Pray, San Francisco, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/835,096

(22) Filed: Apr. 28, 2004

(65) Prior Publication Data

US 2005/0032139 A1    Feb. 10, 2005

Related U.S. Application Data

(63) Continuation of application No. 09/826,312, filed on Apr. 3, 2001, now Pat. No. 6,737,244, which is a continuation-in-part of application No. 09/542,497, filed on Apr. 3, 2000, now Pat. No. 6,740,495.

(51) Int. Cl.
*G01N 33/543* (2006.01)

(52) U.S. Cl. .............. 435/7.92; 435/7.1; 435/7.4; 435/7.6; 435/7.9; 435/7.91; 435/7.93; 435/7.94; 435/7.95; 435/14; 435/21; 435/28; 436/546; 436/544; 436/164; 436/172; 436/805

(58) Field of Classification Search .............. 435/7.92, 435/7.1, 7.4, 7.6, 7.9, 7.91, 7.93, 7.94, 7.95, 435/14, 21, 28; 436/546, 544, 164, 172, 436/805
See application file for complete search history.

(56) References Cited

U.S. PATENT DOCUMENTS

| 5,726,025 A | 3/1998 | Kirschner et al. |
| 5,968,761 A | 10/1999 | Rolfe et al. |
| 6,737,244 B1 * | 5/2004 | Issakani et al. ............ 435/7.92 |
| 6,740,495 B1 * | 5/2004 | Issakani et al. ............ 435/7.92 |

FOREIGN PATENT DOCUMENTS

| CA | 2269099 | 5/1998 |
| EP | 0 587 279 | 3/1999 |
| EP | 1 033 401 | 9/2000 |
| WO | 98/21326 | 5/1998 |
| WO | 99/06553 | 2/1999 |
| WO | 99/06554 | 2/1999 |
| WO | 99/32514 | 7/1999 |
| WO | 99/34012 | 7/1999 |
| WO | 00/22110 | 4/2000 |
| WO | 00/50445 | 8/2000 |
| WO | 00/58472 | 10/2000 |

OTHER PUBLICATIONS

Tan, et al., "Recruitement of a ROC1-CUL1 Ubiquitin Ligase by Skp1 and HOS to Catalyze the Ubiquitination of IkBα," *Mol. Cell*, 3(4):527-533 (1999).

(Continued)

*Primary Examiner*—Long V. Le
*Assistant Examiner*—Pensee T. Do
(74) *Attorney, Agent, or Firm*—Townsend and Townsend and Crew LLP

(57) ABSTRACT

The invention relates to assays for measuring ubiquitin ligase activity and for identifying modulators of ubiquitin ligase enzymes.

20 Claims, 15 Drawing Sheets

OTHER PUBLICATIONS

Ohta, et al., "ROC1, a Homolog of APC11, Represents a Family of Cullin Partners with an Associated Ubiquitin Ligase Activity,", *Mol. Cell* 3(4):535-541(1999).

Hershko, A., "Roles of ubiquitin-mediated proteolysis in cell cycle control,", *Curr. Opin. Cell Biol*. 9:788-799 (1997).

Spencer, et al., "Signal-induced ubiquitination of IkBα by the F-box protein Slimb/β-TrCP," *Genes Dev*. 13:284-294 (1999).

Kamura et al., "Rbx1, a Component of the VHL Tumor Suppressor Complex and SCF Ubiquitin Ligase," *Science* 284:657-661 (1999).

Yu et al., "Identification of a cullin homology region in a subunit of the anaphase-promoting complex", *Science* 279: 1219-1222 (1998).

Duan et al., SAG, a novel zinc RING finger protein that protects cells from apoptosis induced by redox agents, *Mol. Cell. Biol*. 19:3145-3155 (1999).

Son et al., "Protein kinase CKII interacts with and phosphorylates the SAG protein containing ring-H2 finger motif", *Biochem. Biophys. Res. Comm*. 263:743-748 (1999).

Kipreous et al., "cul-1 is required for cell cycle exit in C. elegans and identifies a novel gene family," *Cell* 85:829-839 (1996).

* cited by examiner

FIGURE 8A

```
ATGTCCAGCTCGCCGCTGTCCAAGAAACGTCGCGTGTCCGGGCCTGATCCAAAGCCGGGTTCTAACTGCTCCCCTGCCCA
GTCCGTGTTGCCCCAAGTGCCCTCGGCGCCAACCAACGGAATGGCGAAGAACGGCAGTGAAGCAGACATCGATGAGGGCC
TTTACTCCCGGCAGCTGTATGTGTTGGGCCATGAGGCGATGAAGCGGCTCCAGACATCCAGCGTTCTGGTGTCAGGCCTG
CGGGGCCTGGGGGTAGAGATCGCGAAGAACATCATCCTTGGCGGGGTCAAGGCCGTGACCCTCCATGACCAGGGCACGGC
CCAGTGGGCTGACCTCTCCTCCCAGTTCTACCTGCGAGAGGAGGACATAGGGAAAAACCGCGCTGAGGTGTCACAGCCCC
GCCTTGCTGAACTCAATAGCTACGTGCCTGTCACCGCCTACACTGGGCCGCTGGTTGAGGACTTCCTCAGTGGCTTCCAG
GTGGTGGTCCTCACTAACAGCCCCTGGAGGACCAGCTGCGCGTGGGCGAGTTCTGTCATAGCCGTGGCATCAAGCTGGT
AGTGGCAGACACGAGAGGCTTGTTTGGGCAACTCTTCTGCGACTTTGGAGAGGAAATGATCCTCACAGATTCCAACGGGG
AGCAGCCCCTCAGCACCATGGTTTCTATGGTCACCAAGGACAACCCTGGTGTGGTTACCTGCCTGGATGAGGCCCGACAT
GGGTTTGAGAGTGGCGATTTTGTTTCCTTCTCCGAAGTACAGGGCATGACTGAGCTCAATGGAAACCAGCCCATAGAGAT
CAAAGTCCTGGGTCCTTACACCTTTAGCATCTGTGACACCTCCAACTTCTCCGATTACATCCGTGGAGGCATTGTCAGCC
AGGTCAAAGTACCTAAGAAGATAAGCTTTAAATCCTTGTCAGCCTCGCTGGCAGAGCCTGACTTTGTGATGACGGACTTC
GCCAAGTTTTCTCGCCCCGCTCAGCTTCACATTGGCTTCCAGGCCTTGCACAAGTTCTGTGCACAGCACAGCCGGCCACC
TAGACCCCGGAACGAGGAGGATGCAGCAGAGCTGGTGACCCTAGCACGCGCTGTGAACTCTAAAGCCTCGTCGGCAGTGC
AGCAAGATAGCCTGGATGAGGACCTCATCCGGAACCTGGCCTTTGTGGCAGCCGGGGACCTGGCGCCCATCAATGCCTTC
ATTGGGGGCCTGGCTGCCCAGGAAGTCATGAAGGCCTGCTCTGGGAAGTTTATGCCCATCATGCAGTGGCTGTACTTTGA
TGCCCTTGAGTGTCTCCCGGAGGACAAAGAATCCCTCACAGAGGACAAGTGCCTCCCGCGCCAGAACCGTTATGATGGGC
AGGTGGCTGTGTTTGGCTCAGACCTGCAAGAGAAGCTGGGCAGGCAGAAGTACTTCCTGGTGGGTGCAGGGGCTATTGGC
TGTGAGCTGCTCAAGAACTTTGCCATGATTGGGCTGGGCTGTGGTGAGAACGGAGAAATAATTGTCACAGACATGGACAC
CATTGAGAAATCTAATCTGAACCGACAGTTTCTATTCCGGCCCTGGGATGTCACGAAGTTAAAATCTGACACAGCTGCTG
CAGCTGTGCACCAGATGAATCCACATATCCGGGTGACAAGCCACCAGAACCGTGTGGGTCCTGACACTGAACGTATCTAC
GACGACGATTTCTTCCAAACTCTGGATGGCGTGGCCAACGCCTTAGACAACGTGGATGCCCGCATGTACATGGACCGCCG
CTGCCGTGTACTACCGGAAGCCGCTGCTCGAATCAGGCACCCTGGGCACCAAGGGCAACGTCCAGGTGGTGATCCCCTTCC
TGACAGAGTCCTACAGCTCCAGCCAAGACCCACCTGAGAAGTCCATCCCCATCTGTACCCTGAAGAACTTCCCCAACGCC
ATCGAACACACTCTTCAGTGGGCTCGGGATGAATTTGAAGGCCTCTTCAAGCAGCCAGCGGAAAATGTCAACCAGTACCT
CACAGACCCTAAGTTTGTGGAGCGGACATTGCGGCTGGCGGGTACCCAGCCACTGGAGGTGCTGGAGGCTGTGCAGCGCA
GCCTGGTGCTGCAGCTACCGCAGAGCTGGGCAGACTGTGTGACCTGGGCCTGCCACCACTGGCACACCCAGTATTCTAAC
AATATCCGGCAGCTGTTGCACAACTTCCCTCCCGACCAGCTCACAAGCTCGGGAGCTCCCTTCTGGTCTGGGCCCAAACG
TTGTCCTCACCCACTCACCTTTGATGTTAGCAACCCTCTGCATCTGGACTATGTGATGGCTGCTGCCAACCTGTTTGCCC
AGACCTACGGGCTGGCAGGCTCTCAGGACCGAGCTGCTGTGGCCACACTCCTGCAGTCTGTACAGGTCCCCGAGTTTACC
CCCAAGTCTGGCGTCAAAATCCACGTTTCTGACCAGGAGCTGCAGAGCGCCAATGCTTCTGTTGACGACAGCCGTTTAGA
GGAGCTCAAGGCTACGCTGCCTAGCCCCGACAAGCTCCCTGGATTCAAGATGTACCCCATTGACTTTGAGAAGGATGATG
ATAGTAACTTTCACATGGACTTCATTGTGGCCGCATCCAACCTCCGGGCCGAAAACTATGACATTCCCCCTGCAGACCGG
CACAAGAGCAAGCTGATTGCAGGGAAGATCATCCCAGCCATTGCCACGACCACAGCAGCTGTCGTTGGCCTTGTGTGTCT
GGAGCTGTACAAGGTAGTGCAGGGACACCGACACCTCGACTCCTACAAGAATGGTTTCCTCAACCTGGCCCTGCCGTTTT
TCGGTTTCTCTGAACCTCTGGCTGCACCACGTCACCAGTACTATAACCAAGAGTGGACATTGTGGGATCGCTTTGAGGTT
CAGGGACTGCAGCCCAACGGTGAGGAGATGACCCTCAAACAATTCCTCGACTACTTTAAGACAGAGCACAAATTGGAGAT
TACCATGCTGTCCCAGGGTGTGTCCATGCTCTATTCCTTCTTTATGCCAGCTGCGAAGCTCAAGGAACGGTTGGACCAGC
CGATGACAGAGATTGTAAGCCGTGTGTCGAAGCGAAAGCTGGGCCGCCACGTGCGGGCGCTGGTGCTTGAGCTGTGCTGC
AACGACGAGAGCGGCGAGGACGTCGAAGTCCCCTACGTCCGATATACCATCCGTTAA
```

FIGURE 8B

```
MSSSPLSKKRRVSGPDPKPGSNCSPAQSVLPQVPSAPTNGMAKNGSEADIDEGLYSRQLYVLGHEAMKRLQTSSVLVSGL
RGLGVEIAKNIILGGVKAVTLHDQGTAQWADLSSQFYLREEDIGKNRAEVSQPRLAELNSYVPVTAYTGPLVEDFLSGFQ
VVVLTNSPLEDQLRVGEFCHSRGIKLVVADTRGLFGQLFCDFGEEMILTDSNGEQPLSTMVSMVTKDNPGVVTCLDEARH
GFESGDFVSFSEVQGMTELNGNQPIEIKVLGPYTFSICDTSNFSDYIRGGIVSQVKVPKKISFKSLSASLAEPDFVMTDF
AKFSRPAQLHIGFQALHKFCAQHSRPPRPRNEEDAAELVTLARAVNSKASSAVQQDSLDEDLIRNLAFVAAGDLAPINAF
IGGLAAQEVMKACSGKFMPIMQWLYFDALECLPEDKESLTEDKCLPRQNRYDGQVAVFGSDLQEKLGRQKYFLVGAGAIG
CELLKNFAMIGLGCGENGEIIVTDMDTIEKSNLNRQFLFRPWDVTKLKSDTAAAAVHQMNPHIRVTSHQNRVGPDTERIY
DDDFFQTLDGVANALDNVDARMYMDRRCVYYRKPLLESGTLGTKGNVQVVIPFLTESYSSSQDPPEKSIPICTLKNFPNA
IEHTLQWARDEFEGLFKQPAENVNQYLTDPKFVERTLRLAGTQPLEVLEAVQRSLVLQLPQSWADCVTWACHHWHTQYSN
NIRQLLHNFPPDQLTSSGAPFWSGPKRCPHPLTFDVSNPLHLDYVMAAANLFAQTYGLAGSQDRAAVATLLQSVQVPEFT
PKSGVKIHVSDQELQSANASVDDSRLEELKATLPSPDKLPGFKMYPIDFEKDDDSNFHMDFIVAASNLRAENYDIPPADR
HKSKLIAGKIIPAIATTTAAVVGLVCLELYKVVQGHRHLDSYKNGFLNLALPFFGFSEPLAAPRHQYYNQEWTLWDRFEV
QGLQPNGEEMTLKQFLDYFKTEHKLEITMLSQGVSMLYSFFMPAAKLKERLDQPMTEIVSRVSKRKLGRHVRALVLELCC
NDESGEDVEVPYVRYTIRZ
```

FIGURE 9A

ATGGCGCTGAAACGGATTAATAAGGAACTTAGTGATTTGGCCCGTGACCCTCCAGCACAATGTTCTGCAGGTCCAGTTGG
GGATGATATGTTTCATTGGCAAGCCACAATTATGGGACCTAATGACAGCCCATATCAAGGCGGTGTATTCTTTTTGACAA
TTCATTTTCCTACAGACTACCCCTTCAAACCACCTAAGGTTGCATTTACAACAAGAATTTATCATCCAAATATTAACAGT
AATGGCAGCATTTGTCTCGATATTCTAAGATCACAGTGGTCGCCTGCTTTAACAATTTCTAAAGTTCTTTTATCCATTTG
TTCACTGCTATGTGATCCAAACCCAGATGACCCCCTAGTGCCAGAGATTGCACGGATCTATAAAACAGACAGAGATAAGT
ACAACAGAATATCTCGGGAATGGACTCAGAAGTATGCCATGTGA

FIGURE 9B

MALKRINKELSDLARDPPAQCSAGPVGDDMFHWQATIMGPNDSPYQGGVFFLTIHFPTDYPFKPPKVAFTTRIYHPNINS
NGSICLDILRSQWSPALTISKVLLSICSLLCDPNPDDPLVPEIARIYKTDRDKYNRISREWTQKYAMZ

FIGURE 10

MKVKIKCWNGVATWLWVANDENCGICRMAFNGCCPDCKVPGDDCPLVWGQCSHCFHMHCILKWLHAQQVQQHCPMCRQTW
KFKE

FIGURE 11

MAAAMDVDTPSGTNSGAGKKRFEVKKWNAVALWAWDIVVDNCAICRNHIMDLCIECQANQASATSEECTVAWGVCNHAFHF
HCISRWLKTRQVCPLDNREWEFQKYGH

FIGURE 12A

ATGGCCGACGTGGAAGACGGAGAGGAAACCTGCGCCCTGGCCTCTCACTCCGGGAGCTCAGGCTCAACGTCGGGAGGCGA
CAAGATGTTCTCCCTCAAGAAGTGGAACCcGGTGGCCATGTGGAGCTGGGACGTGGAGTGCGATACGTGCGCCATCTGCA
GGGTCCAGGTGATGGATGCCTGTCTTAGATGTCAAGCTGAAAACAAACAAGAGGACTGTGTTGTGGTCTGGGGAGAATGT
AATCATTCCTTCCACAACTGCTGCATGTCCCTGTGGGTGAAACAGAACAATCGCTGCCCTCTCTGCCAGCAGGACTGGGT
GGTCCAAAGAATCGGCAAATGA

FIGURE 12B

MADVEDGEETCALASHSGSSGSTSGGDKMFSLKKWNPVAMWSWDVECDTCAICRVQVMDACLRCQAENKQEDCVVVWGEC
NHSFHNCCMSLWVKQNNRCPLCQQDWVVQRIGK

FIGURE 13A

```
ATGGCGACGTCTAATCTGTTAAAGAATAAAGGTTCTCTTCAGTTTGAAGACAAATGGGATTTTATGCGCCCGATTGTTTT
GAAGCTTTTACGCCAGGAATCTGTTACAAAACAGCAGTGGTTTGATCTGTTTTCGGATGTGCATGCAGTCTGTCTTTGGG
ATGATAAAGGCCCAGCAAAAATTCATCAGGCTTTAAAAGAAGATATTCTTGAGTTTATTAAGCAGGCACAGGCACGAGTA
CTGAGCCATCAAGATGATACGGCTTTGCTAAAAGCATATATTGTTGAATGGCGAAAGTTCTTTACACAATGTGATATTTT
ACCAAAACCTTTTTGTCAACTAGAGATTACTTTAATGGGTAAACAGGGCAGCAATAAAAAATCAAATGTGGAAGACAGTA
TTGTTCGAAAGCTTATGCTTGATACATGGAATGAGTCAATCTTTTCAAACATAAAAAACAGACTCCAAGATAGTGCAATG
AAGCTGGTACATGCTGAGAGATTGGGAGAAGCTTTTGATTCTCAGCTGGTTATTGGAGTAAGAGAATCCTATGTTAACCT
TTGTTCTAATCCTGAGGATAAACTTCAAATTTATAGGGACAATTTTGAGAAGGCATACTTGGATTCAACAGAGAGATTTT
ATAGAACACAAGCACCCTCGTATTTACAACCAAATGGTGTACAGAATTATATGAAATATGCAGATGCTAAATTAAAAGAA
GAAGAAAAACGAGCACTACGTTATTTAGAAACAAGACGAGAATGTAACTCCGTTGAAGCACTCATGGAATGCTGTGTAAA
TGCCCTGGTGACATCATTTAAAGAGACTATCTTAGCTGAGTGCCAAGGCATGATCAAGAGAAATGAAACTGAAAAATTAC
ATTTAATGTTTTCATTGATGGACAAAGTTCCTAATGGTATAGAGCCAATGTTGAAAGACTTGGAGGAACATATCATTAGT
GCTGGCCTGGCAGATATGGTAGCAGCTGCTGAAACTATTACTACTGACTCTGAGAAATACGTTGAGCAGTTACTTACACT
ATTTAATAGATTTAGTAAACTCGTCAAAGAAGCTTTTCAAGATGATCCACGATTTCTTACTGCAAGAGATAAGGCGTATA
AAGCAGTTGTTAATGATGCTACCATATTTAAACTTGAATTACCTTTGAAGCAGAAGGGGGTGGGATTAAAAACTCAGCCT
GAATCAAAATGCCCTGAGCTGCTTGCCAATTACTGTGACATGTTGCTAAGAAAAACACCATTAAGCAAAAAACTAACCTC
TGAAGAGATTGAAGCAAAGCTTAAAGAAGTGCTCTTGGTACTTAAGTATGTACAGAACAAAGATGTTTTTATGAGGTATC
ATAAAGCTCATTTGACACGACGTCTTATATTAGACATCTCTGCCGATAGTGAAATTGAAGAAAACATGGTAGAGTGGCTA
AGAGAAGTTGGTATGCCAGCGGATTATGTAAACAAGCTTGCTAGAATGTTTCAGGACATAAAAGTATCTGAAGATTTGAA
CCAAGCTTTTAAGGAAATGCACAAAAATAATAAATTGGCATTACCAGCTGATTCAGTTAATATAAAAATTCTGAATGCTG
GCGCCTGGTCAAGAAGTTCTGAGAAAGTCTTTGTCTCACTTCCTACTGAACTGGAGGACTTGATACCGGAAGTAGAAGAA
TTCTACAAAAAAAATCATAGTGGTAGAAAATTACATTGGCATCATCTCATGTCAAATGGAATTATAACATTTAAGAATGA
AGTTGGTCAATATGATTTGGAGGTAACCACGTTTCAGCTCGCTGTATTGTTTGCATGGAACCAAAGACCCAGAGAGAAAA
TCAGCTTTGAAAATCTTAAGCTTGCAACTGAACTCCCTGATGCTGAACTTAGGAGGACTTTATGGTCTTTAGTAGCTTTC
CCAAAACTCAAACGGCAAGTTTTTTTGTATGACCCTCAAGTCAACTCACCCAAAGACTTTACAGAAGGTACCCTCTTCTC
AGTGAACCAGGAGTTCAGTTTAATAAAAAATGCAAAGGTTCAGAAAAGGGGTAAAATCAACTTGATTGGACGTTTGCAGC
TCACTACAGAAAGGATGAGAGAAGAAGAGAATGAAGGAATAGTTCAACTACGAATACTAAGAACCCAGGAAGCTATCATA
CAAATAATGAAAATGAGAAAGAAAATTAGTAATGCTCAGCTGCAGACTGAATTAGTAGAAATTTTGAAAAACATGTTCTT
GCCACAAAAGAAAATGATAAAAGAGCAAATAGAGTGGCTAATAGAGCACAAATACATCAGAAGAGATGAATCTGATATCA
ACACTTTCATATATATGGCATAA
```

FIGURE 13B

```
MRSFAWGSSGDHVGDKSEEAPGAWDEVSAVGALLQRPPHPGAGPTGPGPWWELRPPVKAWPGRERHEFSRRLVSRESKLK
NMATSNLLKNKGSLQFEDKWDFMRPIVLKLLRQESVTKQQWFDLFSDVHAVCLWDDKGPAKIHQALKEDILEFIKQAQAR
VLSHQDDTALLKAYIVEWRKFFTQCDILPKPFCQLEITLMGKQGSNKKSNVEDSIVRKLMLDTWNESIFSNIKNRLQDSA
MKLVHAERLGEAFDSQLVIGVRESYVNLCSNPEDKLQIYRDNFEKAYLDSTERFYRTQAPSYLQPNGVQNYMKYADAKLK
EEEKRALRYLETRRECNSVEALMECCVNALVTSFKETILAECQGMIKRNETEKLHLMFSLMDKVPNGIEPMLKDLEEHII
SAGLADMVAAAETITTDSEKYVEQLLTLFNRFSKLVKEAFQDDPRFLTARDKAYKAVVNDATIFKLELPLKQKGVGLKTQ
PESKCPELLANYCDMLLRKTPLSKKLTSEEIEAKLKEVLLVLKYVQNKDVFMRYHKAHLTRRLILDISADSEIEENMVEW
LREVGMPADYVNKLARMFQDIKVSEDLNQAFKEMHKNNKLALPADSVNIKILNAGAWSRSSEKVFVSLPTELEDLIPEVE
EFYKKNHSGRKLHWHHLMSNGIITFKNEVGQYDLEVTTFQLAVLFAWNQRPREKISFENLKLATELPDAELRRTLWSLVA
FPKLKRQVFLYDPQVNSPKDFTEGTLFSVNQEFSLIKNAKVQKRGKINLIGRLQLTTERMREEENEGIVQLRILRTQEAI
IQIMKMRKKISNAQLQTELVEILKNMFLPQKKMIKEQIEWLIEHKYIRRDESDINTFIYMA
```

FIGURE 14A

```
ATGGCGGCGGCAGTTGTGGTGGCGGAGGGGGACAGCGACTCCCGGCCCGGACAGGAGTTGTTAGTGGCCTGGAACACCGT
GAGCACCGGCCTGGTGCCGCCGGCTGCGCTGGGGCTGGTGTCTTCCCGGACCAGCGGTGCAGTCCCGCCAAAGGAAGAGG
AGCTCCGGGCGGCGGTGGAGGTTCTGAGGGGCCACGGGCTACACTCGGTCCTGGAGGAGTGGTTCGTGGAGGTGCTGCAG
AACGATCTGCAGGCCAACATCTCCCCTGAGTTCTGGAATGCCATCTCCCAATGCGAGAACTCTGCGGATGAGCCCCAGTG
CCTTTTGCTACTCCTTGACGCTTTTGGCCTGCTGGAGAGCCGCCTGGATCCCTACCTGCGTAGCCTAGAGCTGCTGGAGA
AATGGACTCGCCTGGGCTTGCTGATGGGCACTGGTGCTCAGGGGCTGCGAGAAGAAGTCCACACTATGTTGCGCGGAGTC
TTGTTCTTTA GCACCCCCAGAACCTTCCAAGAGATGATCCAGCGTCTGTATGGGTGCTTCTTGAGAGTCTATATGCAGAG
TAAGAGGAAGGGGGAAGGGGGCACAGACCCGGAACTGGAAGGGGAGCTGGACAGCCGGTATGCCCGTCGCCGGTACTACC
GGCTCCTGCAGAGCCCGCTGTGTGCAGGGTGCAGCAGTGACAAGCAACAGTGCTGGTGTCGCCAGGCTCTGGAGCAGTTC
CATCAGCTCAGCCAGGTCTTACACAGGCTCAGTCTGCTGGAGCGGGTCAGTGCCGAGGCTGTGACCACCACCCTGCACCA
GGTGACCCGGGAGAGGATGGAGGACCGTTGCCGGGGCGAGTACGAGCGCTCCTTCCTGCGTGAGTTCCACAAGTGGATCG
AGCGGGTGGTCGGCTGGCTCGGCAAGGTGTTCCTGCAGGACGGCCCCGCCAGGCCCGCATCTCCCGAGGCCGGCAACACC
CTGCGCCGCTGGCGCTGCCACGTGCAAAGGTTCTTCTACCGCATCTACGCCAGCCTGCGCATCGAGGAGCTCTTCAGCAT
CGTCCGAGACTTCCCAGACTCCCGGCCAGCCATCGAGGACCTCAAGTACTGCCTGGAGAGGACGGACCAGAGGCAGCAGC
TGCTCGTGTCCCTCAAGGCTGCCCTGGAGACTCGGCTCCTGCATCCAGGCGTCAACACGTGTGACATCATCACCCTCTAT
ATCTCTGCCATCAAGGCGCTGCGCGTGCTGGACCCTTCCATGGTCATCCTGGAGGTGGCCTGTGAGCCTATCCGCCGCTA
CCTGAGGACGCGGGAGGACACAGTGCGGCAGATTGTGGCTGGGCTGACGGGGGACTCGGACGGGACAGGGGACCTGGCTG
TTGAGCTGTCCAAGACCGACCCGGCGAGCCTGGAGACAGGCCAGGACAGTGAGGATGACTCAGGCGAGCCAGAGGACTGG
GTCCCGGACCCTGTGGATGCCGATCCAGGGAAGTCGAGCTCCAAGCGGCGTTCATCGGACATCATCAGCCTGCTGGTCAG
CATCTACGGCAGCAAGGACCTCTTCATCAATGAGTACCGCTCGCTGCTGGCCGACCGCCTGCTGCACCAGTTCAGCTTCA
GCCCCGAGCGGGAGATCCGCAACGTGGAGCTGCTGAAGCTGCCGTTTGGCGAGGCCCCAATGCACTTCTGTGAAGTCATG
CTGAAGGACATGGCGGACTCCCGCCGCATCAATGCCAACATCCGGGAGGAGGATGAGAAGCGGCCAGCAGAGGAGCAGCC
ACCGTTCGGGGTCTACGCTGTCATCCTGTCCAGTGAGTTCTGGCCGCCCTTCAAGGACGAGAAGCTGGAGGTCCCCGAGG
ATATCAGGGCAGCCCTGGAGGCTTACTGCAAGAAGTATGAGCAGCTCAAGGCCATGCGGACCCTCAGTTGGAAGCACACC
CTGGGCCTGGTGACCATGGACGTGGAGCTGGCCGACCGCACGCTGTCTGTGGCGGTCACCCCAGTACAGGCGGTGATCTT
GCTGTATTTTCAGGACCAAGCCAGCTGGACCTTGGAGGAACTGAGCAAGGCGGTGAAAATGCCCGTGGCGCTGCTGCGGC
GGCGGATGTCCGTGTGGCTGCAGCAGGGTGTGCTGCGTGAGGAGCCCCCGGCACCTTCTCTGTCATTGAGGAGGAGCGG
CCTCAGGACCGGGACAACATGGTGCTCATTGACAGTGACGACGAGAGCGACTCCGGCATGGCCTCCCAGGCCGACCAGAA
GGAGGAGGAGCTGCTGCTCTTCTGGACGTACATCCAGGCCATGCTGACCAACCTGGAGAGCCTCTCACTGGATCGTATCT
ACAACATGCTCCGCATGTTTGTGGTGACTGGGCCTGCACTGGCCGAGATTGACCTGCAGGAGCTGCAGGGCTACCTGCAG
AAGAAGGTGCGGGACCAGCAGCTCGTCTACTCGGCCGGCGTCTACCGCCTGCCCAAGAACTGCAGCTGA
```

FIGURE 14B

```
MAAAVVVAEGDSDSRPGQELLVAWNTVSTGLVPPAALGLVSSRTSGAVPPKEEELRAAVEVLRGHGLHSVLEEWFVEVLQ
NDLQANISPEFWNAISQCENSADEPQCLLLLLDAFGLLESRLDPYLRSLELLEKWTRLGLLMGTGAQGLREEVHTMLRGV
LFFSTPRTFQEMIQRLYGCFLRVYMQSKRKGEGGTDPELEGELDSRYARRRYYRLLQSPLCAGCSSDKQQCWCRQALEQF
HQLSQVLHRLSLLERVSAEAVTTTLHQVTRERMEDRCRGEYERSFLREFHKWIERVVGWLGKVFLQDGPARPASPEAGNT
LRRWRCHVQRFFYRIYASLRIEELFSIVRDFPDSRPAIEDLKYCLERTDQRQQLLVSLKAALETRLLHPGVNTCDIITLY
ISAIKALRVLDPSMVILEVACEPIRRYLRTREDTVRQIVAGLTGDSDGTGDLAVELSKTDPASLETGQDSEDDSGEPEDW
VPDPVDADPGKSSSKRRSSDIISLLVSIYGSKDLFINEYRSLLADRLLHQFSFSPEREIRNVELLKLRFGEAPMHFCEVM
LKDMADSRRINANIREEDEKRPAEEQPPFGVYAVILSSEFWPPFKDEKLEVPEDIRAALEAYCKKYEQLKAMRTLSWKHT
LGLVTMDVELADRTLSVAVTPVQAVILLYFQDQASWTLEELSKAVKMPVALLRRRMSVWLQQGVLREEPPGTFSVIEEER
PQDRDNMVLIDSDDESDSGMASQADQKEEELLLFWTYIQAMLTNLESLSLDRIYNMLRMFVVTGPALAEIDLQELQGYLQ
KKVRDQQLVYSAGVYRLPKNCS
```

FIGURE 15A

MQIFVKTLTGKTITLEVEPSDTIENVKAKIQDKEGIPPDQQRLIFAGKQLEDGRTLSDYNIQKESTLHLVLRLRGG

FIGURE 15B

MDYKDDDDKQIFVKTLTGKTITLEVEPSDTIENVKAKIQDKEGIPPDQQRLIFAGKQLEDGRTLSDYNIQKESTLHLVLRLRGG

FIGURE 15C

MDYKDDDDKCQIFVKTLTGKTITLEVEPSDTIENVKAKIQDKEGIPPDQQRLIFAGKQLEDGRTLSDYNIQKESTLHLVLRLRGG

UBIQUITIN CONJUGATION ASSAYS

This application is a continuation of application Ser. No. 09/826,312, filed Apr. 3, 2001 now U.S. Pat. No. 6,737,244, which is a continuation-in part of application Ser. No. 09/542,497, filed on Apr. 3, 2000 now U.S. Pat. No. 6,740,495; both of which are herein incorporated by reference for all purposes.

FIELD OF THE INVENTION

This invention is directed to assays for measuring the activity of ubitquitination enzymes. The invention is also directed to assays for identifying modulators of ubiquitination.

BACKGROUND OF THE INVENTION

Ubiquitin is a highly conserved 76 amino acid protein expressed in all eukaryotic cells. The levels of many intracellular proteins are regulated by a ubiquitin-dependent proteolytic process. This process involves the covalent ligation of ubiquitin to a target protein, resulting in a polyubiquitinated target protein which is rapidly detected and degraded by the 26S proteasome.

The ubiquitination of these proteins is mediated by a cascade of enzymatic activity. Ubiquitin is first activated in an ATP-dependent manner by a ubiquitin activating enzyme (E1). The C-terminus of a ubiquitin forms a high energy thiolester bond with E1. The ubiquitin is then passed to a ubiquitin conjugating enzyme (E2; also called ubiquitin carrier protein), also linked to this second enzyme via a thiolester bond. The ubiquitin is finally linked to its target protein to form a terminal isopeptide bond under the guidance of a ubiquitin ligase (E3). In this process, chains of ubiquitin are formed on the target protein, each covalently ligated to the next through the activity of E3.

The components of the ubiquitin ligation cascade have received considerable attention (for a review, see Weissman, *Nature Reviews* 2:169–178 (2001)). E1 and E2 are structurally related and well characterized enzymes. There are several species of E2 (at least 25 in mammals), some of which act in preferred pairs with specific E3 enzymes to confer specificity for different target proteins. While the nomenclature for E2 is not standardized across species, investigators in the field have addressed this issue and the skilled artisan can readily identify various E2 proteins, as well as species homologues (See Haas and Siepmann, *FASEB J.* 11:1257–1268 (1997)).

E3 enzymes contain two separate activities: a ubiquitin ligase activity to conjugate ubiquitin to substrates and form polyubiquitin chains via isopeptide bonds, and a targeting activity to physically bring the ligase and substrate together. Substrate specificity of different E3 enzymes is the major determinant in the selectivity of the ubiquitin-dependent protein degradation process.

Some E3 ubiquitin ligases are known to have a single subunit responsible for the ligase activity. Such E3 ligases that have been characterized include the HECT (homologous to E6-AP carboxy terminus) domain proteins, represented by the mammalian E6AP-E6 complex which functions as a ubiquitin ligase for the tumor suppressor p53 and which is activated by papillomavirus in cervical cancer (Huang et al., *Science* 286:1321–26 (1999)). Single subunit ubiquitin ligases having a RING domain include Mdm2, which has also been shown to act as a ubiquitin ligase for p53, as well as Mdm2 itself. Other RING domain, single subunit E3 ligases include: TRAF6, involved in IKK activation; Cbl, which targets insulin and EGF; Sina/Siah, which targets DCC; Itchy, which is involved in haematopoesis (B, T and mast cells); and IAP, involved with inhibitors of apoptosis.

The best characterized E3 ligase is the APC (anaphase promoting complex), which is a multi-subunit complex that is required for both entry into anaphase as well as exit from mitosis (see King et al., *Science* 274:1652–59 (1996) for review). The APC plays a crucial role in regulating the passage of cells through anaphase by promoting ubiquitin-dependent proteolysis of many proteins. In addition to degrading the mitotic B-type cyclin for inactivation of CDC2 kinase activity, the APC is also required for degradation of other proteins for sister chromatid separation and spindle disassambly. Most proteins known to be degraded by the APC contain a conserved nine amino acid motif known as the "destruction box" that targets them for ubiquitination and subsequent degradation. However, proteins that are degraded during G1, including G1 cyclins, CDK inhibitors, transcription factors and signaling intermediates, do not contain this conserved amino acid motif. Instead substrate phosphorylation appears to play an important role in targeting their interaction with an E3 ligase for ubiquitination (see Hershko et al., *Ann. Rev. Biochem.* 67:429–75 (1998)).

In eukaryotes, a family of complexes with E3 ligase activity play an important role in regulating G1 progression. These complexes, called SCF's, consist of at least three subunits, SKP1, Cullins (having at least seven family members) and an F-box protein (of which hundreds of species are known) which bind directly to and recruit the substrate to the E3 complex. The combinatorial interactions between the SCF's and a recently discovered family of RING finger proteins, the ROC/APC 11 proteins, have been shown to be the key elements conferring ligase activity to E3 protein complexes. Particular ROC/Cullin combinations can regulate specific cellular pathways, as exemplified by the function of APC11-APC2, involved in the proteolytic control of sister chromatid separation and exit from telophase into G1 in mitosis (see King et al., supra; Koepp et al., *Cell* 97:431–34 (1999)), and ROC1-Cullin 1, involved in the proteolytic degradation of $I_\kappa B_\alpha$ in NF-$_\kappa$-B/$I_\kappa$B mediated transcription regulation (Tan et al., *Mol. Cell* 3(4):527–533 (1999); Laney et al., *Cell* 97:427–30 (1999)).

Because the E3 complex is the major determinant of selection for protein degradation by the ubiquitin-dependent proteolytic process, modulators of E3 ligase activity may be used to upregulate or downregulate specific molecules involved in cellular signal transduction. Disease processes can be treated by such up- or down regulation of signal transducers to enhance or dampen specific cellular responses. This principle has been used in the design of a number of therapeutics, including Phosphodiesterase inhibitors for airway disease and vascular insufficiency, Kinase inhibitors for malignant transformation and Proteasome inhibitors for inflammatory conditions such as arthritis.

Due to the importance of ubiquitination in cellular regulation and the wide array of different possible components in ubiquitin-dependent proteolysis, there is a need for a fast and simple means for assaying E3 ligase activity. Furthermore, such an assay would be very useful for the identification of modulators of E3 ligase. Accordingly, it is an object of the present invention to provide methods of assaying ubiquitin ligase activity, which methods may further be used to identify modulators of ubiquitin ligase activity.

DESCRIPTION OF THE RELATED ART

Tan et al., supra, disclose that ROC1/Cul 1 catalyzes ubiquitin polymerization in the absence of target protein substrate. Ohta et al., Mol. Cell 3(4):535–541 (1999) disclose that APC11/APC2 also catalyze ubiquitin polymerization in the absence of target protein substrate, and that this activity is dependent on the inclusion of the proper E2 species. Rolfe et al., U.S. Pat. No. 5,968,761 disclose an assay for identifying inhibitors of ubiquitination of a target regulatory protein.

SUMMARY OF THE INVENTION

The present invention provides methods for assaying ubiquitin ligase activity and screening for agents which modulate ubiquitin ligase activity. In one aspect, a method of assaying ubiquitin ligase activity is provided involving the steps of combining ubiquitin, E1, E2 and E3 and measuring the amount of ubiquitin bound to E3. This method may further involve combining a candidate ubiquitin ligase modulator in the combining step. This method does not require a specific target protein to be ubiquitinated. In a preferred embodiment, a substrate protein for ubiquitination other than ubiquitin itself is specifically excluded.

In one embodiment of the assay described above, ubiquitin is in the form of tag1-ubiquitin. In another embodiment, E3 is in the form of tag2-E3. In these embodiments tag1 may be a label or a partner of a binding pair. In one embodiment, tag1 is a fluorescent label, in which case measuring the amount of ubiquitin bound to E3 may be by measuring luminescence.

In another embodiment, tag1 is a member of a binding pair chosen from the group antigen, biotin and CBP. In this latter embodiment, the partner of a binding pair may be labeled by indirect labeling, which may be by a fluorescent label or a label enzyme. The label enzyme may be horseradish peroxidase, alkaline phosphatase or glucose oxidase. When the indirect labeling is by a fluorescent label, measuring the amount of ubiquitin bound to E3 may be by measuring luminescence. In the case that the indirect labeling is by a label enzyme, said enzyme may be reacted with a substrate which produces a fluorescent product, in which case, measuring the amount of ubiquitin bound to E3 may be by measuring luminescence. In one embodiment of the method above, tag1 is a FLAG antigen. In this embodiment, indirect labeling may be by anti-FLAG.

In one aspect of the above method, tag2 is a surface binding molecule, which may be His-tag. In this latter case, the assaying may be performed in a multi-well plate comprising a surface substrate comprising nickel.

In a different embodiment of the method above, when tag1 is a fluorescent label, the combining step further includes combining tag3-ubiquitin. Tag3 may be the second member of a FRET pair with tag1 or it may be a quencher of tag1. In this embodiment, measuring the amount of ubiquitin bound to E3 may be by measuring fluorescent emission, which may involve measuring the fluorescent emission spectrum. In this last embodiment, the method may further comprise comparing the measured fluorescent emission spectrum with the fluorescent emission spectrum of unbound tag1- and tag3-ubiquitin. When measuring the amount of ubiquitin bound to E3 is by measuring the fluorescent emission spectrum, this measuring may be continuous or at specific time points following the original combining of materials.

In another aspect of the invention, a method of identifying modulators of ubiquitination enzymes is provided. This method involves combining tag1-ubiquitin, a candidate modulator, E1, E2 and tag2-E3 and measuring the amount of tag1-ubiquitin bound to tag2-E3. In another embodiment, this method further comprises combining tag1-ubiquitin, a candidate modulator, E1 and tag2-E2 and measuring the amount of tag1-ubiquitin bound to the tag2-E2. In a preferred embodiment, target protein (i.e., a substrate protein other than ubiquitin itself) is specifically excluded in the method.

In the embodiments of the method of identifying modulators of ubiquitination enzymes, tag1 may be a label or a partner of a binding pair. If tag1 is a label, it may be a fluorescent label, in which case, measuring the amount of bound tag1-ubiquitin may be by measuring luminescence. If tag1 is a partner of a binding pair, the potential binding pair partners, labeling options and subsequent measuring options are substantially as described for tag1 above for the method of assaying ubiquitin ligase activity.

In the above method of identifying modulators of ubiquitination enzymes, tag2 and tag3 may be surface substrate binding molecules. Options for such molecules and conditions for performing the method are as described for the method of assaying ubiquitin ligase activity.

In another aspect of the invention, a method of assaying ubiquitination enzyme activity is provided. This method comprises combining tag1-ubiquitin and tag2-ubiquitin, E1, E2 and E3 under conditions in which ubiquitination can take place and measuring the amount or rate of ubiquitination. In this embodiment, tag1 and tag2 constitute a FRET pair or tag1 is a fluorescent label and tag2 is a quencher of tag1. In one embodiment, the method includes combining a candidate ubiquitination modulator with the other components. In a preferred embodiment of this method, measuring is by measuring the fluorescent emission spectrum from the combination, preferably continuously or at specific time points following combining the components. These measurements may be compared to the fluorescent emission spectrum of unbound tag1 and tag2 ubiquitin.

Also provided herein is a method of identifying a ubiquitination modulator. This method involved combining a candidate ubiquitination modulator, tag1-ubiquitin and tag2-ubiquitin, E1, E2 and E3 under conditions in which ubiquitination can take place and measuring the amount or rate of ubiquitination. In this embodiment, tag1 and tag2 constitute a FRET pair or tag1 is a fluorescent label and tag2 is a quencher of tag1. In one embodiment, the method includes combining a candidate ubiquitination modulator with the other components. In a preferred embodiment of this method, measuring is by measuring the fluorescent emission spectrum from the combination, preferably continuously or at specific time points following combining the components. These measurements may be compared to the fluorescent emission spectrum of unbound tag1 and tag2 ubiquitin.

In the latter two assays described, the ubiquitin may be in the form tag1,3-ubiquitin and tag2,3-ubiquitin, wherein tag3 is a member of a binding pair, preferably FLAG. In another embodiment of these assays, E3 may be in the form of tag4-E3, wherein tag4 is a surface substrate bonding molecule.

In still another aspect of the invention, compositions are provided for use in assaying ubiquitination. The composition comprises tag1-ubiquitin and tag2-ubiquitin, wherein tag1 and tag2 constitute a FRET pair or tag1 is a fluorescent label and tag2 is a quencher of tag1. In one embodiment, the composition further comprises E1, E2 and E3. In a preferred embodiment, the composition further comprises a candidate ubiquitination modulator. In yet another embodiment, the composition comprises a target protein.

In addition, provided herein are compositions for use in assaying for a ubiquitination modulator. The composition comprises a candidate ubiquitination modulator, tag1-ubiquitin and tag2-ubiquitin, wherein tag1 and tag2 constitute a FRET pair or tag1 is a fluorescent label and tag2 is a quencher of tag1. In one embodiment, the composition further comprises E1, E2 and E3. In one embodiment, the composition comprises a target protein.

In preferred embodiments of the assays and compositions described above, E2 is selected from the group consisting of Ubc5, Ubc3, Ubc4 and UbcX. In ap referred embodiment, E3 comprises a RING finger protein, preferably selected from the group consisting of ROC1, ROC2 and APC11. In a preferred embodiment, E3 comprises a Cullin, preferably selected from the group consisting of CUL1, CUL2, CUL3, CUL4A, CUL4B, CUL5 and APC2. In a preferred embodiment, E3 comprises a RING finger protein/Cullin combination, preferably selected from the group consisting of APC11/APC2, ROC1/CUL1, ROC1/CUL2 and ROC2/CUL5.

Other aspects of the invention will become apparent to the skilled artisan from the following description of the invention.

BRIEF DESCRIPTION OF THE DRAWINGS

FIG. 3 shows relative ubiquitin ligase activity in an assay combining ubiquitin, E1, E2 and E3.

FIG. 5 shows the concentration-dependent effect of two ubiquitin ligase activity modulators in assays measuring ubiquitin ligase activity with two different E3 enzymes.

FIG. 6 shows the proportions of ubiquitin ligase activity and ubiquitin conjugating activity in the presence and absence of two candidate ubiquitin ligase enzyme modulators for combinations of E1, E2 and E3 and combinations of enzymes E1 and E2.

FIG. 7 shows the concentration-dependent effects of two candidate ubiquitin ligase modulators on ubiquitin ligase activity and ubiquitin conjugating activity.

FIGS. 8A and 8B show the nucleic acid sequence encoding rabbit E1 and the amino acid sequence of rabbit E1, respectively.

FIGS. 9A and 9B show the nucleic acid sequence encoding the E2 Ubc5c and the amino acid sequence of the E2 Ubc5c, respectively.

FIG. 10 shows the amino acid sequence of the RING finger protein APC11.

FIG. 11 shows the amino acid sequence of the RING finger protein ROC1.

FIGS. 12A and 12B show the nucleic acid sequence encoding the RING finger protein ROC2 and the amino acid sequence of ROC2, respectively.

FIGS. 13A and 13B show the nucleic acid sequence encoding the Cullin CUL5 and the amino acid sequence of CUL5, respectively.

FIGS. 14A and 14B show the nucleic acid sequence encoding the Cullin APC2 and the amino acid sequence of APC2, respectively.

FIGS. 15A, 15B and 15C (SEQ ID NOS:13–15) show the amino acid sequences of human ubiquitin, FLAG-ubiquitin and FLAG-Cys-ubiquitin, respectively. The FLAG (DYKDDDDK; SEQ ID NO:16) and FLAG-Cys (SEQ ID NO:17) portions of the sequence are shown in bold.

FIG. 16A shows the fluorescence signals of IAEDANS (490 nm; larger peak) and fluorescein (515 nm; smaller peak) labeled ubiquitin following combination with E1 and E2 only. The free ubiquitin was isolated using high performance liquid chromatography (HPLC). FIG. 16B shows the fluorescence signals of IAEDANS (490 nm; larger peak at each elution volume) and fluorescein (515 nm; smaller peak at each elution volume) labeled ubiquitin following combination with E1 and E2 and E3 (Roc l/ Cul1). The dashed line shows optical density of the protein solution (scale on right), revealing the high sensitivity of the fluorophores despite a very low concentration of protein.

DETAILED DESCRIPTION OF THE INVENTION

Figure 1:
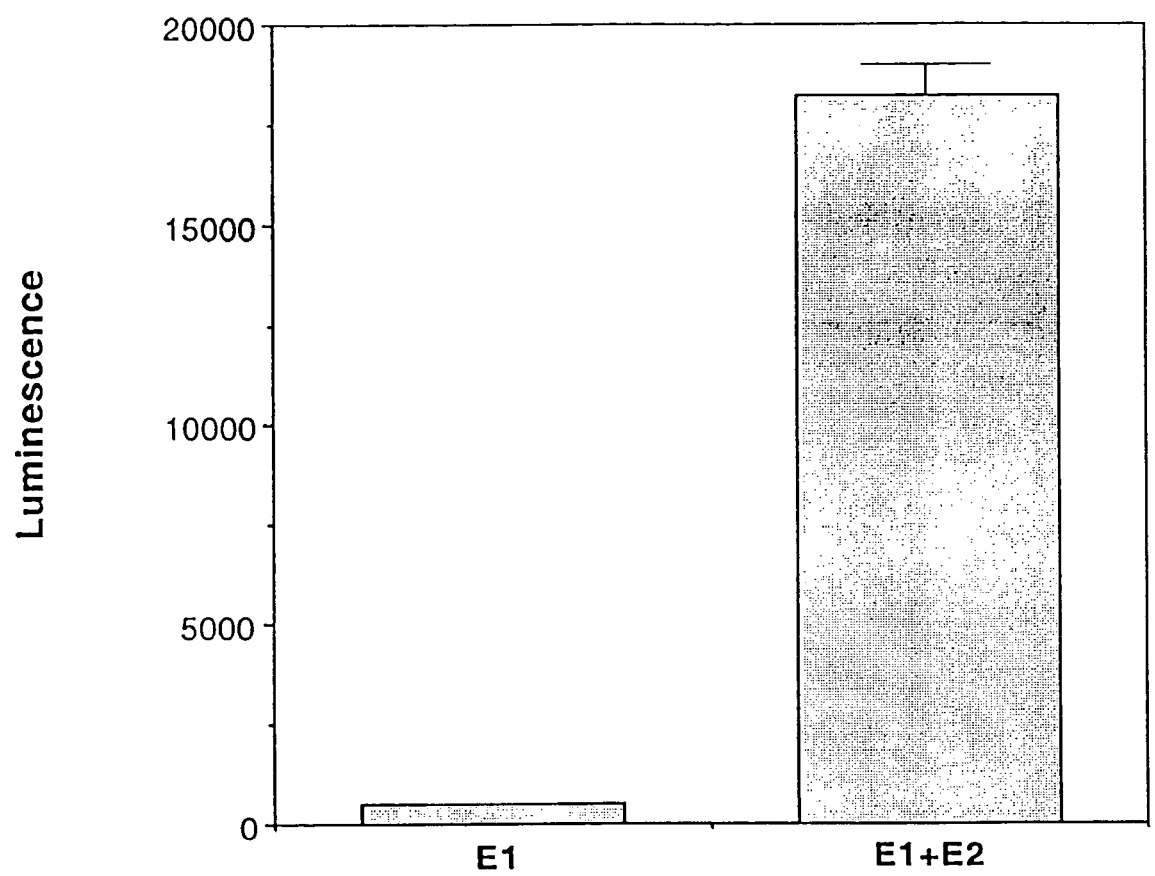
FIG. 1 shows the relative amounts of fluorescently labeled ubiquitin in a ubiquitin activating and conjugating assay. In these experiments, E2 is His-Ubch5c.

The present invention is directed to methods for assaying ubiquitin ligase activity. In a broad embodiment, the method provides measuring ubiquitin ligase activity directly where the reaction has occurred, thus obviating the need for target proteins and subsequent analysis such as separating ligated from unligated material in an SDS PAGE procedure. This allows multi-well array analysis and high throughput screening techniques for modulators of ubiquitination activity. In addition, the present methods allow the analysis of many different combinations of E3 components and E2/E3 combinations, without requiring prior identification of specific target substrates.

In general, the method involves combining ubiquitin and ubiquitin ligation enzymes and measuring the amount of ubiquitin ligated to a ubiquitination substrate protein. In a preferred embodiment, the ubiquitination substrate protein is ubiquitin itself, and what is measured is poly-ubiquitin chains produced in the ligase reaction. Therefore, as used herein, "ubiquitination substrate protein" means a protein to which ubiquitin is bound through the activity of ubiquitination enzymes and "ubiquitination" and grammatical equivalents thereof means the binding of ubiquitin to a substrate protein.

In a preferred embodiment, no specific target protein is used to measure ubiquitin ligase activity. By "target protein" herein is meant a protein other than ubiquitin to which ubiquitin is ligated by ubiquitination enzymes. In this embodiment, preferably, the poly-ubiquitin chains measured are bound to E3. In another preferred embodiment, the poly-ubiquitin chains measured may be bound to E3 or not.

In a preferred embodiment, E3 is attached to the surface of a reaction vessel, such as the well of a multi-well plate. This embodiment facilitates the separation of ligated ubiquitin from unligated ubiquitin. Means of attaching E3 to the surface of a reaction vessel are described below. This embodiment allows the ubiquitin ligase reaction and detection and measurement of ligated ubiquitin to occur in the same vessel, making the assay useful for high-throughput screening applications.

In another preferred embodiment, E3 is free in solution. In this embodiment, ubiquitination activity is monitored using a system that produces a signal which varies with the extent of ubiquitination, such as the fluorescence resonance energy transfer (FRET) system described in detail below.

In a preferred embodiment, the ubiquitin is labeled, either directly or indirectly, as further described below, and the amount of label is measured. This allows for easy and rapid detection and measurement of ligated ubiquitin, making the assay useful for high-throughput screening applications. In one preferred embodiment, the signal of the label varies with the extent of ubiquitination, such as in the FRET system described below. One of ordinary skill in the art will recognize the applicability of the present invention to screening for agents which modulate ubiquitination.

Accordingly, the present invention provides methods and compositions for assaying ubiquitin ligase activity. By "ubiquitin" herein is meant a polypeptide which is ligated to another polypeptide by ubiquitin ligase enzymes. The ubiquitin can be from any species of organism, preferably a eukaryotic species. Preferably, the ubiquitin is mammalian. More preferably, the ubiquitin is human ubiquitin. In a most preferred embodiment, the ubiquitin has the amino acid sequence depicted in FIG. 15A.

In a preferred embodiment, when ubiquitin is ligated to a target protein, that protein is targeted for degradation by the 26S proteasome.

Preferred embodiments of the invention utilize a 76 amino acid human ubiquitin. Other embodiments utilize variants of ubiquitin, as further described below.

Also encompassed by "ubiquitin" is naturally occurring alleles and man-made variants of such a 76 amino acid polypeptide. In a preferred embodiment, the ubiquitin has the amino acid sequence of that depicted in ATCC accession number P02248, incorporated herein by reference. ATCC accession numbers are found in Genbank. Sequences of GenBank accession numbers are incorporated herein by reference. GenBank is known in the art, see, e.g., Benson, D A, et al., Nucleic Acids Research 26:1–7 (1998) and http://www.ncbi.nlm.nih.gov/. Preferably, the ubiquitin has the amino acid sequence depicted in FIG. 15A. In a preferred embodiment, variants of ubiquitin have an overall amino acid sequence identity of preferably greater than about 75%, more preferably greater than about 80%, even more preferably greater than about 85% and most preferably greater than 90% of the amino acid sequence depicted in FIG. 15A. In some embodiments the sequence identity will be as high as about 93 to 95 or 98%.

In another preferred embodiment, a ubiquitin protein has an overall sequence similarity with the amino acid sequence depicted in FIG. 15A of greater than about 80%, more preferably greater than about 85%, even more preferably greater than about 90% and most preferably greater than 93%. In some embodiments the sequence identity will be as high as about 95 to 98 or 99%.

As is known in the art, a number of different programs can be used to identify whether a protein (or nucleic acid as discussed below) has sequence identity or similarity to a known sequence. Sequence identity and/or similarity is determined using standard techniques known in the art, including, but not limited to, the local sequence identity algorithm of Smith & Waterman, Adv. Appl. Math. 2:482 (1981), by the sequence identity alignment algorithm of Needleman & Wunsch, J. Mol. Biol. 48:443 (1970), by the search for similarity method of Pearson & Lipman, PNAS USA 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., *Nucl. Acid Res.* 12:387–395 (1984), preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127–149 (1988), Alan R. Liss, Inc.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, J. Mol. Evol. 35:351–360 (1987); the method is similar to that described by Higgins & Sharp CABIOS 5:151–153 (1989). Useful PILEUP parameters including a default gap weight of 3.00, a default gap length weight of 0.10, and weighted end gaps.

Another example of a useful algorithm is the BLAST algorithm, described in Altschul et al., J. Mol. Biol. 215, 403–410, (1990) and Karlin et al., PNAS USA 90:5873–5787 (1993). A particularly useful BLAST program is the WU-BLAST-2 program which was obtained from Altschul et al., *Methods in Enzymology,* 266: 460–480 (1996); http://blast.wustl/edu/blast/README.html]. WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al. Nucleic Acids Res. 25:3389–3402. Gapped BLAST uses BLOSUM-62 substitution scores; threshold T parameter set to 9; the two-hit method to trigger ungapped extensions; charges gap lengths of k a cost of 10+k; $X_u$ set to 16, and $X_g$ set to 40 for database search stage and to 67 for the output stage of the algorithms. Gapped alignments are triggered by a score corresponding to ~22 bits.

A percent amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

The alignment may include the introduction of gaps in the sequences to be aligned. In addition, for sequences which contain either more or fewer amino acids than the amino acid sequence depictd in FIG. 15A, it is understood that in one embodiment, the percentage of sequence identity will be determined based on the number of identical amino acids in relation to the total number of amino acids. Thus, for example, sequence identity of sequences shorter than that of the sequence depicted in FIG. 15A, as discussed below, will be determined using the number of amino acids in the shorter sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

Ubiquitin proteins of the present invention may be shorter or longer than the amino acid sequence depicted in FIG. 15A. Thus, in a preferred embodiment, included within the definition of ubiquitin are portions or fragments of the amino acid sequence depicted in FIG. 15A. In one embodiment herein, fragments of ubiquitin are considered ubiquitin proteins if they are ligated to another polypeptide by ubiquitin ligase enzymes.

In addition, as is more fully outlined below, ubiquitin can be made longer than the amino acid sequence depicted in FIG. 15A; for example, by the addition of tags, the addition of other fusion sequences, or the elucidation of additional coding and non-coding sequences. As described below, the fusion of a ubiquitin peptide to a fluorescent peptide, such as Green Fluorescent Peptide (GFP), is particularly preferred.

The ubiquitin protein, as well as other proteins of the present invention, are preferably recombinant. A "recombinant protein" is a protein made using recombinant techniques, i.e. through the expression of a recombinant nucleic acid as described below. In a preferred embodiment, the ubiquitin of the invention is made through the expression of a nucleic acid as depicted in ATCC accession number M26880 or AB003730, or a fragment thereof. In a most preferred embodiment, the nucleic acid encodes the amino acid sequence depicted in FIG. 15A. A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of a protein from one organism in a different organism or host cell. Alternatively, the protein may be made at a significantly higher concentration than is normally seen, through the use of an inducible promoter or high expression promoter, such that the protein is made at increased concentration levels. Alternatively, the protein may be in a form not normally found in nature, as in the addition of an epitope tag or amino acid substitutions, insertions and deletions, as discussed below.

As used herein and further defined below, "nucleic acid" may refer to either DNA or RNA, or molecules which contain both deoxy- and ribonucleotides. The nucleic acids include genomic DNA, cDNA and oligonucleotides including sense and anti-sense nucleic acids. Such nucleic acids may also contain modifications in the ribose-phosphate backbone to increase stability and half life of such molecules in physiological environments.

The nucleic acid may be double stranded, single stranded, or contain portions of both double stranded or single stranded sequence. As will be appreciated by those in the art, the depiction of a single strand ("Watson") also defines the sequence of the other strand ("Crick"); thus the sequences depicted in FIGS. 1 and 3 also include the complement of the sequence. By the term "recombinant nucleic acid" herein is meant nucleic acid, originally formed in vitro, in general, by the manipulation of nucleic acid by endonucleases, in a form not normally found in nature. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

The terms "polypeptide" and "protein" may be used interchangeably throughout this application and mean at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and norleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradation.

In one embodiment, the present invention provides compositions containing protein variants, for example ubiquitin, E1, E2 and/or E3 variants. These variants fall into one or more of three classes: substitutional, insertional or deletional variants. These variants ordinarily are prepared by site specific mutagenesis of nucleotides in the DNA encoding a protein of the present compositions, using cassette or PCR mutagenesis or other techniques well known in the art, to produce DNA encoding the variant, and thereafter expressing the DNA in recombinant cell culture as outlined above. However, variant protein fragments having up to about 100–150 residues may be prepared by in vitro synthesis using established techniques. Amino acid sequence variants are characterized by the predetermined nature of the variation, a feature that sets them apart from naturally occurring allelic or interspecies variation of the protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed variants screened for the optimal desired activity. Techniques for making substitution mutations at predetermined sites in DNA having a known sequence are well known, for example, M13 primer mutagenesis and PCR mutagenesis. Rapid production of many variants may be done using techniques such as the method of gene shuffling, whereby fragments of similar variants of a nucleotide sequence are allowed to recombine to produce new variant combinations. Examples of such techniques are found in U.S. Pat. Nos. 5,605,703; 5,811,238; 5,873,458; 5,830,696; 5,939,250; 5,763,239; 5,965,408; and 5,945,325, each of which is incorporated by reference herein in its entirety. Screening of the mutants is done using ubiquitin ligase activity assays of the present invention.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the protein are desired, substitutions are generally made in accordance with the following chart:

CHART I

| Original Residue | Exemplary Substitutions |
|---|---|
| Ala | Ser |
| Arg | Lys |
| Asn | Gln, His |
| Asp | Glu |
| Cys | Ser, Ala |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and will elicit the same immune response as the naturally-occurring analogue, although variants also are selected to modify the characteristics of the proteins as needed. Alternatively, the variant may be designed such that the biological activity of the protein is altered. For example, glycosylation sites may be altered or removed.

Covalent modifications of polypeptides are included within the scope of this invention. One type of covalent modification includes reacting targeted amino acid residues of a polypeptide with an organic derivatizing agent that is capable of reacting with selected side chains or the N-or C-terminal residues of a polypeptide. Derivatization with bifunctional agents is useful, for instance, for crosslinking a protein to a water-insoluble support matrix or surface for use in the method for screening assays, as is more fully described below. Commonly used crosslinking agents include, e.g., 1,1-bis(diazoacetyl)-2-phenylethane, glutaraldehyde, -hydroxy-succinimide esters, for example, esters with 4-azidosalicylic acid, homobifunctional imidoesters, including disuccinimidyl esters such as 3,3'-dithiobis(succinimidyl-propionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties*, W. H. Freeman & Co., San Francisco, pp. 79–86 (1983)], acetylation of the N-terminal amine, and amidation of any C-terminal carboxyl group.

Another type of covalent modification of a polypeptide included within the scope of this invention comprises altering the native glycosylation pattern of the polypeptide. "Altering the native glycosylation pattern" is intended for purposes herein to mean deleting one or more carbohydrate moieties found in native sequence polypeptide, and/or adding one or more glycosylation sites that are not present in the native sequence polypeptide.

Addition of glycosylation sites to polypeptides may be accomplished by altering the amino acid sequence thereof. The alteration may be made, for example, by the addition of, or substitution by, one or more serine or threonine residues to the native sequence polypeptide (for O-linked glycosylation sites). The amino acid sequence may optionally be altered through changes at the DNA level, particularly by mutating the DNA encoding the polypeptide at preselected bases such that codons are generated that will translate into the desired amino acids.

Another means of increasing the number of carbohydrate moieties on a polypeptide is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem.*, pp. 259–306 (1981).

Removal of carbohydrate moieties present on the polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo-and exo-glycosidases as described by Thotakura et al., *Meth. Enzymol.*, 138:350 (1987).

Another type of covalent modification of a protein comprises linking the polypeptide to one of a variety of non-proteinaceous polymers, e.g., polyethylene glycol, polypropylene glycol, or polyoxyalkylenes, in the manner set forth in U.S. Pat. Nos. 4,640,835; 4,496,689; 4,301,144; 4,670, 417; 4,791,192 or 4,179,337.

Polypeptides of the present invention may also be modified in a way to form chimeric molecules comprising a first polypeptide fused to another, heterologous polypeptide or amino acid sequence. In one embodiment, such a chimeric molecule comprises a fusion of a ubiquitin polypeptide (or an E2 or an E3, as defined below) with a tag polypeptide which provides an epitope to which an anti-tag antibody can selectively bind. The epitope tag is generally placed at the amino-or carboxyl-terminus of the polypeptide. The presence of such epitope-tagged forms of a polypeptide can be detected using an antibody against the tag polypeptide. Also, providing an epitope tag enables the polypeptide to be readily purified by affinity purification using an anti-tag antibody or another type of affinity matrix that binds to the epitope tag. In an alternative embodiment, the chimeric molecule may comprise a fusion of a polypeptide disclosed herein with an immunoglobulin or a particular region of an immunoglobulin. For a bivalent form of the chimeric molecule, such a fusion could be to the Fc region of an IgG molecule. Tags for components of the invention are defined and described in detail below.

The present invention provides methods for assaying ubiquitin ligase activity. By "ubiquitin ligase" is meant a ubiquitination enzyme capable of catalyzing the covalent binding of a ubiquitin to another protein. Preferred embodiments of the invention involve combining ubiquitin and ubiquitination enzymes, including ubiquitin ligase, under conditions in which ubiquitination may take place, and measuring the amount of ubiquitin (poly-ubiquitin) bound to the ubiquitin ligase. In a preferred embodiment, the ubiquitin ligase is an E3 ubiquitin ligase, defined below.

Embodiments of the present invention involve binding ubiquitin to a ubiquitination substrate protein. By "ubiquitination substrate protein" is meant a protein to which the ubiquitin ligase can catalyze the covalent binding of ubiquitin and includes target proteins and ubiquitin. In a preferred embodiment, the ubiquitination substrate protein is ubiquitin and the ubiquitin ligase catalyzes the formation of polyubiquitin chains. In a preferred embodiment, the polyubiquitin chains are formed by the ubiquitin ligase in the absence of any target protein.

In one aspect, the invention provides methods for assaying ubiquitination. In these assays, the interaction of the different ubiquitination enzymes, the interaction of different subunits of individual ubiquitination enzymes, and the influence of candidate ubiquitination modulators can be observed and measured.

In a preferred embodiment, the invention is directed to a method of assaying ubiquitin ligase activity. By "ubiquitin ligase activity", "ubiquitin ligation" and grammatical equivalents thereof is meant the catalysis of the covalent binding of ubiquitin to a substrate protein. Preferably, each ubiquitin is bound such that a subsequent ubiquitin polypeptide may be bound to it, to form chains comprising a plurality of ubiquitin molecules. In a preferred embodiment, ubiquitin ligase activity occurs in the absence of target proteins, thus the substrate protein is ubiquitin.

In a preferred embodiment, the invention is additionally directed to a method of assaying ubiquitin activating activity. By "ubiquitin activating activity", "ubiquitin activation" and grammatical equivalents thereof is meant the binding of ubiquitin and E1. Preferably, E1 forms a high energy thiolester bond with the ubiquitin.

In a preferred embodiment, the invention is also directed to a method of assaying ubiquitin conjugating activity. By "ubiquitin conjugating activity", "ubiquitin conjugation" and grammatical equivalents thereof is meant the binding of activated ubiquitin with an E2. As will be appreciated by those in the art, due to the presence of the high energy thiolester bond in the E2-ubiquitin conjugate, conjugated ubiquitin may be joined to other ubiquitin at a low rate in the absence of the catalytic activity of E3. Therefore, some of the ubiquitin measured in a ubiquitin conjugating activity assay will be in the form of poly-ubiquitin.

The present invention provides methods and compositions comprising combining ubiquitin with other components. By "combining" is meant the addition of the various components into a receptacle under conditions in which ubiquitin ligase activity or ubiquitination may take place. In a preferred embodiment, the receptacle is a well of a 96 well plate or other commercially available multiwell plate. In an alternate preferred embodiment, the receptacle is the reaction vessel of a FACS machine. Other receptacles useful in the present invention include, but are not limited to 384 well plates and 1536 well plates. Still other receptacles useful in the present invention will be apparent to the skilled artisan.

The addition of the components may be sequential or in a predetermined order or grouping, as long as the conditions amenable to ubiquitin ligase activity are obtained. Such conditions are well known in the art, and further guidance is provided below.

In a preferred embodiment, one or more components of the present invention comprise a tag. By "tag" is meant an attached molecule or molecules useful for the identification or isolation of the attached component. Components having a tag are referred to as "tag-X", wherein X is the component. For example, a ubiquitin comprising a tag is referred to herein as "tag-ubiquitin". Preferably, the tag is covalently bound to the attached component. When more than one component of a combination has a tag, the tags will be numbered for identification, for example "tag1-ubiquitin". Components may comprise more than one tag, in which case each tag will be numbered, for example "tag1,2-ubiquitin". Preferred tags include, but are not limited to, a label, a partner of a binding pair, and a surface substrate binding molecule. As will be evident to the skilled artisan, many molecules may find use as more than one type of tag, depending upon how the tag is used.

By "label" is meant a molecule that can be directly (i.e., a primary label) or indirectly (i.e., a secondary label) detected; for example a label can be visualized and/or measured or otherwise identified so that its presence or absence can be known. As will be appreciated by those in the art, the manner in which this is done will depend on the label. Preferred labels include, but are not limited to, fluorescent labels, label enzymes and radioisotopes.

By "fluorescent label" is meant any molecule that may be detected via its inherent fluorescent properties. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, Texas Red, IAEDANS, EDANS, BODIPY FL, LC Red 640, Cy 5, Cy 5.5, LC Red 705 and Oregon green. Suitable optical dyes are described in the 1996 Molecular Probes Handbook by Richard P. Haugland, hereby expressly incorporated by reference. Suitable fluorescent labels also include, but are not limited to, green fluorescent protein (GFP; Chalfie, et al., *Science* 263(5148):802–805 (Feb. 11, 1994); and EGFP; Clontech—Genbank Accession Number U55762), blue fluorescent protein (BFP; 1. Quantum Biotechnologies, Inc. 1801 de Maisonneuve Blvd. West, 8th Floor, Montreal (Quebec) Canada H3H 1J9; 2. Stauber, R. H. Biotechniques 24(3):462–471 (1998); 3. Heim, R. and Tsien, R. Y. Curr. Biol. 6:178–182 (1996)), enhanced yellow fluorescent protein (EYFP; 1. Clontech Laboratories, Inc., 1020 East Meadow Circle, Palo Alto, Calif. 94303), luciferase (Ichiki, et al., *J. Immunol.* 150(12):5408–5417 (1993)), β-galactosidase (Nolan, et al., *Proc Natl Acad Sci USA* 85(8):2603–2607 (April 1988)) and Renilla WO 92/15673; WO 95/07463; WO 98/14605; WO 98/26277; WO 99/49019; U.S. Pat. No. 5,292,658; U.S. Pat. No. 5,418,155; U.S. Pat. No. 5,683,888; U.S. Pat. No. 5,741,668; U.S. Pat. No. 5,777,079; U.S. Pat. No. 5,804,387; U.S. Pat. No. 5,874,304; U.S. Pat. No. 5,876,995; and U.S. Pat. No. 5,925,558) All of the above-cited references are expressly incorporated herein by reference.

In some instances, multiple fluorescent labels are employed. In a preferred embodiment, at least two fluorescent labels are used which are members of a fluorescence resonance energy transfer (FRET) pair. FRET is phenomenon known in the art wherein excitation of one fluorescent dye is transferred to another without emission of a photon. A FRET pair consists of a donor fluorophore and an acceptor fluorophore. The fluorescence emission spectrum of the donor and the fluorescence absorption spectrum of the acceptor must overlap, and the two molecules must be in close proximity. The distance between donor and acceptor at which 50% of donors are deactivated (transfer energy to the acceptor) is defined by the Förster radius ($R_o$), which is typically 10–100 Å. Changes in the fluorescence emission spectrum comprising FRET pairs can be detected, indicating changes in the number of that are in close proximity (i.e., within 100 Å of each other). This will typically result from the binding or dissociation of two molecules, one of which is labeled with a FRET donor and the other of which is labeled with a FRET acceptor, wherein such binding brings the FRET pair in close proximity. Binding of such molecules will result in an increased fluorescence emission of the acceptor and/or quenching of the fluorescence emission of the donor.

FRET pairs (donor/acceptor) useful in the invention include, but are not limited to, EDANS/fluorescien, IAEDANS/fluorescein, fluorescein/tetramethylrhodamine, fluorescein/LC Red 640, fluorescein/Cy 5, fluorescein/Cy 5.5 and fluorescein/LC Red 705.

In another aspect of FRET, a fluorescent donor molecule and a nonfluorescent acceptor molecule ("quencher") may be employed. In this application, fluorescent emission of the donor will increase when quencher is displaced from close proximity to the donor and fluorescent emission will decrease when the quencher is brought into close proximity to the donor. Useful quenchers include, but are not limited to, DABCYL, QSY 7 and QSY 33. Useful fluorescent donor/quencher pairs include, but are not limited to EDANS/DABCYL, Texas Red/DABCYL, BODIPY/DABCYL, Lucifer yellow/DABCYL, coumarin/DABCYL and fluorescein/QSY 7 dye.

The skilled artisan will appreciate that FRET and fluorescence quenching allow for monitoring of binding of labeled molecules over time, providing continuous information regarding the time course of binding reactions.

It is important to remember that ubiquitin is ligated to substrate protein by its terminal carboxyl group to a lysine residue, including lysine residues on other ubiquitin. Therefore, attachment of labels or other tags should not interfere with either of these active groups on the ubiquitin. Amino acids may be added to the sequence of protein, through means well known in the art and described herein, for the express purpose of providing a point of attachment for a label. In a preferred embodiment, one or more amino acids are added to the sequence of a component for attaching a tag thereto, preferably a fluorescent label. In a preferred embodiment, the amino acid to which a fluorescent label is attached is Cysteine.

By "label enzyme" is meant an enzyme which may be reacted in the presence of a label enzyme substrate which produces a detectable product. Suitable label enzymes for use in the present invention include but are not limited to, horseradish peroxidase, alkaline phosphatase and glucose oxidase. Methods for the use of such substrates are well known in the art. The presence of the label enzyme is generally revealed through the enzyme's catalysis of a reaction with a label enzyme substrate, producing an identifiable product. Such products may be opaque, such as the reaction of horseradish peroxidase with tetramethyl benzedine, and may have a variety of colors. Other label enzyme substrates, such as Luminol (available from Pierce Chemical Co.), have been developed that produce fluorescent reaction products. Methods for identifying label enzymes with label enzyme substrates are well known in the art and many commercial kits are available. Examples and methods for the use of various label enzymes are described in Savage et al., *Previews* 247:6–9 (1998), Young, *J. Virol. Methods* 24:227–236 (1989), which are each hereby incorporated by reference in their entirety.

By "radioisotope" is meant any radioactive molecule. Suitable radioisotopes for use in the invention include, but are not limited to $^{14}C$, $^{3}H$, $^{32}P$, $^{33}P$, $^{35}S$, $^{125}I$, and $^{131}I$. The use of radioisotopes as labels is well known in the art.

In addition, labels may be indirectly detected, that is, the tag is a partner of a binding pair. By "partner of a binding pair" is meant one of a first and a second moiety, wherein said first and said second moiety have a specific binding affinity for each other. Suitable binding pairs for use in the invention include, but are not limited to, antigens/antibodies (for example, digoxigenin/anti-digoxigenin, dinitrophenyl (DNP)/anti-DNP, dansyl-X-anti-dansyl, Fluorescein/anti-fluorescein, lucifer yellow/anti-lucifer yellow, and rhodamine/anti-rhodamine), biotin/avidin (or biotin/streptavidin) and calmodulin binding protein (CBP)/calmodulin. Other suitable binding pairs include polypeptides such as the FLAG-peptide (DYKDDDDK; SEQ ID NO:16) [Hopp et al., *BioTechnology*, 6:1204–1210 (1988)]; the KT3 epitope peptide [Martin et al., *Science* 255:192–194 (1992)]; tubulin epitope peptide [Skinner et al., *J. Biol. Chem* 266:15163–15166 (1991)]; and the T7 gene 10 protein peptide tag [Lutz-Freyermuth et al., *Proc. Natl. Acad. Sci. USA*, 87:6393–6397 (1990)] and the antibodies each thereto. Generally, in a preferred embodiment, the smaller of the binding pair partners serves as the tag, as steric considerations in ubiquitin ligation may be important. As will be appreciated by those in the art, binding pair partners may be used in applications other than for labeling, as is further described below.

As will be appreciated by those in the art, a partner of one binding pair may also be a partner of another binding pair. For example, an antigen (first moiety) may bind to a first antibody (second moiety) which may, in turn, be an antigen for a second antibody (third moiety). It will be further appreciated that such a circumstance allows indirect binding of a first moiety and a third moiety via an intermediary second moiety that is a binding pair partner to each.

As will be appreciated by those in the art, a partner of a binding pair may comprise a label, as described above. It will further be appreciated that this allows for a tag to be indirectly labeled upon the binding of a binding partner comprising a label. Attaching a label to a tag which is a partner of a binding pair, as just described, is referred to herein as "indirect labeling".

By "surface substrate binding molecule" and grammatical equivalents thereof is meant a molecule have binding affinity for a specific surface substrate, which substrate is generally a member of a binding pair applied, incorporated or otherwise attached to a surface. Suitable surface substrate binding molecules and their surface substrates include, but are not limited to poly-histidine (poly-his) or poly-histidine-glycine (poly-his-gly) tags and Nickel substrate; the Glutathione-S Transferase tag and its antibody substrate (available from Pierce Chemical); the flu HA tag polypeptide and its antibody 12CA5 substrate [Field et al., *Mol. Cell. Biol.*, 8:2159–2165 (1988)]; the c-myc tag and the 8F9, 3C7, 6E10, G4, B7 and 9E10 antibody substrates thereto [Evan et al., *Molecular and Cellular Biology*, 5:3610–3616 (1985)]; and the Herpes Simplex virus glycoprotein D (gD) tag and its antibody substrate [Paborsky et al., *Protein Engineering*, 3(6):547–553 (1990)]. In general, surface binding substrate molecules useful in the present invention include, but are not limited to, polyhistidine structures (His-tags) that bind nickel substrates, antigens that bind to surface substrates comprising antibody, haptens that bind to avidin substrate (e.g., biotin) and CBP that binds to surface substrate comprising calmodulin.

Production of antibody-embedded substrates is well known; see Slinkin et al., *Bioconj. Chem.* 2:342–348 (1991); Torchilin et al., supra; Trubetskoy et al., *Bioconj. Chem.* 3:323–327 (1992); King et al., *Cancer Res.* 54:6176–6185 (1994); and Wilbur et al., *Bioconjugate Chem.* 5:220–235 (1994) (all of which are hereby expressly incorporated by reference), and attachment of or production of proteins with antigens is described above.

Calmodulin-embedded substrates are commercially available, and production of proteins with CBP is described in Simcox et al., *Strategies* 8:40–43 (1995), which is hereby incorporated by reference in its entirety.

As will be appreciated by those in the art, tag-components of the invention can be made in various ways, depending largely upon the form of the tag. Components of the invention and tags are preferably attached by a covalent bond.

The production of tag-polypeptides by recombinant means when the tag is also a polypeptide is described below. Production of FLAG (DYKDDDDK; SEQ ID NO:16)-labeled proteins is well known in the art and kits for such production are commercially available (for example, from Kodak and Sigma). Methods for the production and use of FLAG (DYKDDDDK; SEQ ID NO:16)-labeled proteins are found, for example, in Winston et al., *Genes and Devel.* 13:270–283 (1999), incorporated herein in its entirety, as well as product handbooks provided with the above-mentioned kits.

Biotinylation of target molecules and substrates is well known, for example, a large number of biotinylation agents are known, including amine-reactive and thiol-reactive agents, for the biotinylation of proteins, nucleic acids, carbohydrates, carboxylic acids; see chapter 4, Molecular Probes Catalog, Haugland, 6th Ed. 1996, hereby incorporated by reference. A biotinylated substrate can be attached to a biotinylated component via avidin or streptavidin. Similarly, a large number of haptenylation reagents are also known (Id.).

Methods for labeling of proteins with radioisotopes are known in the art. For example, such methods are found in Ohta et al., *Molec. Cell* 3:535–541 (1999), which is hereby incorporated by reference in its entirety.

Production of proteins having His-tags by recombinant means is well known, and kits for producing such proteins are commercially available. Such a kit and its use is described in the QIAexpress Handbook from Quiagen by Joanne Crowe et al., hereby expressly incorporated by reference.

The functionalization of labels with chemically reactive groups such as thiols, amines, carboxyls, etc. is generally known in the art. In a preferred embodiment, the tag is functionalized to facilitate covalent attachment.

The covalent attachment of the tag may be either direct or via a linker. In one embodiment, the linker is a relatively short coupling moiety, that is used to attach the molecules. A coupling moiety may be synthesized directly onto a component of the invention, ubiquitin for example, and contains at least one functional group to facilitate attachment of the tag. Alternatively, the coupling moiety may have at least two functional groups, which are used to attach a functionalized component to a functionalized tag, for example. In an additional embodiment, the linker is a polymer. In this embodiment, covalent attachment is accomplished either directly, or through the use of coupling moieties from the component or tag to the polymer. In a preferred embodiment, the covalent attachment is direct, that is, no linker is used. In this embodiment, the component preferably contains a functional group such as a carboxylic acid which is used for direct attachment to the functionalized tag. It should be understood that the component and tag may be attached in a variety of ways, including those listed above. What is important is that manner of attachment does not significantly alter the functionality of the component. For example, in tag-ubiquitin, the tag should be attached in such a manner as to allow the ubiquitin to be covalently bound to other ubiquitin to form polyubiquitin chains. As will be appreciated by those in the art, the above description of covalent attachment of a label and ubiquitin applies equally to the attachment of virtually any two molecules of the present disclosure.

In a preferred embodiment, the tag is functionalized to facilitate covalent attachment, as is generally outlined above. Thus, a wide variety of tags are commercially available which contain functional groups, including, but not limited to, isothiocyanate groups, amino groups, haloacetyl groups, maleimides, succinimidyl esters, and sulfonyl halides, all of which may be used to covalently attach the tag to a second molecule, as is described herein. The choice of the functional group of the tag will depend on the site of attachment to either a linker, as outlined above or a component of the invention. Thus, for example, for direct linkage to a carboxylic acid group of a ubiquitin, amino modified or hydrazine modified tags will be used for coupling via carbodiimide chemistry, for example using 1-ethyl-3-(3-dimethylaminopropyl)-carbodiimide (EDAC) as is known in the art (see Set 9 and Set 11 of the Molecular Probes Catalog, supra; see also the Pierce 1994 Catalog and Handbook, pages T-155 to T-200, both of which are hereby incorporated by reference). In one embodiment, the carbodiimide is first attached to the tag, such as is commercially available for many of the tags described herein.

In a preferred embodiment, ubiquitin is in the form of tag-ubiquitin.

In a preferred embodiment, ubiquitin is in the form of tag-ubiquitin, wherein, tag is a partner of a binding pair. Preferably in this embodiment the tag is FLAG (DYKDDDDK; SEQ ID NO:16) and the binding partner is anti-FLAG (DYKDDDDK; SEQ ID NO:16). Preferably in this embodiment, a label is attached to the FLAG (DYKDDDDK; SEQ ID NO:16) by indirect labeling. Preferably, the label is a label enzyme. Most preferably, the label enzyme is horseradish peroxidase, which is reacted with a fluorescent label enzyme substrate. Preferably, the label enzyme substrate is Luminol. Alternatively, the label is a fluorescent label.

In another preferred embodiment, ubiquitin is in the form of tag-ubiquitin, wherein the tag is a fluorescent label. In a particularly preferred embodiment, ubiquitin is in the form of tag1-ubiquitin and tag2-ubiquitin, wherein tag1 and tag2 are the members of a FRET pair. In an alternate preferred embodiment, ubiquitin is in the form of tag1-ubiquitin and tag2-ubiquitin, wherein tag1 is a fluorescent label and tag2 is a quencher of the fluorescent label. In either of these preferred embodiments, when tag1-ubiquitin and tag2-ubiquitin are bound through the activity of a ubiquitin ligase, preferably tag1 and tag2 are within 100 Å of each other, more preferable within 70 Å, still more preferably within 50 Å, even more preferably within 40 Å, and in some cases, preferably within 30 Å or less.

In yet another preferred embodiment, ubiquitin is in the form of tag1,2-ubiquitin and tag1,3-ubiquitin, wherein tag1 is a member of a binding pair, preferably FLAG (DYKDDDDK; SEQ ID NO:16), tag2 is a fluorescent label and tag3 is either a fluorescent label such that tag2 and tag3 are members of a FRET pair or tag3 is a quencher of tag2.

In a preferred embodiment, one or more amino acids are added to the ubiquitin sequence, using recombinant techniques as described herein, to provide an attachment point for a tag, preferably a fluorescent label or a quencher. In a preferred embodiment, the one or more amino acids are Cys or Ala-Cys. Preferably, the one or more amino acids are attached to the N-terminal of the ubiquitin. In a preferred embodiment, the one or more amino acids intervenes the sequence of a FLAG (DYKDDDDK; SEQ ID NO:16) tag and the ubiquitin. In a preferred embodiment, the tag, preferably a fluorescent label or a quencher, is attached to the added Cysteine.

The present invention provides methods and compositions comprising combining ubiquitin and E1. By "E1" is meant a ubiquitin activating enzyme. In a preferred embodiment, E1 is capable of transferring ubiquitin to an E2, defined below. In a preferred embodiment, E1 binds ubiquitin. In a preferred embodiment, E1 forms a high energy thiolester bond with ubiquitin, thereby "activating" the ubiquitin.

Figure 6B:
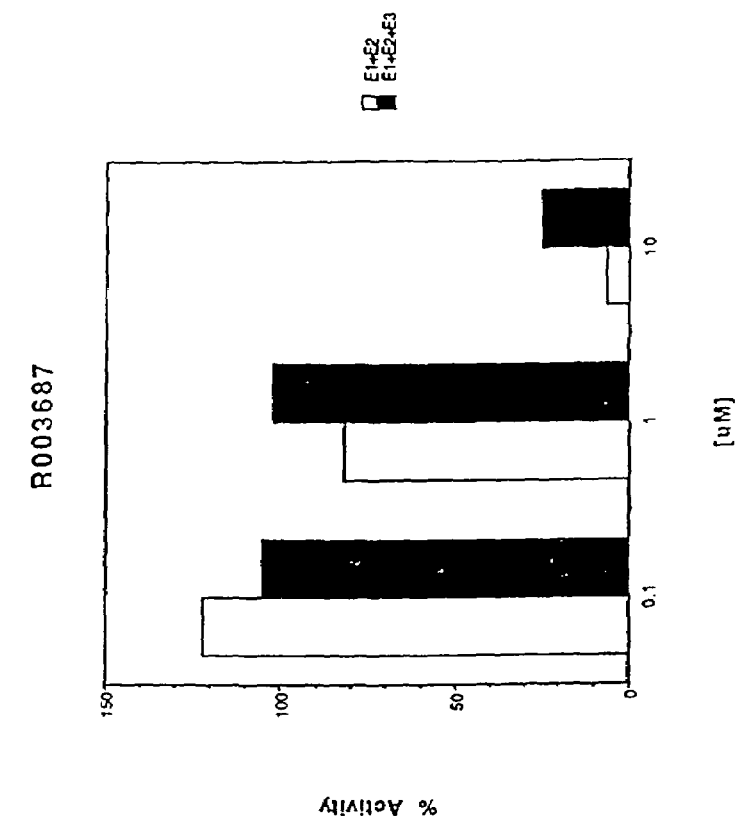
FIG. 6B shows candidate ubiquitination enzyme modulator that affects enzymes other than E3.
Figure 6A:
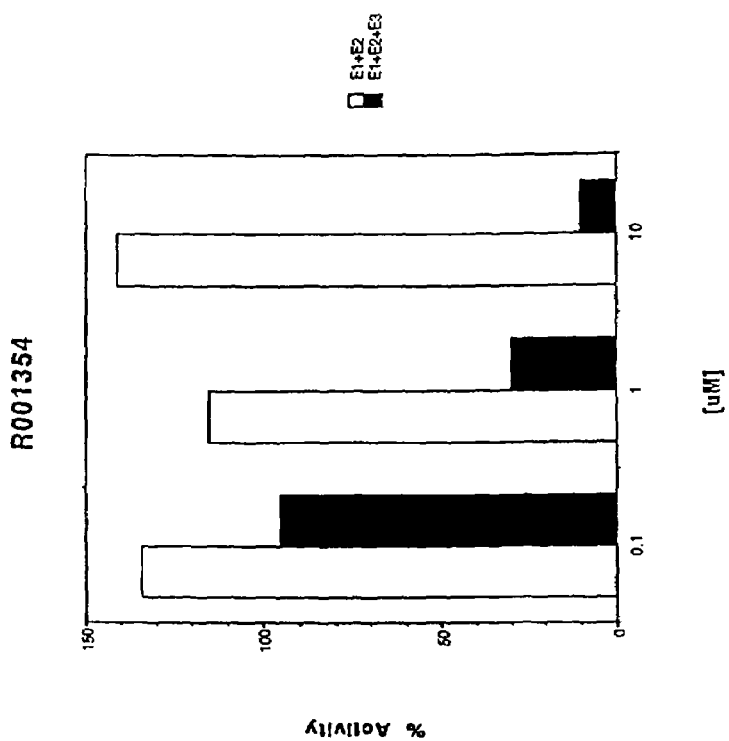
FIG. 6A shows a candidate ubiquitination enzyme modulator that affects only E3.

In a preferred embodiment, E1 proteins useful in the invention include those having the amino acid sequence of the polypeptide having ATCC accession numbers A38564, S23770, AAA61246, P22314, CAA40296 and BAA33144, incorporated herein by reference. In a preferred embodiment, E1 has the amino acid sequence shown in FIG. 6B or is encoded by a nucleic acid comprising the sequence shown in FIG. 6A. Preferably E1 is human E1. E1 is commercially available from Affiniti Research Products (Exeter, U.K.).

In a preferred embodiment, nucleic acids which may be used for producing E1 proteins for the invention include, but are not limited to, those disclosed by ATCC accession numbers M58028, X56976 and AB012190, incorporated herein by reference. In a preferred embodiment, E1 is encoded by a nucleic acid having a sequence consisting essentially of the sequence shown in FIG. 6A. Variants of the cited E1 proteins, also included in the term "E1", can be made as described herein.

In a preferred embodiment, the compositions of the invention comprise E2. By "E2" is meant a ubiquitin carrier enzyme (also known as a ubiquitin conjugating enzyme). In a preferred embodiment, ubiquitin is transferred from E1 to E2. In a preferred embodiment, the transfer results in a thiolester bond formed between E2 and ubiquitin. In a preferred embodiment, E2 is capable of transferring ubiquitin to an E3, defined below. In a preferred embodiment, the ubiquitination substrate protein is ubiquitin.

In a preferred embodiment, proteins which may be used in the present invention as E2 include, but are not limited to, those having the amino acid sequences disclosed in ATCC accession numbers AAC37534, P49427, CAA82525, AAA58466, AAC41750, P51669, AAA91460, AAA91461, CAA63538, AAC50633, P27924, AAB36017, Q16763, AAB86433, AAC26141, CAA04156, BAA11675, Q16781, NP_003333, BAB18652, AAH00468, CAC16955, CAB76865, CAB76864, NP_05536, O00762, XP_009804, XP_009488, XP_006823, XP_006343, XP_005934, XP_002869, XP_003400XP_009365, XP_010361, XP_004699, XP_004019, O14933, P27924, P50550, P52485, P51668, P51669, P49459, P37286, P23567, P56554, and CAB45853, each of which is incorporated herein by reference. Particularly preferred are sequences disclosed in ATCC accession numbers NP003331, NP003330, NP003329, P49427, AAB53362, NP008950, XP009488and AAC41750, also incorporated by reference. The skilled artisan will appreciate that many different E2 proteins and isozymes are known in the filed and may be used in the present invention, provided that the E2 has ubiquitin conjugating activity. Also specifically included within the term "E2" are variants of E2, which can be made as described herein.

In a preferred embodiment, E2 is one of Ubc5 (Ubch5, preferably Ubch5c), Ubc3 (Ubch3), Ubc4 (Ubch4) and UbcX (Ubc10, Ubch10). In a preferred embodiment, E2 is Ubc5c. In a preferred embodiment, E2 has the amino acid sequence shown in FIG. 7B or is encoded by a nucleic acid consisting essentially of the sequence shown in FIG. 7A.

In a preferred embodiment, nucleic acids which may be used to make E2 include, but are not limited to, those nucleic acids having sequences disclosed in ATCC accession numbers L2205, Z29328, M92670, L40146, U39317, U39318, X92962, U58522, S81003, AF031141, AF075599, AJ000519, XM009488, NM007019, U73379, L40146 and D83004, each of which is incorporated herein by reference. As described above, variants of these and other E2 encoding nucleic acids may also be used to make variant E2 proteins.

Figure 7A:
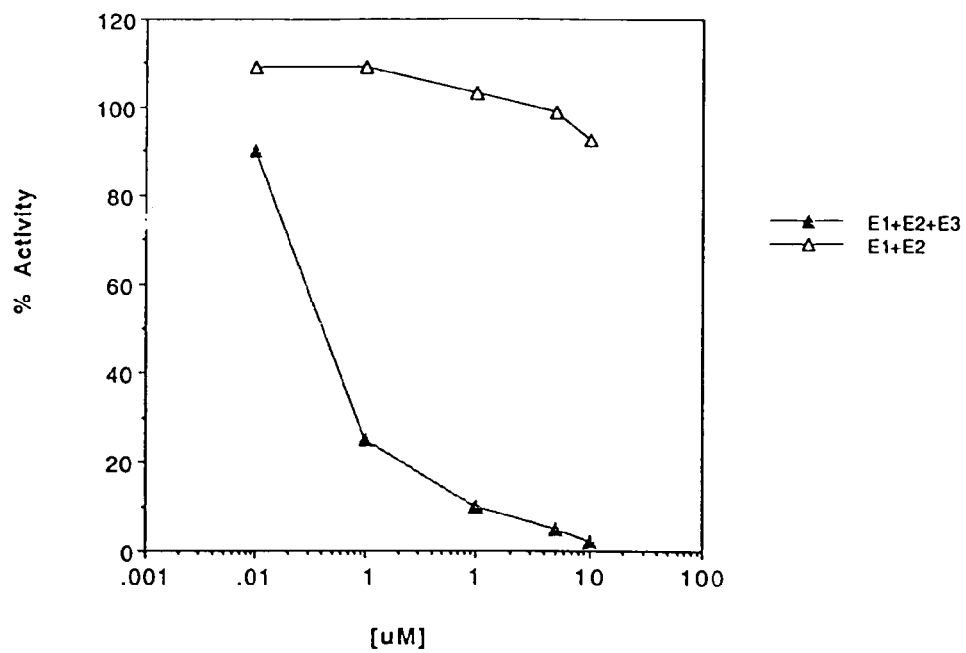
FIG. 7A shows the results for a candidate modulator having a concentration-dependent effect on ubiquitin ligase activity (E1+E2+E3), but not have on ubiquitin conjugating activity (E1+E2), thus affecting only the E3 ligase.
Figure 7B:
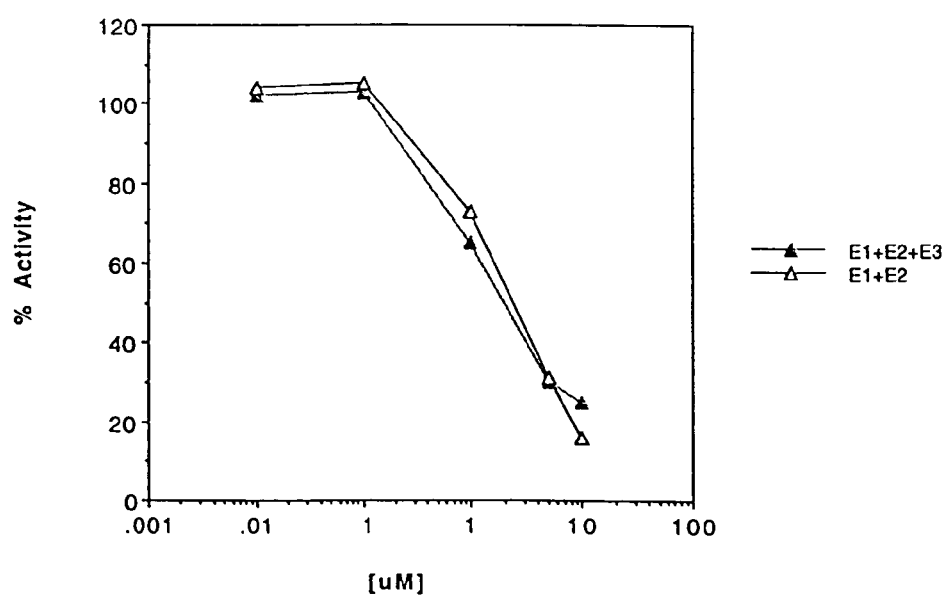
FIG. 7B shows the results for a candidate modulator having a concentration-dependent effect on both ubiquitin conjugating activity and ubiquitin ligase activity, thus affecting a component other than the E3 ligase.
Figure 16B:
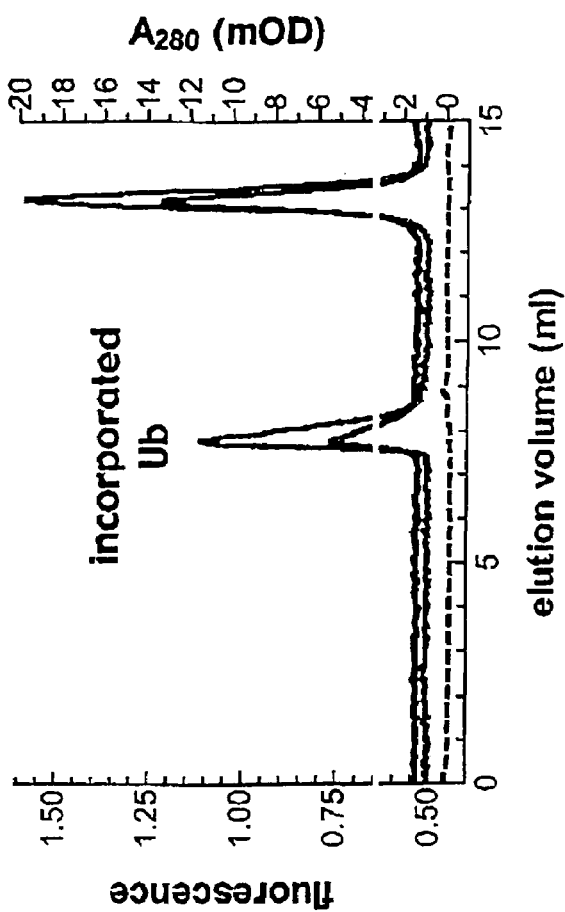
FIGS. 16A and 16B show the E3 ligase dependent incorporation of FLAG-Ala-Cys-ubiquitin (SEQ ID NO:18) labeled with FRET fluorophores into E3-ubiquitin complex. Isolation by HPLC shows emissions from free ubiquitin and ubiquitin attached to the E3 ligase. The traces show fluorescent emission at the wavelength described below, under excitation at 336 nm, the optimal excitation wavelength for IAEDANS.
Figure 16A:
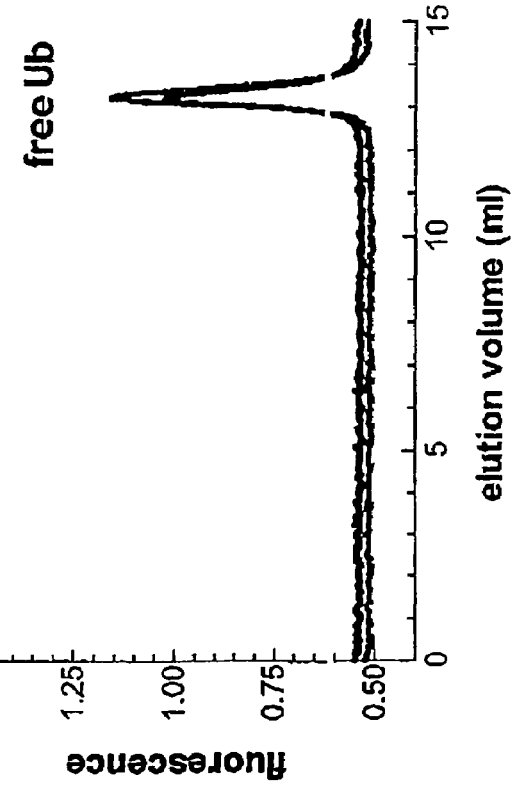

In a preferred embodiment, the nucleic acid used to make E2 comprises the sequence shown in FIG. 7A.

In a preferred embodiment, E2 has a tag, as defined above, with the complex being referred to herein as "tag-E2". Preferred E2 tags include, but are not limited to, labels, partners of binding pairs and substrate binding elements. In a most preferred embodiment, the tag is a His-tag or GST-tag.

The present invention provides methods and compositions comprising E3. By "E3" is meant a ubiquitin ligase, as defined above, comprising one or more components associated with ligation of ubiquitin to a ubiquitination substrate protein for ubiquitin-dependent proteolysis. In a preferred embodiment, E3 comprises a ring finger protein and a Cullin. In a preferred embodiment, RING finger proteins include, but are not limited to, ROC1, ROC2 and APC11. In a preferred embodiment, Cullins include, but are not limited to, CUL1, CUL2, CUL3, CUL4A, CUL4B, CUL5 and APC2.

In a preferred embodiment, RING finger proteins include, but are not limited to, proteins having the amino acid sequence disclosed in ATCC accession numbers AAD30147 and AAD30146 and 6320196, incorporated herein by reference. In a more preferred embodiment, the ring finger protein has a sequence selected from the group consisting of that shown in FIG. 8, FIG. 9 and FIG. 10B.

In a preferred embodiment, Cullins include, but are not limited to, proteins having the amino acid sequences disclosed in ATCC accession numbers 4503161, AAC50544, AAC36681, 4503163, AAC51190, AAD23581, 4503165, AAC36304, AAC36682, AAD45191, AAC50548, Q13620, 4503167 and AAF05751, each of which is incorporated herein by reference. In addition, in the context of the invention, each of the RING finger proteins and Cullins encompass variants of the known or listed sequences, as described herein.

In a preferred embodiment, the Cullin has a sequence as shown in FIG. 11B or 12B.

These E3 proteins and variants may be made as described herein. In a preferred embodiment, nucleic acids used to make the RING finger proteins include, but are not limited to, those having the nucleic acid sequences disclosed in ATCC accession numbers AF142059, AF142060 and nucleic acids 433493 to 433990 of NC 001136. In a preferred embodiment, Cullins are made from nucleic acids including, but are not limited to, those having nucleic acid sequences disclosed in ATCC accession numbers NM 003592, U58087, AF062536, AF126404, NM 003591, U83410, NM 003590, AB014517, AF062537, AF064087, AF077188, U58091, NM 003478, X81882 and AF191337, each of which is incorporated herein by reference. As described above, variants of these sequences are also encompassed by the invention.

In a preferred embodiment, nucleic acid used to produce ROC2 comprises the sequence depicted in FIG. 12A. In a preferred embodiment, nucleic acid used to produce CUL5 comprises the sequence depicted in FIG. 13A. In a preferred embodiment, nucleic acid used to produce APC2 comprises the sequence depicted in FIG. 14A.

In a preferred embodiment, E3 comprises the RING finger protein/Cullin combination APC11/APC2. In another preferred embodiment, E3 comprises the RING finger protein/Cullin combination ROC1/CUL1. In yet preferred embodiment, E3 comprises the RING finger protein/Cullin combination ROC1/CUL2. In still another preferred embodiment, E3 comprises the RING finger protein/Cullin combination ROC2/CUL5. However, the skilled artisan will appreciate that any combination of E3 components may be produced and used in the invention described herein.

In an alternate embodiment, E3 comprises the ligase E3-alpha, E3A (E6-AP), HERC2, SMURF1, TRAF6, MDM2, Cbl, Sina/Siah, Itchy, IAP or NEDD-4. In this embodiment, the ligase has the amino acid sequence of that disclosed in ATCC accession number AAC39845, Q05086, CAA66655, CAA66654, CAA66656, AAD08657, NP_002383, XP_006284, AAC51970, XP_013050, BAB39389, Q00987, AAF08298 or P46934, each of which is incorporated herein by reference. As above, variants are also encompassed by the invention. Nucleic acids for making E3 for this embodiment include, but are not limited to, those having the sequences disclosed in ATCC accession numbers AF061556, XM006284, U76247, XM013050, X898032, X98031, X98033, AF071172, Z12020, AB056663, AF199364 and D42055 and variants thereof.

E3 may also comprise other components, such as SKP1 and F-box proteins. The amino acid and nucleic acid sequences for SKP1 are found in ATCC accession numbers AAC50241 and U33760, respectively. Many F-box proteins are known in the art and their amino acid and nucleic acid sequences are readily obtained by the skilled artisan from various published sources.

In a preferred embodiment, the E3 components are produced recombinantly, as described herein.

In a preferred embodiment, the E3 components are co-expressed in the same host cell. Co-expression may be achieved by transforming the cell with a vector comprising nucleic acids encoding two or more of the E3 components, or by transforming the host cell with separate vectors, each comprising a single component of the desired E3 protein complex. In a preferred embodiment, the RING finger protein and Cullin are expressed in a single host transfected with two vectors, each comprising nucleic acid encoding one or the other polypeptide, as described in further detail in the Examples.

In a preferred embodiment, E3 has a tag, which complex is referred to herein as "tag-E3". Preferably, the tag is attached to only one component of the E3. Preferred E3 tags include, but are not limited to, labels, partners of binding pairs and substrate binding elements. More preferably, the tag is a surface substrate binding molecule. Most preferably, the tag is a His-tag or GST-tag.

In an embodiment herein, ubiquitin and ubiquitination enzymes and their components are cloned and expressed as outlined below. Thus, probe or degenerate polymerase chain reaction (PCR) primer sequences may be used to find other related ubiquitination proteins from humans or other organisms. As will be appreciated by those in the art, particularly useful probe and/or PCR primer sequences include the unique areas of a nucleic acid sequence. As is generally known in the art, preferred PCR primers are from about 15 to about 35 nucleotides in length, with from about 20 to about 30 being preferred, and may contain inosine as needed. The conditions for the PCR reaction are well known in the art. It is therefore also understood that provided along with the sequences in the sequences cited herein are portions of those sequences, wherein unique portions of 15 nucleotides or more are particularly preferred. The skilled artisan can routinely synthesize or cut a nucleotide sequence to the desired length.

Once isolated from its natural source, e.g., contained within a plasmid or other vector or excised therefrom as a linear nucleic acid segment, the recombinant nucleic acid can be further-used as a probe to identify and isolate other nucleic acids. It can also be used as a "precursor" nucleic acid to make modified or variant nucleic acids and proteins.

Using the nucleic acids of the present invention which encode a protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. As another example, operably linked refers to DNA sequences linked so as to be contiguous, and, in the case of a secretory leader, contiguous and in reading fram. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used to express the protein; for example, transcriptional and translational regulatory nucleic acid sequences from *Bacillus* are preferably used to express the protein in *Bacillus*. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or insect cells for expression and in a procaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

A preferred expression vector system is a retroviral vector system such as is generally described in PCT/US97/01019 and PCT/US97/01048, both of which are hereby expressly incorporated by reference.

Proteins of the present invention are produced by culturing a host cell transformed with an expression vector containing nucleic acid encoding the protein, under the appropriate conditions to induce or cause expression of the protein. The conditions appropriate for protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archaebacteria, fungi, and insect and animal cells, including mammalian cells. Of particular interest are *Drosophila melanogaster* cells, *Pichia pastoris* and *P. methanolica*, *Saccharomyces cerevisiae* and other yeasts, *E. coli*, *Bacillus subtilis*, SF9 cells, SF21 cells, C129 cells, Saos-2 cells, Hi-5 cells, 293 cells, Neurospora, BHK, CHO, COS, and HeLa cells. Of greatest interest are *Pichia pastoris* and *P. methanolica*, *E. coli*, SF9 cells, SF21 cells and Hi-5 cells.

In a preferred embodiment, the proteins are expressed in mammalian cells. Mammalian expression systems are also known in the art, and include retroviral systems. A mammalian promoter is any DNA sequence capable of binding mammalian RNA polymerase and initiating the downstream (3') transcription of a coding sequence for a protein into MRNA. A promoter will have a transcription initiating region, which is usually placed proximal to the 5' end of the coding sequence, and a TATA box, using a located 25–30 base pairs upstream of the transcription initiation site. The TATA box is thought to direct RNA polymerase II to begin RNA synthesis at the correct site. A mammalian promoter will also contain an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature MRNA is formed by site-specific post-translational cleavage and polyadenylation. Examples of transcription terminator and polyadenylation signals include those derived form SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

In a preferred embodiment, proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of a protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan.

Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. coli*, the ribosome binding site is called the Shine-Delgarno (SD) sequence and includes an initiation codon and a sequence 3–9 nucleotides in length located 3–11 nucleotides upstream of the initiation codon.

The expression vector may also include a signal peptide sequence that provides for secretion of the protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria).

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis*, *E. coli*, *Streptococcus cremoris*, and *Streptococcus lividans*, among others.

The bacterial expression vectors are transformed into bacterial host cells using techniques well known in the art, such as calcium chloride treatment, electroporation, and others.

In one embodiment, proteins are produced in insect cells. Expression vectors for the transformation of insect cells, and in particular, baculovirus-based expression vectors, are well known in the art.

In a preferred embodiment, proteins are produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii P. methanolica* and *P. pastoris, Schizosaccharomyces pombe*, and *Yarrowia lipolytica*. Preferred promoter sequences for expression in yeast include the inducible GAL1,10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the neomycin phosphotransferase gene, which confers resistance to G418; and the CUP1 gene, which allows yeast to grow in the presence of copper ions.

The protein may also be made as a fusion protein, using techniques well known in the art. Thus, for example, the protein may be made as a fusion protein to increase expression, or for other reasons. For example, when the protein is a peptide, the nucleic acid encoding the peptide may be linked to other nucleic acid for expression purposes. Similarly, proteins of the invention can be linked to protein labels, such as green fluorescent protein (GFP), red fluorescent protein (RFP), blue fluorescent protein (BFP), yellow fluorescent protein (YFP), etc.

In a preferred embodiment, the protein is purified or isolated after expression. Proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the ubiquitin protein may be purified using a standard anti-ubiquitin antibody column. Ultrafiltration and diafiltration techniques, in conjunction with protein concentration, are also useful. For general guidance in suitable purification techniques, see Scopes, R., Protein Purification, Springer-Verlag, NY (1982). The degree of purification necessary will vary depending on the use of the protein. In some instances no purification will be necessary.

Once made, the compositions find use in a number of applications, including, but not limited to, screens for modulators of ubiquitination. By "modulator" is meant a compound which can increase or decrease ubiquitination. The skilled artisan will appreciate that modulators of ubiquitination may affect enzyme activity, enzyme interaction with the substrate, interaction between ubiquitin and the substrate, or a combination of these. A modulator that specifically affects ubiquitin ligase activity is a ubiquitin ligase modulator.

By "candidate", "candidate agent", "candidate modulator", "candidate ubiquitination modulator" or grammatical equivalents herein is meant any molecule, e.g. proteins (which herein includes proteins, polypeptides, and peptides), small organic or inorganic molecules, polysaccharides, polynucleotides, etc. which are to be tested for ubiquitination modulator activity. Candidate agents encompass numerous chemical classes. In a preferred embodiment, the candidate agents are organic molecules, particularly small organic molecules, comprising functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more chemical functional groups.

Candidate modulators are obtained from a wide variety of sources, as will be appreciated by those in the art, including libraries of synthetic or natural compounds. As will be appreciated by those in the art, the present invention provides a rapid and easy method for screening any library of candidate modulators, including the wide variety of known combinatorial chemistry-type libraries.

In a preferred embodiment, candidate modulators are synthetic compounds. Any number of techniques are available for the random and directed synthesis of a wide variety of organic compounds and biomolecules, including expression of randomized oligonucleotides. See for example WO 94/24314, hereby expressly incorporated by reference, which discusses methods for generating new compounds, including random chemistry methods as well as enzymatic methods. As described in WO 94/24314, one of the advantages of the present method is that it is not necessary to characterize the candidate modulator prior to the assay; only candidate modulators that increase or decease ubiquitin ligase activity need be identified. In addition, as is known in the art, coding tags using split synthesis reactions may be done, to essentially identify the chemical moieties tested.

Alternatively, a preferred embodiment utilizes libraries of natural compounds in the form of bacterial, fungal, plant and animal extracts that are available or readily produced.

Additionally, natural or synthetically produced libraries and compounds are readily modified through conventional chemical, physical and biochemical means. Known pharmacological agents may be subjected to directed or random chemical modifications, including enzymatic modifications, to produce structural analogs.

In a preferred embodiment, candidate modulators include proteins, nucleic acids, and chemical moieties.

In a preferred embodiment, the candidate modulator are proteins, as defined above. In a preferred embodiment, the candidate modulators are naturally occurring proteins or fragments of naturally occurring proteins. Thus, for example, cellular extracts containing proteins, or random or directed digests of proteinaceous cellular extracts, may be tested, as is more fully described below. In this way libraries of procaryotic and eucaryotic proteins may be made for screening against any number of ubiquitin ligase compositions. Particularly preferred in this embodiment are libraries of bacterial, fungal, viral, and mammalian proteins, with the latter being preferred, and human proteins being especially preferred.

In a preferred embodiment, the candidate modulators are peptides of from about 2 to about 50 amino acids, with from about 5 to about 30 amino acids being preferred, and from about 8 to about 20 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

The library should provide a sufficiently structurally diverse population of randomized agents to effect a probabilistically sufficient range of diversity to allow interaction with a particular ubiquitin ligase enzyme. Accordingly, an interaction library must be large enough so that at least one of its members will have a structure that interacts with a ubiquitin ligase enzyme. Although it is difficult to gauge the required absolute size of an interaction library, nature provides a hint with the immune response: a diversity of $10^7$–$10^8$ different antibodies provides at least one combination with sufficient affinity to interact with most potential antigens faced by an organism. Published in vitro selection techniques have also shown that a library size of $10^7$ to $10^8$ is sufficient to find structures with affinity for a target. A library of all combinations of a peptide 7 to 20 amino acids in length, such as generally proposed herein, has the potential to code for $20^7$ ($10^9$) to $20^{20}$. Thus, with libraries of $10^7$ to $10^8$ different molecules the present methods allow a "working" subset of a theoretically complete interaction library for 7 amino acids, and a subset of shapes for the $20^{20}$ library. Thus, in a preferred embodiment, at least $10^6$, preferably at least $10^7$, more preferably at least $10^8$ and most preferably at least $10^9$ different sequences are simultaneously analyzed in the subject methods. Preferred methods maximize library size and diversity.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, the bias is towards peptides or nucleic acids that interact with known classes of molecules. For example, when the candidate modulator is a peptide, it is known that much of intracellular signaling is carried out via short regions of polypeptides interacting with other polypeptides through small peptide domains. For instance, a short region from the HIV-1 envelope cytoplasmic domain has been previously shown to block the action of cellular calmodulin. Regions of the Fas cytoplasmic domain, which shows homology to the mastoparan toxin from Wasps, can be limited to a short peptide region with death-inducing apoptotic or G protein inducing functions. Magainin, a natural peptide derived from *Xenopus*, can have potent anti-tumor and anti-microbial activity. Short peptide fragments of a protein kinase C isozyme (βPKC), have been shown to block nuclear translocation of βPKC in *Xenopus* oocytes following stimulation. And, short SH-3 target peptides have been used as psuedosubstrates for specific binding to SH-3 proteins. This is of course a short list of available peptides with biological activity, as the literature is dense in this area. Thus, there is much precedent for the potential of small peptides to have activity on intracellular signaling cascades. In addition, agonists and antagonists of any number of molecules may be used as the basis of biased randomization of candidate modulators as well.

Thus, a number of molecules or protein domains are suitable as starting points for the generation of biased randomized candidate modulators. A large number of small molecule domains are known, that confer a common function, structure or affinity. In addition, as is appreciated in the art, areas of weak amino acid homology may have strong structural homology. A number of these molecules, domains, and/or corresponding consensus sequences, are known, including, but are not limited to, SH-2 domains, SH-3 domains, Pleckstrin, death domains, protease cleavage/recognition sites, enzyme inhibitors, enzyme substrates, Traf, etc.

In a preferred embodiment, the candidate modulators are nucleic acids. With reference to candidate modulators, by "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowski et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169–176). Several nucleic acid analogs are described in Rawls, C & E News Jun. 2, 1997 page 35. All of these references are hereby expressly incorporated by reference. These modifications of the ribose-phosphate backbone may be done to facilitate the addition of additional moieties such as labels, or to increase the stability and half-life of such molecules in physiological environments.

As will be appreciated by those in the art, all of these nucleic acid analogs may find use in the present invention. In addition, mixtures of naturally occurring nucleic acids and analogs can be made. Alternatively, mixtures of different nucleic acid analogs, and mixtures of naturally occurring nucleic acids and analogs may be made. Particularly preferred are peptide nucleic acids (PNA) which includes peptide nucleic acid analogs. These backbones are substantially non-ionic under neutral conditions, in contrast to the highly charged phosphodiester backbone of naturally occurring nucleic acids.

The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc. As used herein, the term "nucleoside" includes nucleotides and nucleoside and nucleotide analogs, and modified nucleosides such as amino modified nucleosides. In addition, "nucleoside" includes non-naturally occurring analog structures. Thus for example the individual units of a peptide nucleic acid, each containing a base, are referred to herein as a nucleoside.

As described above generally for proteins, nucleic acid candidate modulator may be naturally occurring nucleic acids, random nucleic acids, or "biased" random nucleic acids. For example, digests of procaryotic or eucaryotic genomes may be used as is outlined above for proteins. Where the ultimate expression product is a nucleic acid, at least 10, preferably at least 12, more preferably at least 15, most preferably at least 21 nucleotide positions need to be randomized, with more preferable if the randomization is less than perfect. Similarly, at least 5, preferably at least 6, more preferably at least 7 amino acid positions need to be randomized; again, more are preferable if the randomization is less than perfect.

In a preferred embodiment, the candidate modulators are organic moieties. In this embodiment, as is generally described in WO 94/24314, candidate agents are synthesized from a series of substrates that can be chemically modified. "Chemically modified" herein includes traditional chemical reactions as well as enzymatic reactions. These substrates generally include, but are not limited to, alkyl groups (including alkanes, alkenes, alkynes and heteroalkyl), aryl groups (including arenes and heteroaryl), alcohols, ethers, amines, aldehydes, ketones, acids, esters, amides, cyclic compounds, heterocyclic compounds (including purines, pyrimidines, benzodiazepins, beta-lactams, tetracylines, cephalosporins, and carbohydrates), steroids (including estrogens, androgens, cortisone, ecodysone, etc.), alkaloids (including ergots, vinca, curare, pyrollizdine, and mitomycines), organometallic compounds, hetero-atom bearing compounds, amino acids, and nucleosides. Chemical (including enzymatic) reactions may be done on the moieties to form new substrates or candidate agents which can then be tested using the present invention.

As will be appreciated by those in the art, it is possible to screen more than one type of candidate modulator at a time. Thus, the library of candidate modulators used may include only one type of agent (i.e. peptides), or multiple types (peptides and organic agents). The assay of several candidates at one time is further discussed below.

The present invention provides methods and compositions comprising combining several components. In a preferred embodiment, a preferred combination is tag-ubiquitin, E1, E2, and E3. Preferably the tag is a label, a partner of a binding pair, or a substrate binding molecule. More preferably, the tag is a fluorescent label or a binding pair partner. In a preferred embodiment, the tag is a binding pair partner and the ubiquitin is labeled by indirect labeling. In the indirect labeling embodiment, preferably the label is a fluorescent label or a label enzyme. In an embodiment comprising a label enzyme, preferably the substrate for that enzyme produces a fluorescent product. In a preferred embodiment, the label enzyme substrate is luminol. In a preferred embodiment, combining specifically excludes combining the components with a target protein.

In another preferred embodiment, a preferred combination is Tag1-ubiquitin, tag2-ubiquitin, E1, E2 and E3. Preferably, tag1 and tag2 are labels, preferably fluorescent labels, most preferably tag1 and tag2 constitute a FRET pair.

In a preferred embodiment, a preferred combination is tag1-ubiquitin, E1, E2 and tag2-E3. Preferably, tag1 is a label, a partner of a binding pair, or a substrate binding molecule and tag2 is a different label, partner of a binding pair, or substrate binding molecule. More preferably, tag1 is a fluorescent label or a member of a binding pair. When tag1 is a member of a binding pair, preferably tag1 is indirectly labeled. Still more preferably, tag-1 is indirectly labeled with a label enzyme. Preferably the label enzyme substrate used to reveal the presence of the enzyme produces a fluorescent product, and more preferably is luminol. In the presently described combination, preferably tag2 is a surface substrate binding element, more preferably a His-tag.

In a preferred embodiment, a preferred combination is tag1-ubiquitin, E1 and tag2-E2. In this embodiment, preferably, tag1 is a label, a partner of a binding pair, or a substrate binding molecule and tag2 is a different label, partner of a binding pair, or substrate binding molecule. More preferably, tag-1 is a label or a member of a binding pair. When tag1 is a member of a binding pair, preferably tag1 is indirectly labeled. In a preferred embodiment, the tag1 label (direct or indirect) is a fluorescent label or a label enzyme. When the tag1 label (direct or indirect) is a label enzyme, preferably the reaction substrate used to reveal the presence of the enzyme produces a fluorescent product, and more preferably is luminol. In the presently described combination, preferably tag2 is a substrate binding element, more preferably a His-tag.

In a preferred embodiment, the compositions of the invention do not comprise a target protein. In this embodiment, ubiquitin is the sole ubiquitination substrate, as discussed above. This embodiment stands in contrast to previous ubiquitination enzyme assays, which required addition of a target protein as part of the composition. Because the different combinations of E3 and E2 and combinations of E3 subunits are specific to particular target proteins, the present assays are much more versatile, allowing any variation of such combinations without first identifying the specific target protein to which the combination is directed.

The components of the present compositions may be combined in varying amounts. In a preferred embodiment, ubiquitin is combined at a final concentration of from 20 to 200 ng per 100 µl reaction solution, most preferable at about 100 ng per 100 µl reaction solution.

In a preferred embodiment, E1 is combined at a final concentration of from 1 to 50 ng per 100 µl reaction solution, more preferably from 1 ng to 20 ng per 100 µl reaction solution, most preferably from 5 ng to 10 ng per 100 µl reaction solution.

In a preferred embodiment, E2 is combined at a final concentration of 10 to 100 ng per 100 µl reaction solution, more preferably 10–50 ng per 100 µl reaction solution.

In a preferred embodiment, E3 is combined at a final concentration of from 1 ng to 500 ng per 100 µl reaction solution, more preferably from 50 to 400 ng per 100 µl reaction solution, still more preferably from 100 to 300 ng per 100 µl reaction solution, most preferably about 100 ng per 100 µl reaction solution.

The components of the invention are combined under reaction conditions that favor ubiquitin ligase activity and/or ubiquitination activity. Generally, this will be physiological conditions. Incubations may be performed at any temperature which facilitates optimal activity, typically between 4 and 40° C. Incubation periods are selected for optimum activity, but may also be optimized to facilitate rapid high through put screening. Typically between 0.5 and 1.5 hours will be sufficient.

A variety of other reagents may be included in the compositions. These include reagents like salts, solvents, buffers, neutral proteins, e.g. albumin, detergents, etc. which may be used to facilitate optimal ubiquitination enzyme activity and/or reduce non-specific or background interactions. Also reagents that otherwise improve the efficiency of the assay, such as protease inhibitors, nuclease inhibitors, anti-microbial agents, etc., may be used. The compositions will also preferably include adenosine tri-phosphate (ATP).

The mixture of components may be added in any order that promotes ubiquitin ligase activity or optimizes identification of candidate modulator effects. In a preferred embodiment, ubiquitin is provided in a reaction buffer solution, followed by addition of the ubiquitination enzymes. In an alternate preferred embodiment, ubiquitin is provided in a reaction buffer solution, a candidate modulator is then added, followed by addition of the ubiquitination enzymes.

Once combined, preferred methods of the invention comprise measuring the amount of ubiquitin bound to E3. In an alternate preferred embodiment in which the combination lacks E3, preferred methods of the invention comprise measuring the amount of ubiquitin bound to E2. As will be understood by one of ordinary skill in the art, the mode of measuring will depend on the specific tag attached to the ubiquitin. As will also be apparent to the skilled artisan, the amount of ubiquitin bound will encompass not only the particular ubiquitin protein bound directly to the ubiquitination enzyme, but also the ubiquitin proteins bound to that particular ubiquitin in a polyubiquitin chain.

In a preferred embodiment, the tag attached to the ubiquitin is a fluorescent label. In a preferred embodiment, the tag attached to ubiquitin is an enzyme label or a binding pair member which is indirectly labeled with an enzyme label. In this latter preferred embodiment, the enzyme label substrate produces a fluorescent reaction product. In these preferred embodiments, the amount of ubiquitin bound is measured by luminescence.

As used herein, "luminescence" or "fluorescent emission" means photon emission from a fluorescent label. In an embodiment where FRET pairs are used, fluorescence measurements may be taken continuously or at time-points during the ligation reaction. Equipment for such measurement is commercially available and easily used by one of ordinary skill in the art to make such a measurement.

Other modes of measuring bound ubiquitin are well known in the art and easily identified by the skilled artisan for each of the labels described herein. For instance, radioisotope labeling may be measured by scintillation counting, or by densitometry after exposure to a photographic emulsion, or by using a device such as a PhosphorImager. Likewise, densitometry may be used to measure bound ubiquitin following a reaction with an enzyme label substrate that produces an opaque product when an enzyme label is used.

In preferred methods of the present invention, E3 is bound to a surface substrate. This may be done directly, as described above for the binding of a label to ubiquitin. This may also be accomplished using tag-E3, wherein the tag is a surface substrate binding molecule.

In another preferred embodiment of the invention, E2 is bound to a surface substrate in the absence of E3. This may be done directly, as described above for the binding of a label to ubiquitin. This may also be accomplished using tag-E2, wherein the tag is a surface substrate binding molecule.

In the two preferred embodiments described immediately above, E3 and E2 are in the form of tag-E3 and tag-E2, respectively, and are bound to a surface substrate via a surface substrate binding molecule tag. In general, any substrate binding molecule can be used. In a preferred embodiment, the tag is a His-tag and the surface substrate is nickel. In a preferred embodiment, the nickel surface substrate is present on the surface of the wells of a multi-well plate, such as a 96 well plate. Such multi-well plates are commercially available. The binding of the enzyme to a surface substrate facilitates the separation of bound ubiquitin from unbound ubiquitin. In the present embodiment, the unbound ubiquitin is easily washed from the receptacle following the ligation reaction. As will be appreciated by those of skill in the art, the use of any surface substrate binding element and receptacle having the surface substrate to which it binds will be effective for facilitating the separation of bound and unbound ubiquitin.

In an alternative embodiment, E3 or E2 is bound, directly or via a substrate binding element, to a bead. Following ligation, the beads may be separated from the unbound ubiquitin and the bound ubiquitin measured. In a preferred embodiment, E3 or E2 is bound to beads and the composition used includes tag-ubiquitin wherein tag is a fluorescent label. In this embodiment, the beads with bound ubiquitin may be separated using a fluorescence-activated cell sorting (FACS) machine. Methods for such use are described in U.S. patent application Ser. No. 09/047,119, which is hereby incorporated in its entirety. The amount of bound ubiquitin can then be measured.

In another embodiment, none of the ubiquitination enzymes is bound to a substrate. Preferably in this embodiment, the composition comprises tag1-ubiquitin, tag2-ubiquitin, E1, E2 and E3. Preferably, tag1 and tag2 are labels, preferably fluorescent labels, most preferably tag1 and tag2 constitute a FRET pair. In this embodiment, ubiquitination is measured by measuring the fluorescent emission spectrum. This measuring may be continuous or at one or more times following the combination of the components. Alteration in the fluorescent emission spectrum of the combination as compared with unligated ubiquitin indicates the amount of ubiquitination. The skilled artisan will appreciate that in this embodiment, alteration in the fluorescent emission spectrum results from ubiquitin bearing different members of the FRET pair being brought into close proximity, either through the formation of poly-ubiquitin and/or by binding nearby locations on a protein, preferably a target protein.

In a preferred embodiment, the compositions of the invention are used to identify ubiquitination modulators. In this embodiment, the composition includes a candidate modulator. In a preferred embodiment, the measured amount and/or rate of tag-ubiquitin binding to E3 is compared with the that when the candidate modulator is absent from the composition, whereby the presence or absence of the modulators effect on ubiquitin ligase activity is determined. In this embodiment, whether the modulator enhances or inhibits ubiquitination is also determined.

In a preferred embodiment, the composition of the invention containing a candidate modulator lacks E3 and the amount and/or rate of ubiquitin binding to E2 is measured. This embodiment may also comprise the step of comparing the amount and/or rate of ubiquitin binding to E2 in a composition lacking both E3 and the candidate modulator, whereby the modulatory activity of the candidate on ubiquitination enzymes other than E3 is determined. In a preferred embodiment, the percentage difference in the amount of ubiquitin bound to E2 in the presence and absence of the candidate modulator is compared with the percentage difference in the amount bound to E3 in the presence and absence of candidate modulator, whereby the point of effect of the candidate modulator in the enzyme cascade is determined. That is, it is determined whether the candidate modulator affects E3 ubiquitin ligase activity or it affects E1 ubiquitin activating activity and/or E2 ubiquitin conjugating activity.

In another preferred embodiment, the compositions of the invention are used to identify ubiquitination modulators. In this embodiment, the composition includes a candidate modulator. In a preferred embodiment, where tag1 and tag2 constitute a FRET pair, the measured amount and/or rate of tag1-ubiquitin and tag2-ubiquitin binding to a substrate protein (as poly-ubiquitin and/or ubiquitin bound to a target protein) is compared with the amount or rate of such binding in the absence of the candidate modulator, whereby the presence or absence of the modulator's effect on ubiquitin ligase activity is determined. In this embodiment, whether the modulator enhances or inhibits ubiquitination is also determined.

In a preferred embodiment, multiple assays are performed simultaneously in a high throughput screening system. In this embodiment, multiple assays may be performed in multiple receptacles, such as the wells of a 96 well plate or other multi-well plate. As will be appreciated by one of skill in the art, such a system may be applied to the assay of multiple candidate modulators and/or multiple combination of E3 components and/or E2–E3 pairings. In a preferred embodiment, the present invention is used in a high-throughput screening system for determining the ubiquitin ligase activity of different E2–E3 pairings and/or different E3 component combinations. In an alternate preferred embodiment, the present invention is used in a high throughput screening system for simultaneously testing the effect of individual candidate modulators.

In another aspect, the invention provides a method of assaying for ubiquitination activity or ubiquitination enzyme activity in a mixture. Ubiquitin is introduced into a cell or mixture of protein, preferably a cell lysate, under conditions in which ubiquitination can take place. In this embodiment, the ubiquitin is in the form of tag1-ubiquitin and tag2-ubiquitin, wherein tag1 and tag2 constitute a FRET pair or tag1 is a fluorescent label and tag2 is a quencher of tag1. Fluorescent emission spectrum is measured as an indication of whether ubiquitination activity is present in the mixture or cell. In a preferred embodiment, the ubiquitin also comprises a member of a binding pair, such as FLAG (DYKDDDDK; SEQ ID NO:16). In this latter embodiment, components involved in ubiquitination can be isolated from the mixture using any one of a number of affinity-based separation means such as fluorescent beads coated with anti-FLAG (DYKDDDDK; SEQ ID NO:16) antibody or amino precipitation using anti-FLAG (DYKDDDDK; SEQ ID NO:16) antibodies, or using anti-FLAG (DYKDDDDK; SEQ ID NO:16) antibody attached to a solid support. Other means of separating ubiquitin bound components of the cell or mixture will be readily apparent to the skilled artisan. Ubiquitin bound components so separated in this method may include E3 and target protein. The skilled artisan will appreciate that separation of-these components for individual identification or subsequent investigation may be obtained by several means well known in the art, such as by HPLC or electrophoresis.

It is understood by the skilled artisan that the steps of the assays provided herein can vary in order. It is also understood, however, that while various options (of compounds, properties selected or order of steps) are provided herein, the options are also each provided individually, and can each be individually segregated from the other options provided herein. Moreover, steps which are obvious and known in the art that will increase the sensitivity of the assay are intended to be within the scope of this invention. For example, there may be additionally washing steps, blocking steps, etc.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are expressly incorporated by reference in their entirety.

EXAMPLES

Example 1

Production of E2, E3 and Ubiquitin

E2 Production

The open reading frame of E2 (Ubc5C) was amplified by PCR and cloned into the pGex-6p-1 *E. Coli.* expression vector (Amersham Pharmacia) as BglII-EcoRI fragments, with N-terminus in frame fused to the GST-tag.

Materials and Methods

Plasmid is transformed in BL21 DE3 competent *E.coli* (Stratagene, cat # 230132). Cells are grown at 37° C. in TB+100 ug/ml ampicillin and 0.4% glucose to an OD600 of about 0.6, induced with addition of 320 uM IPTG and allowed to grow for another 3 h before harvest. The pellets are washed once with cold PBS, then resuspended in about 6 volumes of lysis buffer (20 mM Tris, 10% glycerol, 0.5 M Nacl, 2.5 mM EDTA, 1 mM TCEP plus Complete -EDTA Free Protease inhibitor tablets, 1 tablet/25 ml of resuspended cells, pH 8.0). The suspension is homogenized and sonicated 3×30 sec. NP40, then added to a final concentration of 0.5% and the tubes are rocked for 30 min at 4° C. Following centrifugation at 11000 rpm for 25 to 30 min, the supernatant is incubated with Glutathione Sepharose 4B (Amersham, cat # 17-0756-01) at a ratio of 1 ml of beads per 100 ml of original culture volume for 1 to 2 hours at 4° C. with gentle rocking. The beads are pelleted and washed once with 10 bed volumes of the lysis buffer, then twice with 10 bed volumes of Prescission Protease buffer (50 mM Tris-HCL, 150 mM NaCl, 1 mM EDTA, 1 mM DTT, 0.1% NP-40, pH 7.0.). Prescission Protease (Amersham, product # 27-0843) is added at a ratio of 80 ul (160 Units) per ml of GST resin, and allowed to incubate for 4 h at 4° C. The supernatant containing the cleaved E2 protein is collected, and the resin is washed twice with one bed volume of Prescission buffer. All three fractions are analyzed by SDS-PAGE and pooled when appropriate.

Ubiquitin Production

Ubiquitin was cloned into the pFlag-Mac Expression Vector (Sigma) as a HindIII-EcoRI fragment by PCR. This results in expression of amino-terminal FLAG (DYKDDDDK; SEQ ID NO:16) fusion ubiquitin in *E. coli.*

Materials and Methods

The induction of protein expression and cell lysis is similar to the above GST-E2 preparation, except that the supernatant is loaded over a FLAG (DYKDDDDK; SEQ ID NO:16)-affinity resin (VWR, cat #1B13020) at a ratio of 15ml of beads per 1 L of original culture. The resin is then washed with 10 bed volumes of lysis buffer. The protein is eluted from the column with: 100 mM Acetic acid, 10% glycerol, 200 mM NaCl, 2.5 mM EDTA, 0.1% NP-40, pH 3.5. The elutions are collected as 1 bed volume fractions into tubes that contain $\frac{1}{10}^{th}$ volume of 2 M Tris, 80 mM B-ME, pH 9.0 to neutralize the pH. The elution fractions are analyzed by SDS-PAGE and the appropriate fractions are pooled and dialyzed against 400 volumes of 20 mM Tris, 10% glycerol, 200 mM NaCl, 2.5 mM EDTA, pH 8.0.

Production of E3

Coding sequences for E3 complex were also amplified by PCR and baculoviruses were generated using the Bac-to-Bac system (GibcoBRL). E3 contains two subunits, which are expressed by co-infection of the two baculovirus in the same Hi-5 insect cells. One of the subunit is His-tagged, with the other associating subunit untagged.

The detail procedure was done following the Bac to Bac Baculovirus Expression system by GibcoBRL. For example, ROC1 was cloned into the pFastBacHtb vector with a N-terminal His6 (SEQ ID NO:21) tag, while CUL1 was inserted into the pFastBac1 vector without any fusing tag. After transposition and Bacmid DNA transfection into SF-9 cells, Baculoviruses were harvested, amplified, and used to co-infect Hi-S cells for protein expression.

Materials and Methods

Cells are harvested, washed once with cold PBS, and resuspended in about 6 volumes of lysis buffer (20 mM Tris, 20% glycerol, 0.5 M Nacl, 15 mM imidazole, 1 mM TCEP plus Complete -EDTA Free Protease inhibitor tablets, 1 tablet/25 ml of resuspended cells, pH 8.0.). The suspension is then sonicated 3×30 sec, followed by addition of NP40 to a final concentration of 0.5% and incubation for 30 min at 4° C. The lysate is then centrifuged and the supernatant is incubated with pre-equilibrated (lysis buffer+NP40) Ni-NTA Agarose beads (Qiagen, cat # 1000632) for 1 to 2 hrs. The pelleted beads are washed 2 times with lysis buffer, resuspended in 1 to 2 volumes of lysis buffer and transferred to a disposable column for elution. Elution is accomplished using 5×1-bed volume aliquots of Lysis buffer+250 mM imidazole. Elution fractions are analyzed by SDS-PAGE and appropriate fractions are pooled. The elution pool is then desalted using either a desalting column or a centrifugal concentration device (more often used for large volumes.) When using centrifugal devices, the eluted pool is diluted 1:1 with lysis buffer that has no imidazole and spun at the appropriate speed until the volume is reduced by half. At this point an equal volume of fresh buffer is added and the device is respun. This is done a total of four times resulting in a 32 fold exchange.

Example 2

Ubiquitin Conjugation Assay

Ubiquitin conjugating activity of E1 +E2 was measured using the following protocol with FLAG (DYKDDDDK; SEQ ID NO:16)-ubiquitin, purified from E. coli, and the E2 Ubch5c, purified as His-Ubch5c from E. coli.

Materials and Methods

The following procedures were used for assays measuring ubiquitin conjugation. The wells of Nickel-substrate 96-well plates (Pierce Chemical) are blocked with 100 μl of 1% casein/phosphate buffered saline (PBS) for 1 hour at room temperature, then washed with 200 μl of PBST (0.1% Tween-20 in PBS)3 times. To each well is added the following FLAG-ubiquitin (SEQ ID NO:14) (see above) reaction solution:

Final Concentration
    62.5 mM Tris pH 7.5
    6.25 mM $MgCl_2$
    0.75 mM DTT
    2.5 mM ATP
    2.5 mM NaF
    12.5 nM Okadaic acid
    100 ng FLAG-ubiquitin (SEQ ID NO:14) (made as described above).

The buffer solution is brought to a final volume of 80 μl with Millipore-filtered water, followed by the addition of 10 μl of DMSO.

To the above solution is then added 10 μl of E1,His-E2 in 20 mM Tris buffer, pH 7.5, and 5% glycerol. His-E2 is made as described above. E1 is obtained commercially (Affiniti Research Products, Exeter, U.K.). The following amounts of each enzyme are used for these assays: 5 ng/well of E1; 25 nl/well E2. The reaction is then allowed to proceed at room temperature for 1 hour.

Following the ubiquitin conjugation reaction, the wells are washed with 200 μl of PBST3 times. For measurement of the enzyme-bound ubiquitin, 100 μl of Mouse anti-FLAG (DYKDDDDK; SEQ ID NO:16) (1:10,000) and anti-Mouse Ig-HRP (1:15,000) in PBST are added to each well and allowed to incubate at room temperature for 1 hour. The wells are then washed with 200 μl of PBST 3 times, followed by the addition of 100 μl of luminol substrate (⅕ dilution). Luminescence for each well is then measured using a fluorimeter.

Results

Ubiquitin Activating and Conjugating Activity

FIG. 1A shows the luminescence measured for E1 alone and for E1+his-E2, as described above.

Example 3

Ubiquitin Ligase Assay

Ubiquitin ligase activity of E1 +E2+E3 was measured using the following protocol with FLAG-ubiquitin (SEQ ID NO:14), purified from E. coli, the E2 UbchSc, purified as GST-UbchSc from E. coli with the GST tag removed, and the E3 His-ROC/Cul1 complex purified from Hi-5 cells by Baculovirus co-infection. This assay was also used to show the effects of candidate modulators on ubiquitin ligase activity.

Materials and Methods

The wells of Nickel-substrate 96-well plates (Pierce Chemical) are blocked with 100 μl of 1% casein/phosphate buffered saline (PBS) for 1 hour at room temperature, then washed with 200 μl of PBST (0.1% Tween-20 in PBS) 3 times. To each well is added the following FLAG-ubiquitin (SEQ ID NO:14) (see above) reaction solution:

Final Concentration
    62.5 mM Tris pH7.5
    6.25 mM MgCl2
    0.75 mM DTT
    2.5 mM ATP
    2.5 mM NaF
    12.5 nM Okadaic acid
    100 ng FLAG-ubiquitin (SEQ ID NO:14) (made as described above).

The buffer solution is brought to a final volume of 80 μl with Millipore-filtered water.

For assays directed to identifying modulators of ubiquitin ligase activity, 10 μl of a candidate modulator compound in DMSO is then added to the solution. If no candidate modulator is added, 10 μl of DMSO is added to the solution.

To the above solution is then added 10 μl of ubiquitination enzymes in 20 mM Tris buffer, pH 7.5, and 5% glycerol. F2-Ubch5c and E3-HisROC1/Cul1 are made as described above. E1 is obtained commercially (Affiniti Research Products, Exeter, U.K.). The following amounts of each enzyme are used for these assays: 5 ng/well of E1; 25 nl/well E2; and 100 ng/well His-E3. The reaction is then allowed to proceed at room temperature for 1 hour.

Following the ubiquitination reaction, the wells are washed with 200 μl of PBST 3 times. For measurement of the enzyme-bound ubiquitin, 100 μl of Mouse anti-FLAG (DYKDDDDK; SEQ ID NO:16) (1:10,000) and anti-Mouse Ig HRP (1:15,000) in PBST are added to each well and allowed to incubate at room temperature for 1 hour. The wells are then washed with 200 μl of PBST 3 times, followed by the addition of 100 μl of luminol substrate (⅕ dilution). Luminescence for each well is then measured using a fluorimeter.

Results

Ubiquitin Ligase Activity

FIG. 1 shows the luminescence measured for several different combinations of ubiquitination enzymes. In these experiments, only E3 was in the form His-E3. The luminescence measurements show that the assay specifically measures the activity of the entire ubiquitination enzyme cascade, which requires the presence of all three ubiquitination enzymes in the reaction.

Variations of Composition Components

Figure 2:
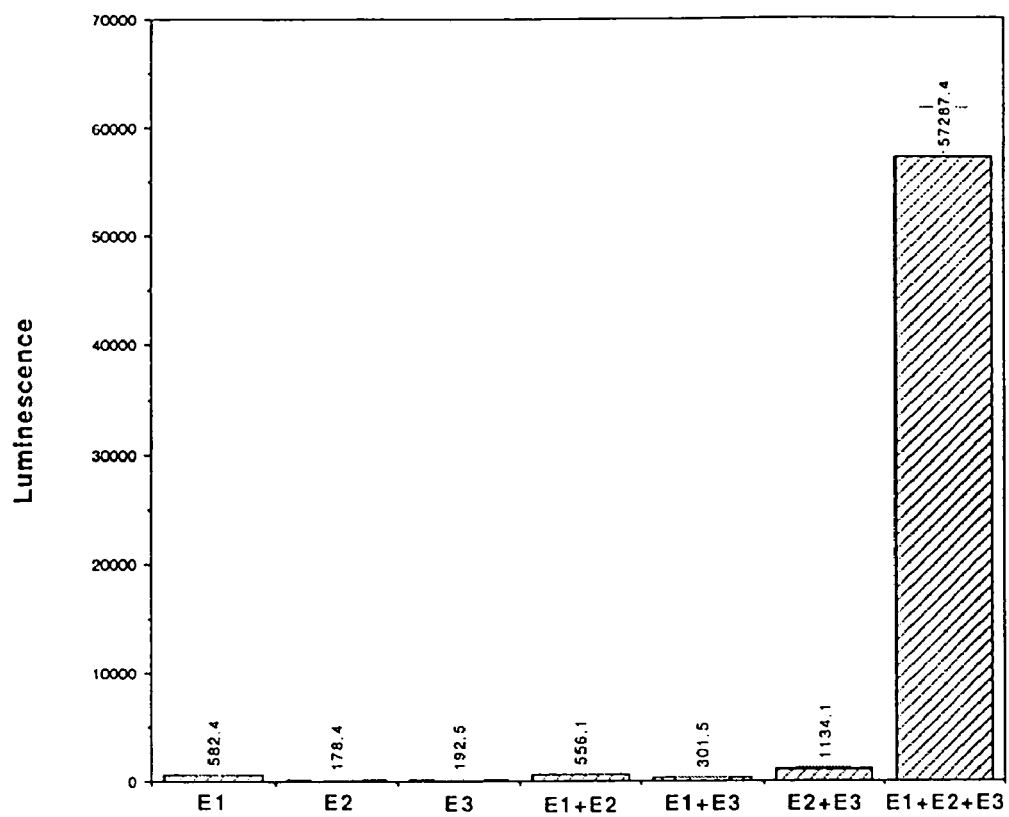
FIG. 2 shows the relative amounts of ubiquitin ligase activity resulting from various combinations of ubiquitination enzymes. In these experiments, E3 comprises the RING finger protein ROC1 and the Cullin Cul1.

FIG. 2A shows the relative effect of varying the amount of E1 on ubiquitin ligase activity in the above procedure, in presence and absence of DMSO. The addition of about 10 ng per 100 μl reaction solution provides maximum ubiquitin ligase activity with the other components of the composition kept as detailed above. The presence of DMSO does not significantly affect the activity of the ubiquitination enzymes.

The relative effect of varying E3 and ubiquitin concentration of the reaction composition is shown in FIG. 2B. Generally speaking, maximum ubiquitin ligase activity was obtained with 200 to 300 ng per 100 µl of E3 at each concentration of ubiquitin, while increasing ubiquitin concentration generally increased ubiquitin ligase activity at each concentration of E3.

Figure 3A:
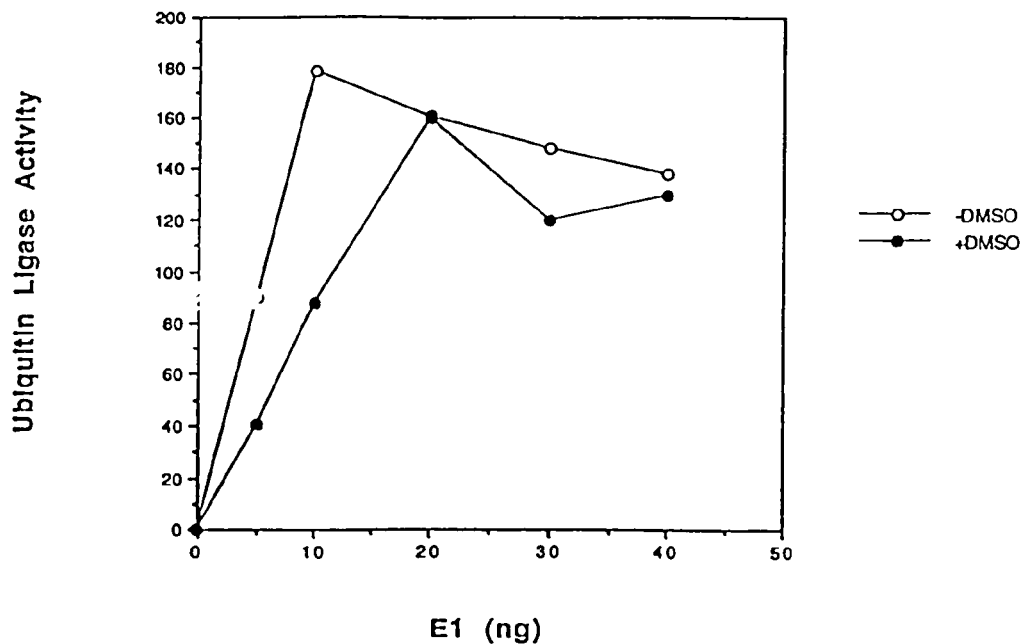
FIG. 3A shows relative ubiquitin ligase activity using varying amounts of E1 in the presence and absence of DMSO.
Figure 3B:
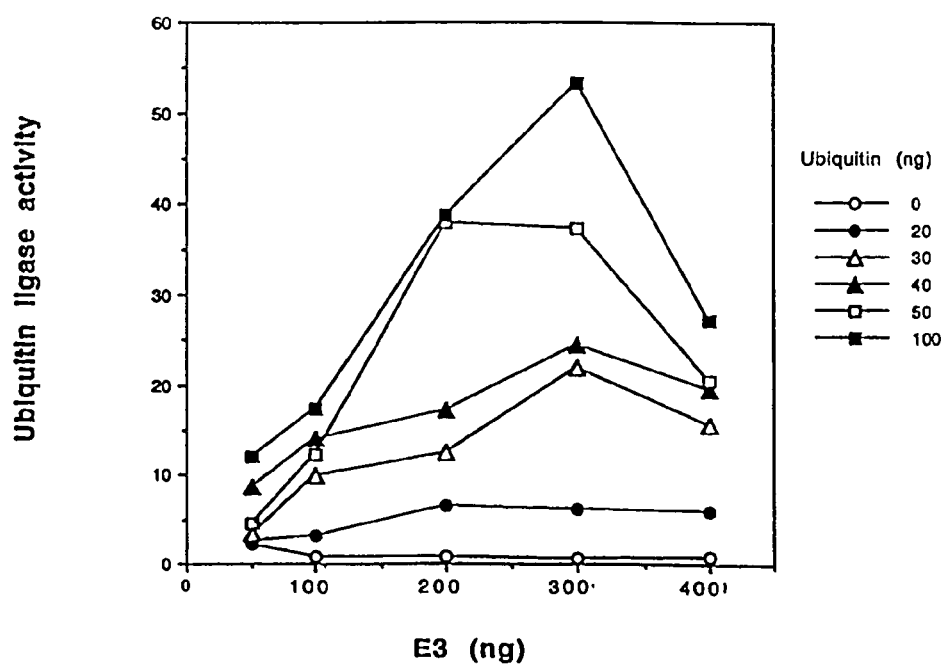
FIG. 3B shows relative ubiquitin ligase activity using varying amounts of ubiquitin and E3.

It was also found that blocking of the wells with 1% casein improved the signal to noise ratio over either no blocking or blocking with 5% bovine serum albumen (BSA). Background was determined after combining all of the components as above except His-E3 and measuring the resulting fluorescence after pre-treating the wells with 5% BSA, 1% casein or nothing. Results are shown in FIG. 3.

Identification of Modulators of Ubiquitin Ligase Activity

Figure 4:
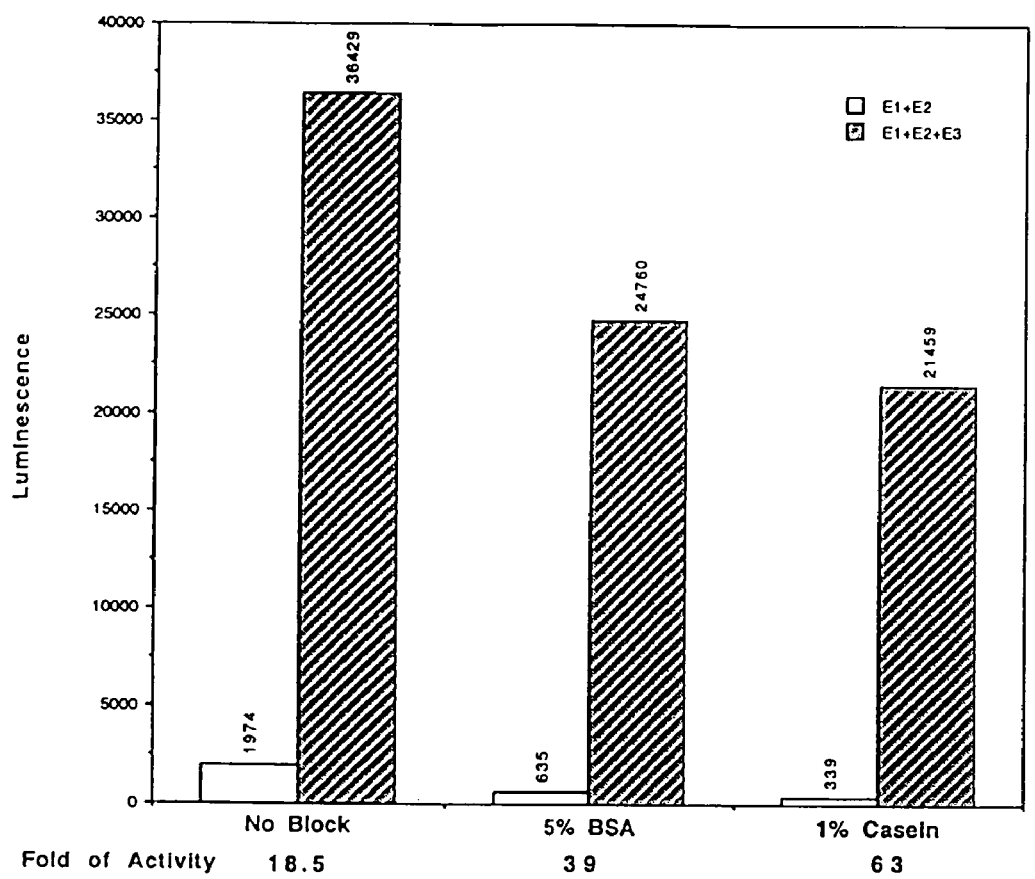
FIG. 4 shows the signal to noise ratio of fluorescent label in a ubiquitin ligase activity assay utilizing FLAG-ubiquitin (SEQ ID NO:14) and an anti-FLAG (DYKDDDDK; SEQ ID NO:16)/anti-mouse antibody conjugated to HRP and Luminol fluorescent HRP substrate. The signal was measured from a reaction composition comprising E1, E2 and E3, which E3 specifically bound the reaction receptacle surface substrate. The background was measured as the amount of fluorescence present after performing the assay in the absence of E3.

To show that the assay is useful for identifying modulators of ubiquitin ligase activity, several candidate modulators were combined at varying concentrations with the assay components as described above. FIG. 4 shows the results from two identified modulators of ubiquitin ligase activity. The modulators decreased ubiquitin ligase activity in a dose-dependent fashion for ubiquitination enzyme compositions comprising either ROC1/Cul1 or ROC2/Cul5 as the E3 component.

Figure 5A:
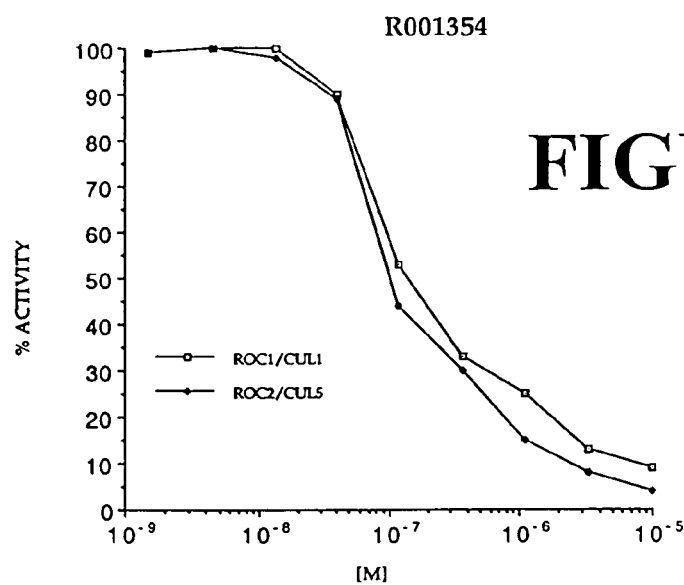
FIG. 5A shows a concentration-dependent reduction in ubiquitin ligase activity in assays comprising either ROC1/Cul1 or ROC2/Cul5 as the components of the E3 ubiquitin ligase.
Figure 5B:
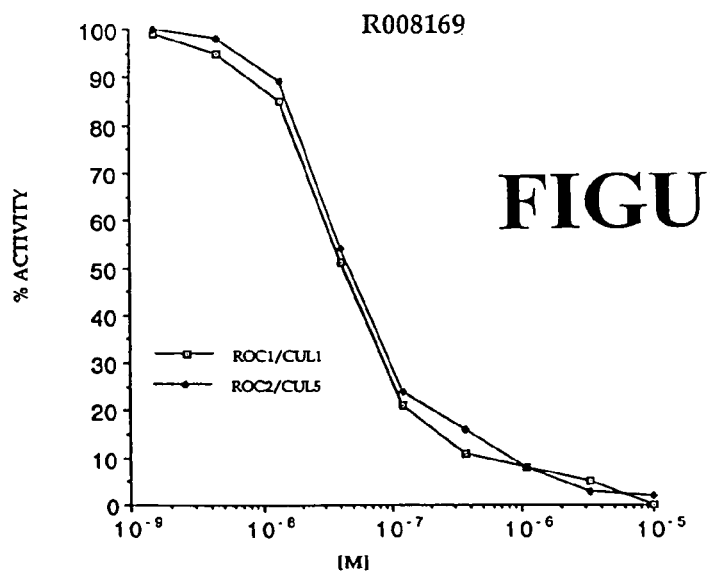
FIG. 5B shows a slightly different pattern of concentration-dependent reduction of ubiquitin ligase activity for another modulator.

Comparison of the effect of ubiquitin ligase activity modulators on reaction compositions, as described above, either containing E1, E2 and His-E3 or containing E1, His-E2 and lacking E3 shows whether the modulator affects E3 or an enzyme other than E3. In FIG. 5A, the identified modulator decreases ubiquitin ligase activity in the presence of E3, but does not alter activity in the absence of E3, showing that the modulator has a specific effect on E3 ligase activity. In contrast, results shown in FIG. 5B for another modulator reveals that this compound reduces activity whether or not E3 is present, showing that this modulator affects a member of the ubiquitination enzyme cascade other than E3.

Example 4

FRET Analysis of Ligated Ubiquitin

Ubiquitin was prepared, labeled with either EDANS or fluorescein, and the fluorescence of each of these labels and their interaction as a FRET pair was measured to show binding of the labeled ubiquitin to E3 and FRET activity in the bound ubiquitin.

Materials and Methods

Ubiquitin were produced incorporating Cys residues into the FLAG-ubiquitin (SEQ ID NO:14) sequence by site-directed mutagenesis using either the primer

5'-CCCCCCAAGCTTTGCATGCA-GATTTTCGTGAAGACCCTGACC-3'(SEQ ID NO:19)

to produce Flag-Cys-ubiquitin (SEQ ID NO:15), or the primer

5'-CCCCCCAAGCTTGCGTGCATGCA-GATTTTCGTGAAGACCCTGACC-3'(SEQ ID NO:20)

to produce FLAG-Ala-Cys-ubiquitin (SEQ ID NO:18). Protein was expressed and purified as described above.

Either fluoresceine 5-maleimide (peak emission at 515 nm) or 1,5-iodacetamide EDANS (IAEDANS; peak emission at 490 nm) was reacted with the thiol group on the cysteine of the ubiquitin produced as above to form a thioether. The labeling was performed in PBS with 1 mM TCEP. Labeled protein was separated from free label by gel filtration.

Ubiquitin ligase assay was performed substantially as described above, with a few modifications no nickel substrate was used in the reaction wells, so all of the components were free in solution. Equal amounts of fluoresceine labeled ubiquitin and IAEDANS labeled ubiquitin were used. The reaction was performed at room temperature for 2 hours in a volume of 100–150 µl, then stopped with 50 µl of 0.5 M EDTA, pH 8.

Following the reaction, the products were separated in PBS with 1 mM TCEP by HPLC on a Superdex-75 HR 10/30 size-exclusion column using fluorescence emission detection. A larger molecular weight cutoff gel-filtration column (e.g., Superdex 200 HR 10/30) could be used to resolve individual ligation species.

RESULTS

Figure 17:
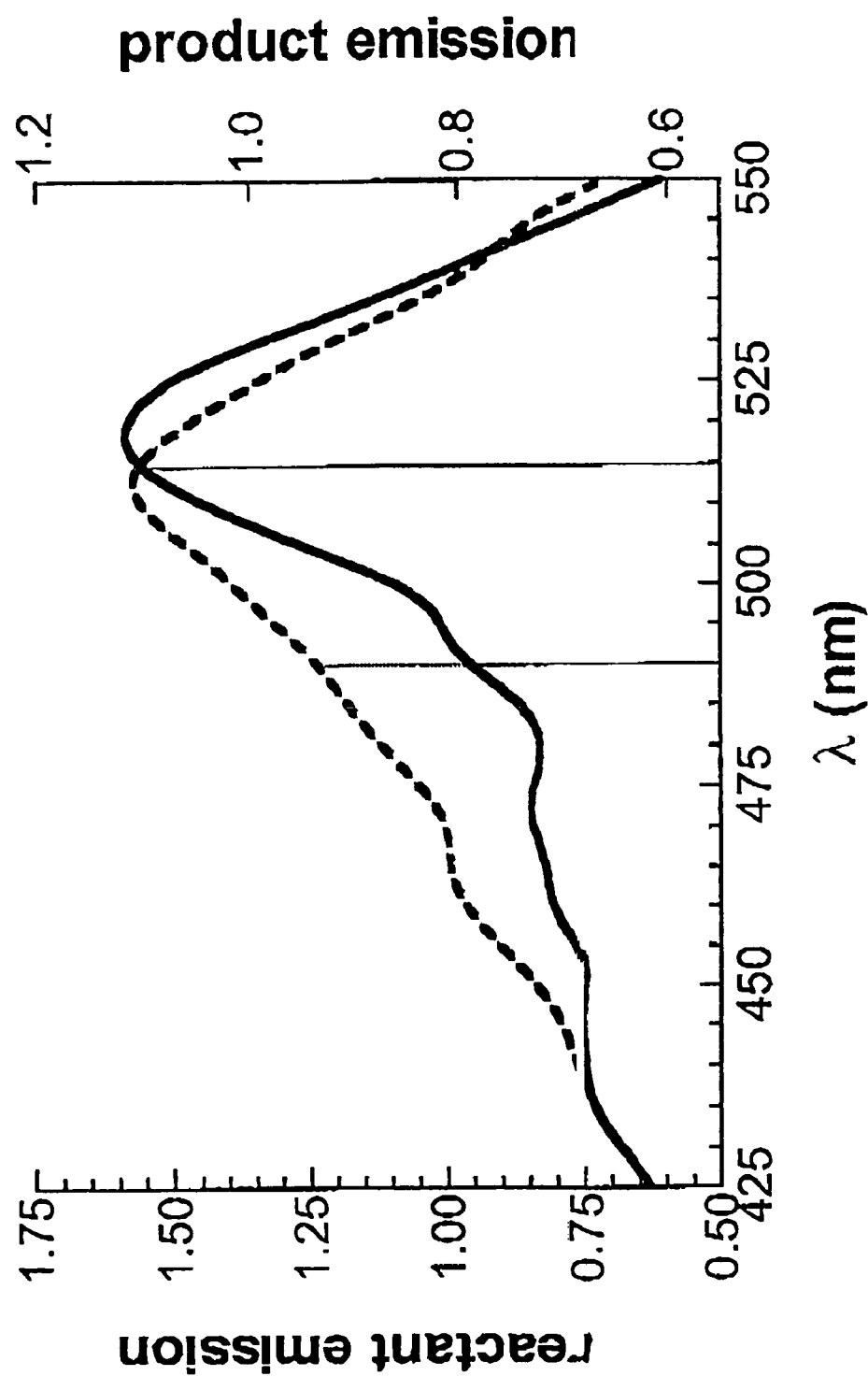
FIG. 17 shows the fluorescence emission spectra of free ubiquitin labeled with the FRET donor/acceptor pair EDANS and fluorescein under excitation at 336 nm. The dashed line shows the emission spectra of free labeled ubiquitin (reactants), while the solid line shows the emission spectra of labeled ubiquitin bound to E3 (products). The greatly increased 515:490 nm emission ratio of the E3-bound ubiquitin as compared with the free ubiquitin shows the energy transfer from the EDANS donor to the fluorescein acceptor of this FRET donor/acceptor pair.

Fluoresceine labeled ubiquitin and IAEDANS labeled ubiquitin was bound to E3 in approximately equal amounts. A comparison of the spectral analysis of fluorescent emission from the free (unligated) ubiquitin labeled with both fluorophores and the E3-bound ubiquitin shows a distinct increase in ratio of emission at 515 nm versus 490 nm (FIG. 17). This shows that in ligated ubiquitin, the fluorophores on different ubiquitin molecules are sufficiently close for FRET to be measured.

We claim:

1. A method of identifying a ubiquitination modulator comprising:
   a) combining, under conditions that favor ubiquitination activity:
      i) tag1-ubiquitin;
      ii) a candidate modulator;
      iii) ubiquitin activating enzyme (E1); and
      iv) tag2-ubiquitin conjugating enzyme (E2);
   b) measuring the amount of tag1-ubiquitin bound to said tag2-ubiquitin conjugating enzyme (E2), whereby a difference in bound ubiquitin as compared with a reaction performed in the absence of the candidate modulator indicates that the candidate is a ubiquitination modulator.

2. The method of claim 1, wherein ubiquitin conjugating enzyme (E2) is selected from the group consisting of Ubiquitin conjugating enzyme 5 (Ubc5), Ubiquitin conjugating enzyme 3 (Ubc3), Ubiquitin conjugating enzyme 4 (Ubc4), and Ubiquitin conjugating enzyme X (UbcX).

3. The method of claim 1, wherein tag1 is a label or a partner of a binding pair.

4. The method of claim 3, wherein said tag1 label is a fluorescent label.

5. The method of claim 4, wherein said measuring is by measuring luminescence.

6. The method of claim 3, wherein said tag1 partner of a binding pair is selected from the group consisting of an antigen, biotin, and calmodulin binding protein (CBP).

7. The method of claim 6, wherein said tag1 partner of a binding pair is labeled by indirect labeling.

8. The method of claim 6, wherein said antigen is FLAG (DYKDDDDK; SEQ ID NO:16).

9. The method of claim 7, wherein said indirect labeling is with a fluorescent label or a label enzyme.

10. The method of claim 7, wherein said tag1 partner of a binding pair is FLAG (DYKDDDDK; SEQ ID NO:16).

11. The method of claim 9, wherein said measuring is by measuring luminescence.

12. Them method of claim 9, wherein said label enzyme is selected from the group consisting of horseradish peroxidase, alkaline phosphatase and glucose oxidase.

13. The method of claim 9, wherein said tag1 partner of a binding pair is FLAG and said indirect labeling is via anti-FLAG (DYKDDDDK; SEQ ID NO:16).

14. The method of claim 12, wherein said label enzyme is reacted with a label enzyme substrate which produces a fluorescent product.

15. The method of claim 12, wherein said tag1 is FLAG (DYKDDDDK; SEQ ID NO:16).

16. The method of claim 14, wherein said measuring is by measuring luminescence.

17. The method of claim 3, wherein said tag2 is a surface substrate binding molecule.

18. The method of claim 17, wherein said surface substrate binding molecule is selected from the group consisting of polyhistidine (His-tag) and glutathione-S-transferase (GST)-tag.

19. The method of claim 18, wherein said surface substrate binding molecule is polyhistidine (His-tag).

20. The method of claim 19, wherein said combining and measuring is performed in a multi-well plate comprising a surface substrate comprising nickel.

* * * * *

SEQUENCE LISTING

<160> NUMBER OF SEQ ID NOS: 21

<210> SEQ ID NO 1
<211> LENGTH: 3177
<212> TYPE: DNA
<213> ORGANISM: Oryctolagus cuniculus
<220> FEATURE:
<223> OTHER INFORMATION: rabbit E1

<400> SEQUENCE: 1

-continued

| | |
|---|---|
| atgtccagct cgccgctgtc caagaaacgt cgcgtgtccg ggcctgatcc aaagccgggt | 60 |
| tctaactgct cccctgccca gtccgtgttg ccccaagtgc cctcggcgcc aaccaacgga | 120 |
| atggcgaaga acggcagtga agcagacatc gatgagggcc tttactcccg gcagctgtat | 180 |
| gtgttgggcc atgaggcgat gaagcggctc cagacatcca gcgttctggt gtcaggcctg | 240 |
| cggggcctgg gggtagagat cgcgaagaac atcatccttg gcggggtcaa ggccgtgacc | 300 |
| ctccatgacc agggcacggc ccagtgggct gacctctcct cccagttcta cctgcgagag | 360 |
| gaggacatag ggaaaaaccg cgctgaggtg tcacagcccc gccttgctga actcaatagc | 420 |
| tacgtgcctg tcaccgccta cactgggccg ctggttgagg acttcctcag tggcttccag | 480 |
| gtggtggtcc tcactaacag ccccctggag gaccagctgc gcgtgggcga gttctgtcat | 540 |
| agccgtggca tcaagctggt agtggcagac acgagaggct gtttgggca actcttctgc | 600 |
| gactttggag aggaaatgat cctcacagat ccaacggggg agcagcccct cagcaccatg | 660 |
| gtttctatgg tcaccaagga caaccctggt gtggttacct gcctgatgga ggcccgacat | 720 |
| gggtttgaga gtggcgattt tgtttccttc tccgaagtac agggcatgac tgagctcaat | 780 |
| ggaaaccagc ccatagagat caaagtcctg ggtccttaca cctttagcat ctgtgacacc | 840 |
| tccaacttct ccgattacat ccgtggaggc attgtcagcc aggtcaaagt acctaagaag | 900 |
| ataagcttta atccttgtc agcctcgctg cagagcctg actttgtgat gacggacttc | 960 |
| gccaagtttt ctcgccccgc tcagcttcac attggcttcc aggccttgca caagttctgt | 1020 |
| gcacagcaca gccggccacc tagacccccgg aacgaggagg atgcagcaga gctggtgacc | 1080 |
| ctagcacgcg ctgtgaactc taaagcctcg tcggcagtgc agcaagatag cctggatgag | 1140 |
| gacctcatcc ggaacctggc ctttgtggca gccggggacc tggcgcccat caatgccttc | 1200 |
| attgggggcc tggctgccca ggaagtcatg aaggcctgct ctgggaagtt tatgcccatc | 1260 |
| atgcagtggc tgtactttga tgcccttgag tgtctcccgg aggacaaaga atccctcaca | 1320 |
| gaggacaagt gcctcccgcg ccagaaccgt tatgatgggc aggtggctgt gtttggctca | 1380 |
| gacctgcaag agaagctggg caggcagaag tacttcctgg tgggtgcagg ggctattggc | 1440 |
| tgtgagctgc tcaagaactt tgccatgatt gggctgggct gtggtgagaa cggagaaata | 1500 |
| attgtcacag acatggacac cattgagaaa tctaatctga accgacagtt tctattccgg | 1560 |
| ccctgggatg tcacgaagtt aaaatctgac acagctgctg cagctgtgca ccagatgaat | 1620 |
| ccacatatcc gggtgacaag ccaccagaac cgtgtgggtc ctgacactga acgtatctac | 1680 |
| gacgacgatt tcttccaaac tctggatggc gtggccaacg ccttagacaa cgtggatgcc | 1740 |
| cgcatgtaca tggaccgccg ctgcgtgtac taccggaagc cgctgctcga atcaggcacc | 1800 |
| ctgggcacca agggcaacgt ccaggtggtg atccccttcc tgacagagtc ctacagctcc | 1860 |
| agccaagacc cacctgagaa gtccatcccc atctgtaccc tgaagaactt ccccaacgcc | 1920 |
| atcgaacaca ctcttcagtg ggctcgggat gaatttgaag cctcttcaa gcagccagcg | 1980 |
| gaaaatgtca accagtacct cacagaccct aagtttgtgg agcggacatt gcggctggcg | 2040 |
| ggtacccagc cactggaggt gctggaggct gtgcagcgca gcctggtgct gcagctaccg | 2100 |
| cagagctggg cagactgtgt gacctgggcc tgccaccact ggcacaccca gtattctaac | 2160 |
| aatatccggc agctgttgca caacttccct cccgaccagc tcacaagctc gggagctccc | 2220 |
| ttctggtctg ggcccaaacg ttgtcctcac ccactcacct ttgatgttag caaccctctg | 2280 |
| catctggact atgtgatggc tgctgccaac ctgtttgccc agacctacgg gctggcaggc | 2340 |
| tctcaggacc gagctgctgt ggccacactc ctgcagtctg tacaggtccc cgagtttacc | 2400 |

-continued

```
cccaagtctg cgtcaaaat ccacgtttct gaccaggagc tgcagagcgc caatgcttct    2460
gttgacgaca gccgtttaga ggagctcaag gctacgctgc ctagccccga caagctccct    2520
ggattcaaga tgtaccccat tgactttgag aaggatgatg atagtaactt tcacatggac    2580
ttcattgtgg ccgcatccaa cctccgggcc gaaaactatg acattccccc tgcagaccgg    2640
cacaagagca agctgattgc aggaagatc atcccagcca ttgccacgac acagcagct    2700 gtcgttggcc ttgtgtgtct ggagctgtac aaggtagtgc agggacaccg acacctcgac    2760
tcctacaaga tggtttcct caacctggcc ctgccgtttt tcggtttctc tgaacctctg    2820
gctgcaccac gtcaccagta ctataaccaa gagtggacat tgtgggatcg ctttgaggtt    2880
cagggactgc agcccaacgg tgaggagatg accctcaaac aattcctcga ctactttaag    2940
acagagcaca aattggagat taccatgctg tcccagggtg tgtccatgct ctattccttc    3000
tttatgccag ctgcgaagct caaggaacgg ttggaccagc cgatgacaga gattgtaagc    3060
cgtgtgtcga agcgaaagct gggccgccac gtgcgggcgc tggtgcttga gctgtgctgc    3120
aacgacgaga gcggcgagga cgtcgaagtc ccctacgtcc gatataccat ccgttaa      3177
```

<210> SEQ ID NO 2
<211> LENGTH: 1058
<212> TYPE: PRT
<213> ORGANISM: Oryctolagus cuniculus
<220> FEATURE:
<223> OTHER INFORMATION: rabbit E1

<400> SEQUENCE: 2

```
Met Ser Ser Pro Leu Ser Lys Lys Arg Arg Val Ser Gly Pro Asp
 1               5                  10                  15

Pro Lys Pro Gly Ser Asn Cys Ser Pro Ala Gln Ser Val Leu Pro Gln
                20                  25                  30

Val Pro Ser Ala Pro Thr Asn Gly Met Ala Lys Asn Gly Ser Glu Ala
            35                  40                  45

Asp Ile Asp Glu Gly Leu Tyr Ser Arg Gln Leu Tyr Val Leu Gly His
        50                  55                  60

Glu Ala Met Lys Arg Leu Gln Thr Ser Ser Val Leu Val Ser Gly Leu
65                  70                  75                  80

Arg Gly Leu Gly Val Glu Ile Ala Lys Asn Ile Ile Leu Gly Gly Val
                85                  90                  95

Lys Ala Val Thr Leu His Asp Gln Gly Thr Ala Gln Trp Ala Asp Leu
            100                 105                 110

Ser Ser Gln Phe Tyr Leu Arg Glu Glu Asp Ile Gly Lys Asn Arg Ala
        115                 120                 125

Glu Val Ser Gln Pro Arg Leu Ala Glu Leu Asn Ser Tyr Val Pro Val
    130                 135                 140

Thr Ala Tyr Thr Gly Pro Leu Val Glu Asp Phe Leu Ser Gly Phe Gln
145                 150                 155                 160

Val Val Val Leu Thr Asn Ser Pro Leu Glu Asp Gln Leu Arg Val Gly
                165                 170                 175

Glu Phe Cys His Ser Arg Gly Ile Lys Leu Val Val Ala Asp Thr Arg
            180                 185                 190

Gly Leu Phe Gly Gln Leu Phe Cys Asp Phe Gly Glu Glu Met Ile Leu
        195                 200                 205

Thr Asp Ser Asn Gly Glu Gln Pro Leu Ser Thr Met Val Ser Met Val
    210                 215                 220
```

-continued

```
Thr Lys Asp Asn Pro Gly Val Val Thr Cys Leu Asp Glu Ala Arg His
225                 230                 235                 240

Gly Phe Glu Ser Gly Asp Phe Val Ser Phe Ser Glu Val Gln Gly Met
            245                 250                 255

Thr Glu Leu Asn Gly Asn Gln Pro Ile Glu Ile Lys Val Leu Gly Pro
                260                 265                 270

Tyr Thr Phe Ser Ile Cys Asp Thr Ser Asn Phe Ser Asp Tyr Ile Arg
        275                 280                 285

Gly Gly Ile Val Ser Gln Val Lys Val Pro Lys Lys Ile Ser Phe Lys
290                 295                 300

Ser Leu Ser Ala Ser Leu Ala Glu Pro Asp Phe Val Met Thr Asp Phe
305                 310                 315                 320

Ala Lys Phe Ser Arg Pro Ala Gln Leu His Ile Gly Phe Gln Ala Leu
            325                 330                 335

His Lys Phe Cys Ala Gln His Ser Arg Pro Pro Arg Pro Arg Asn Glu
                340                 345                 350

Glu Asp Ala Ala Glu Leu Val Thr Leu Ala Arg Ala Val Asn Ser Lys
        355                 360                 365

Ala Ser Ser Ala Val Gln Gln Asp Ser Leu Asp Glu Asp Leu Ile Arg
370                 375                 380

Asn Leu Ala Phe Val Ala Ala Gly Asp Leu Ala Pro Ile Asn Ala Phe
385                 390                 395                 400

Ile Gly Gly Leu Ala Ala Gln Glu Val Met Lys Ala Cys Ser Gly Lys
            405                 410                 415

Phe Met Pro Ile Met Gln Trp Leu Tyr Phe Asp Ala Leu Glu Cys Leu
                420                 425                 430

Pro Glu Asp Lys Glu Ser Leu Thr Glu Asp Lys Cys Leu Pro Arg Gln
        435                 440                 445

Asn Arg Tyr Asp Gly Gln Val Ala Val Phe Gly Ser Asp Leu Gln Glu
450                 455                 460

Lys Leu Gly Arg Gln Lys Tyr Phe Leu Val Gly Ala Gly Ala Ile Gly
465                 470                 475                 480

Cys Glu Leu Leu Lys Asn Phe Ala Met Ile Gly Leu Gly Cys Gly Glu
            485                 490                 495

Asn Gly Glu Ile Ile Val Thr Asp Met Asp Thr Ile Glu Lys Ser Asn
                500                 505                 510

Leu Asn Arg Gln Phe Leu Phe Arg Pro Trp Asp Val Thr Lys Leu Lys
        515                 520                 525

Ser Asp Thr Ala Ala Ala Val His Gln Met Asn Pro His Ile Arg
530                 535                 540

Val Thr Ser His Gln Asn Arg Val Gly Pro Asp Thr Glu Arg Ile Tyr
545                 550                 555                 560

Asp Asp Asp Phe Phe Gln Thr Leu Asp Gly Val Ala Asn Ala Leu Asp
            565                 570                 575

Asn Val Asp Ala Arg Met Tyr Met Asp Arg Arg Cys Val Tyr Tyr Arg
                580                 585                 590

Lys Pro Leu Leu Glu Ser Gly Thr Leu Gly Thr Lys Gly Asn Val Gln
        595                 600                 605

Val Val Ile Pro Phe Leu Thr Glu Ser Tyr Ser Ser Ser Gln Asp Pro
610                 615                 620

Pro Glu Lys Ser Ile Pro Ile Cys Thr Leu Lys Asn Phe Pro Asn Ala
625                 630                 635                 640

Ile Glu His Thr Leu Gln Trp Ala Arg Asp Glu Phe Glu Gly Leu Phe
```

-continued

```
                645                 650                 655
Lys Gln Pro Ala Glu Asn Val Asn Gln Tyr Leu Thr Asp Pro Lys Phe
            660                 665                 670
Val Glu Arg Thr Leu Arg Leu Ala Gly Thr Gln Pro Leu Glu Val Leu
            675                 680                 685
Glu Ala Val Gln Arg Ser Leu Val Leu Gln Leu Pro Gln Ser Trp Ala
            690                 695                 700
Asp Cys Val Thr Trp Ala Cys His His Trp His Thr Gln Tyr Ser Asn
705                 710                 715                 720
Asn Ile Arg Gln Leu Leu His Asn Phe Pro Pro Asp Gln Leu Thr Ser
            725                 730                 735
Ser Gly Ala Pro Phe Trp Ser Gly Pro Lys Arg Cys Pro His Pro Leu
            740                 745                 750
Thr Phe Asp Val Ser Asn Pro Leu His Leu Asp Tyr Val Met Ala Ala
            755                 760                 765
Ala Asn Leu Phe Ala Gln Thr Tyr Gly Leu Ala Gly Ser Gln Asp Arg
            770                 775                 780
Ala Ala Val Ala Thr Leu Leu Gln Ser Val Gln Val Pro Glu Phe Thr
785                 790                 795                 800
Pro Lys Ser Gly Val Lys Ile His Val Ser Asp Gln Glu Leu Gln Ser
            805                 810                 815
Ala Asn Ala Ser Val Asp Asp Ser Arg Leu Glu Glu Leu Lys Ala Thr
            820                 825                 830
Leu Pro Ser Pro Asp Lys Leu Pro Gly Phe Lys Met Tyr Pro Ile Asp
            835                 840                 845
Phe Glu Lys Asp Asp Asp Ser Asn Phe His Met Asp Phe Ile Val Ala
            850                 855                 860
Ala Ser Asn Leu Arg Ala Glu Asn Tyr Asp Ile Pro Pro Ala Asp Arg
865                 870                 875                 880
His Lys Ser Lys Leu Ile Ala Gly Lys Ile Ile Pro Ala Ile Ala Thr
            885                 890                 895
Thr Thr Ala Ala Val Val Gly Leu Val Cys Leu Glu Leu Tyr Lys Val
            900                 905                 910
Val Gln Gly His Arg His Leu Asp Ser Tyr Lys Asn Gly Phe Leu Asn
            915                 920                 925
Leu Ala Leu Pro Phe Phe Gly Phe Ser Glu Pro Leu Ala Ala Pro Arg
            930                 935                 940
His Gln Tyr Tyr Asn Gln Glu Trp Thr Leu Trp Asp Arg Phe Glu Val
945                 950                 955                 960
Gln Gly Leu Gln Pro Asn Gly Glu Glu Met Thr Leu Lys Gln Phe Leu
            965                 970                 975
Asp Tyr Phe Lys Thr Glu His Lys Leu Glu Ile Thr Met Leu Ser Gln
            980                 985                 990
Gly Val Ser Met Leu Tyr Ser Phe Phe Met Pro Ala Ala Lys Leu Lys
            995                 1000                1005
Glu Arg Leu Asp Gln Pro Met Thr Glu Ile Val Ser Arg Val Ser Lys
            1010                1015                1020
Arg Lys Leu Gly Arg His Val Arg Ala Leu Val Leu Glu Leu Cys Cys
1025                1030                1035                1040
Asn Asp Glu Ser Gly Glu Asp Val Glu Val Pro Tyr Val Arg Tyr Thr
            1045                1050                1055
Ile Arg
```

```
<210> SEQ ID NO 3
<211> LENGTH: 444
<212> TYPE: DNA
<213> ORGANISM: Homo sapiens
<220> FEATURE:
<223> OTHER INFORMATION: E2 Ubc5c

<400> SEQUENCE: 3
atggcgctga aacggattaa taaggaactt agtgatttgg cccgtgaccc tccagcacaa      60
tgttctgcag gtccagttgg ggatgatatg tttcattggc aagccacaat tatgggacct     120
aatgacagcc catatcaagg cggtgtattc tttttgacaa ttcatttttcc tacagactac    180 cccttcaaac cacctaaggt tgcatttaca acaagaattt atcatccaaa tattaacagt     240
aatggcagca tttgtctcga tattctaaga tcacagtggt cgcctgcttt aacaatttct     300
aaagttcttt tatccatttg ttcactgcta tgtgatccaa acccagatga ccccctagtg     360
ccagagattg cacggatcta taaaacagac agagataagt acaacagaat atctcgggaa     420
tggactcaga gtatgccat gtga                                             444

<210> SEQ ID NO 4
<211> LENGTH: 147
<212> TYPE: PRT
<213> ORGANISM: Homo sapiens
<220> FEATURE:
<223> OTHER INFORMATION: E2 Ubc5c

<400> SEQUENCE: 4

Met Ala Leu Lys Arg Ile Asn Lys Glu Leu Ser Asp Leu Ala Arg Asp
 1               5                  10                  15

Pro Pro Ala Gln Cys Ser Ala Gly Pro Val Gly Asp Asp Met Phe His
                20                  25                  30

Trp Gln Ala Thr Ile Met Gly Pro Asn Asp Ser Pro Tyr Gln Gly Gly
            35                  40                  45

Val Phe Phe Leu Thr Ile His Phe Pro Thr Asp Tyr Pro Phe Lys Pro
        50                  55                  60

Pro Lys Val Ala Phe Thr Thr Arg Ile Tyr His Pro Asn Ile Asn Ser
    65                  70                  75                  80

Asn Gly Ser Ile Cys Leu Asp Ile Leu Arg Ser Gln Trp Ser Pro Ala
                85                  90                  95

Leu Thr Ile Ser Lys Val Leu Leu Ser Ile Cys Ser Leu Leu Cys Asp
               100                 105                 110

Pro Asn Pro Asp Asp Pro Leu Val Pro Glu Ile Ala Arg Ile Tyr Lys
           115                 120                 125

Thr Asp Arg Asp Lys Tyr Asn Arg Ile Ser Arg Glu Trp Thr Gln Lys
       130                 135                 140

Tyr Ala Met
145

<210> SEQ ID NO 5
<211> LENGTH: 84
<212> TYPE: PRT
<213> ORGANISM: Homo sapiens
<220> FEATURE:
<223> OTHER INFORMATION: RING finger protein APC11

<400> SEQUENCE: 5

Met Lys Val Lys Ile Lys Cys Trp Asn Gly Val Ala Thr Trp Leu Trp
 1               5                  10                  15
```

Val Ala Asn Asp Glu Asn Cys Gly Ile Cys Arg Met Ala Phe Asn Gly
            20                  25                  30

Cys Cys Pro Asp Cys Lys Val Pro Gly Asp Asp Cys Pro Leu Val Trp
        35                  40                  45

Gly Gln Cys Ser His Cys Phe His Met His Cys Ile Leu Lys Trp Leu
    50                  55                  60

His Ala Gln Gln Val Gln Gln His Cys Pro Met Cys Arg Gln Thr Trp
65                  70                  75                  80

Lys Phe Lys Glu

<210> SEQ ID NO 6
<211> LENGTH: 108
<212> TYPE: PRT
<213> ORGANISM: Homo sapiens
<220> FEATURE:
<223> OTHER INFORMATION: RING finger protein ROC1

<400> SEQUENCE: 6

Met Ala Ala Ala Met Asp Val Asp Thr Pro Ser Gly Thr Asn Ser Gly
1               5                   10                  15

Ala Gly Lys Lys Arg Phe Glu Val Lys Lys Trp Asn Ala Val Ala Leu
            20                  25                  30

Trp Ala Trp Asp Ile Val Val Asp Asn Cys Ala Ile Cys Arg Asn His
        35                  40                  45

Ile Met Asp Leu Cys Ile Glu Cys Gln Ala Asn Gln Ala Ser Ala Thr
    50                  55                  60

Ser Glu Glu Cys Thr Val Ala Trp Gly Val Cys Asn His Ala Phe His
65                  70                  75                  80

Phe His Cys Ile Ser Arg Trp Leu Lys Thr Arg Gln Val Cys Pro Leu
                85                  90                  95

Asp Asn Arg Glu Trp Glu Phe Gln Lys Tyr Gly His
            100                 105

<210> SEQ ID NO 7
<211> LENGTH: 342
<212> TYPE: DNA
<213> ORGANISM: Homo sapiens
<220> FEATURE:
<223> OTHER INFORMATION: RING finger protein ROC2

<400> SEQUENCE: 7
atggccgacg tggaagacgg agaggaaacc tgcgccctgg cctctcactc cgggagctca      60
ggctcaacgt cgggaggcga caagatgttc tccctcaaga gtggaacccc ggtggccatg     120
tggagctggg acgtggagtg cgatacgtgc gccatctgca gggtccaggt gatggatgcc     180
tgtcttagat gtcaagctga aaacaaacaa gaggactgtg ttgtggtctg gggagaatgt     240
aatcattcct tccacaactg ctgcatgtcc ctgtgggtga aacagaacaa tcgctgccct     300
ctctgccagc aggactgggt ggtccaaaga atcggcaaat ga                        342

<210> SEQ ID NO 8
<211> LENGTH: 113
<212> TYPE: PRT
<213> ORGANISM: Homo sapiens
<220> FEATURE:
<223> OTHER INFORMATION: RING finger protein ROC2

<400> SEQUENCE: 8

Met Ala Asp Val Glu Asp Gly Glu Glu Thr Cys Ala Leu Ala Ser His
1               5                   10                  15

| | | | | | | | | | | | |
|---|---|---|---|---|---|---|---|---|---|---|---|
|Ser|Gly|Ser|Gly|Ser|Thr|Ser|Gly|Gly|Asp|Lys|Met|Phe|Ser|Leu|
| | |20| | | |25| | | |30| | | | |

Ser Gly Ser Gly Ser Thr Ser Gly Gly Asp Lys Met Phe Ser Leu
                20                  25                  30

Lys Lys Trp Asn Pro Val Ala Met Trp Ser Trp Asp Val Glu Cys Asp
        35                  40                  45

Thr Cys Ala Ile Cys Arg Val Gln Val Met Asp Ala Cys Leu Arg Cys
    50                  55                  60

Gln Ala Glu Asn Lys Gln Glu Asp Cys Val Val Val Trp Gly Glu Cys
65                  70                  75                  80

Asn His Ser Phe His Asn Cys Cys Met Ser Leu Trp Val Lys Gln Asn
                85                  90                  95

Asn Arg Cys Pro Leu Cys Gln Gln Asp Trp Val Val Gln Arg Ile Gly
            100                 105                 110

Lys

<210> SEQ ID NO 9
<211> LENGTH: 2343
<212> TYPE: DNA
<213> ORGANISM: Homo sapiens
<220> FEATURE:
<223> OTHER INFORMATION: Cullin CUL5

<400> SEQUENCE: 9

```
atggcgacgt ctaatctgtt aaagaataaa ggttctcttc agtttgaaga caaatgggat      60
tttatgcgcc cgattgtttt gaagctttta cgccaggaat ctgttacaaa acagcagtgg     120
tttgatctgt tttcggatgt gcatgcagtc tgtctttggg atgataaagg cccagcaaaa     180
attcatcagg cttttaaaga agatattctt gagtttatta agcaggcaca ggcacgagta     240
ctgagccatc aagatgatac ggctttgcta aaagcatata ttgttgaatg gcgaaagttc     300
tttacacaat gtgatatttt accaaaacct ttttgtcaac tagagattac tttaatgggt     360
aaacagggca gcaataaaaa atcaaatgtg aagacagta ttgttcgaaa gcttatgctt      420
gatacatgga atgagtcaat cttttcaaac ataaaaaaca gactccaaga tagtgcaatg     480
aagctggtac atgctgagag attgggagaa gcttttgatt ctcagctggt tattggagta     540
agagaatcct atgttaacct ttgttctaat cctgaggata aacttcaaat ttatagggac     600 aatttttgaga aggcatactt ggattcaaca gagagatttt atagaacaca agcaccctcg     660
tatttacaac caaatggtgt acagaattat atgaaatatg cagatgctaa attaaaagaa     720
gaagaaaaac gagcactacg ttatttagaa acaagacgag aatgtaactc cgttgaagca     780
ctcatggaat gctgtgtaaa tgccctggtg acatcattta agagactat cttagctgag     840 tgccaaggca tgatcaagag aaatgaaact gaaaaattac atttaatgtt ttcattgatg     900
gacaaagttc ctaatggtat agagccaatg ttgaaagact ggaggaaca tatcattagt     960 gctggcctgg cagatatggt agcagctgct gaaactatta ctactgactc tgagaaatac    1020
gttgagcagt tacttacact atttaataga tttagtaaac tcgtcaaaga agcttttcaa    1080
gatgatccac gatttcttac tgcaagagat aaggcgtata agcagttgt taatgatgct    1140 accatattta aacttgaatt accttttgaag cagaagggg tgggattaaa aactcagcct    1200
gaatcaaaat gccctgagct gcttgccaat tactgtgaca tgttgctaag aaaaacacca    1260
ttaagcaaaa aactaaccctc tgaagagatt gaagcaaagc ttaagaagt gctcttggta    1320 cttaagtatg tacagaacaa agatgttttt atgaggtatc ataagctca tttgacacga    1380 cgtcttatat tagacatctc tgccgatagt gaaattgaag aaaacatggt agagtggcta    1440
```

-continued

```
agagaagttg gtatgccagc ggattatgta acaagcttg ctagaatgtt tcaggacata      1500
aaagtatctg aagatttgaa ccaagcttt aaggaaatgc acaaaataa taaattggca       1560 ttaccagctg attcagttaa tataaaaatt ctgaatgctg gcgcctggtc aagaagttct     1620
gagaaagtct ttgtctcact tcctactgaa ctggaggact tgataccgga agtagaagaa     1680
ttctacaaaa aaaatcatag tggtagaaaa ttacattggc atcatctcat gtcaaatgga     1740
attataacat ttaagaatga agttggtcaa tatgatttgg aggtaaccac gtttcagctc     1800
gctgtattgt ttgcatggaa ccaaagaccc agagagaaaa tcagctttga aaatcttaag     1860
cttgcaactg aactccctga tgctgaactt aggaggactt tatggtcttt agtagctttc     1920
ccaaaactca aacggcaagt ttttttgtat gaccctcaag tcaactcacc caaagacttt     1980
acagaaggta ccctcttctc agtgaaccag gagttcagtt aataaaaaa tgcaaaggtt      2040 cagaaaggg gtaaaatcaa cttgattgga cgtttgcagc tcactacaga aaggatgaga     2100
gaagaagaga atgaaggaat agttcaacta cgaatactaa gaacccagga agctatcata    2160 caataatga aaatgagaaa gaaaattagt aatgctcagc tgcagactga attagtagaa     2220
attttgaaaa acatgttctt gccacaaaag aaaatgataa aagagcaaat agagtggcta    2280
atagagcaca aatacatcag aagagatgaa tctgatatca acactttcat atatatggca   2340
taa                                                                    2343
```

<210> SEQ ID NO 10
<211> LENGTH: 861
<212> TYPE: PRT
<213> ORGANISM: Homo sapiens
<220> FEATURE:
<223> OTHER INFORMATION: Cullin CUL5

<400> SEQUENCE: 10

```
Met Arg Ser Phe Ala Trp Gly Ser Ser Asp His Val Gly Asp Lys
  1               5                  10                  15

Ser Glu Glu Ala Pro Gly Ala Trp Asp Glu Val Ser Ala Val Gly Ala
                 20                  25                  30

Leu Leu Gln Arg Pro Pro His Pro Gly Ala Gly Pro Thr Gly Pro Gly
             35                  40                  45

Pro Trp Trp Glu Leu Arg Pro Pro Val Lys Ala Trp Pro Gly Arg Glu
         50                  55                  60

Arg His Glu Phe Ser Arg Arg Leu Val Ser Arg Glu Ser Lys Leu Lys
     65                  70                  75                  80

Asn Met Ala Thr Ser Asn Leu Leu Lys Asn Lys Gly Ser Leu Gln Phe
                     85                  90                  95

Glu Asp Lys Trp Asp Phe Met Arg Pro Ile Val Leu Lys Leu Leu Arg
                100                 105                 110

Gln Glu Ser Val Thr Lys Gln Gln Trp Phe Asp Leu Phe Ser Asp Val
            115                 120                 125

His Ala Val Cys Leu Trp Asp Asp Lys Gly Pro Ala Lys Ile His Gln
        130                 135                 140

Ala Leu Lys Glu Asp Ile Leu Glu Phe Ile Lys Gln Ala Gln Ala Arg
145                 150                 155                 160

Val Leu Ser His Gln Asp Asp Thr Ala Leu Leu Lys Ala Tyr Ile Val
                    165                 170                 175

Glu Trp Arg Lys Phe Phe Thr Gln Cys Asp Ile Leu Pro Lys Pro Phe
                180                 185                 190

Cys Gln Leu Glu Ile Thr Leu Met Gly Lys Gln Gly Ser Asn Lys Lys
```

-continued

```
            195                 200                 205
Ser Asn Val Glu Asp Ser Ile Val Arg Lys Leu Met Leu Asp Thr Trp
    210                 215                 220
Asn Glu Ser Ile Phe Ser Asn Ile Lys Asn Arg Leu Gln Asp Ser Ala
225                 230                 235                 240
Met Lys Leu Val His Ala Glu Arg Leu Gly Glu Ala Phe Asp Ser Gln
                245                 250                 255
Leu Val Ile Gly Val Arg Glu Ser Tyr Val Asn Leu Cys Ser Asn Pro
            260                 265                 270
Glu Asp Lys Leu Gln Ile Tyr Arg Asp Asn Phe Glu Lys Ala Tyr Leu
        275                 280                 285
Asp Ser Thr Glu Arg Phe Tyr Arg Thr Gln Ala Pro Ser Tyr Leu Gln
    290                 295                 300
Pro Asn Gly Val Gln Asn Tyr Met Lys Tyr Ala Asp Ala Lys Leu Lys
305                 310                 315                 320
Glu Glu Glu Lys Arg Ala Leu Arg Tyr Leu Glu Thr Arg Arg Glu Cys
                325                 330                 335
Asn Ser Val Glu Ala Leu Met Glu Cys Cys Val Asn Ala Leu Val Thr
            340                 345                 350
Ser Phe Lys Glu Thr Ile Leu Ala Glu Cys Gln Gly Met Ile Lys Arg
        355                 360                 365
Asn Glu Thr Glu Lys Leu His Leu Met Phe Ser Leu Met Asp Lys Val
    370                 375                 380
Pro Asn Gly Ile Glu Pro Met Leu Lys Asp Leu Glu Glu His Ile Ile
385                 390                 395                 400
Ser Ala Gly Leu Ala Asp Met Val Ala Ala Glu Thr Ile Thr Thr
                405                 410                 415
Asp Ser Glu Lys Tyr Val Glu Gln Leu Leu Thr Leu Phe Asn Arg Phe
            420                 425                 430
Ser Lys Leu Val Lys Glu Ala Phe Gln Asp Asp Pro Arg Phe Leu Thr
        435                 440                 445
Ala Arg Asp Lys Ala Tyr Lys Ala Val Val Asn Asp Ala Thr Ile Phe
    450                 455                 460
Lys Leu Glu Leu Pro Leu Lys Gln Lys Gly Val Gly Leu Lys Thr Gln
465                 470                 475                 480
Pro Glu Ser Lys Cys Pro Glu Leu Leu Ala Asn Tyr Cys Asp Met Leu
                485                 490                 495
Leu Arg Lys Thr Pro Leu Ser Lys Lys Leu Thr Ser Glu Glu Ile Glu
            500                 505                 510
Ala Lys Leu Lys Glu Val Leu Leu Val Leu Lys Tyr Val Gln Asn Lys
        515                 520                 525
Asp Val Phe Met Arg Tyr His Lys Ala His Leu Thr Arg Arg Leu Ile
    530                 535                 540
Leu Asp Ile Ser Ala Asp Ser Glu Ile Glu Glu Asn Met Val Glu Trp
545                 550                 555                 560
Leu Arg Glu Val Gly Met Pro Ala Asp Tyr Val Asn Lys Leu Ala Arg
                565                 570                 575
Met Phe Gln Asp Ile Lys Val Ser Glu Asp Leu Asn Gln Ala Phe Lys
            580                 585                 590
Glu Met His Lys Asn Asn Lys Leu Ala Leu Pro Ala Asp Ser Val Asn
        595                 600                 605
Ile Lys Ile Leu Asn Ala Gly Ala Trp Ser Arg Ser Ser Glu Lys Val
    610                 615                 620
```

```
Phe Val Ser Leu Pro Thr Glu Leu Glu Asp Leu Ile Pro Glu Val Glu
625                 630                 635                 640

Glu Phe Tyr Lys Lys Asn His Ser Gly Arg Lys Leu His Trp His His
            645                 650                 655

Leu Met Ser Asn Gly Ile Ile Thr Phe Lys Asn Glu Val Gly Gln Tyr
            660                 665                 670

Asp Leu Glu Val Thr Thr Phe Gln Leu Ala Val Leu Phe Ala Trp Asn
            675                 680                 685

Gln Arg Pro Arg Glu Lys Ile Ser Phe Glu Asn Leu Lys Leu Ala Thr
690                 695                 700

Glu Leu Pro Asp Ala Glu Leu Arg Arg Thr Leu Trp Ser Leu Val Ala
705                 710                 715                 720

Phe Pro Lys Leu Lys Arg Gln Val Phe Leu Tyr Asp Pro Gln Val Asn
                725                 730                 735

Ser Pro Lys Asp Phe Thr Glu Gly Thr Leu Phe Ser Val Asn Gln Glu
                740                 745                 750

Phe Ser Leu Ile Lys Asn Ala Lys Val Gln Lys Arg Gly Lys Ile Asn
            755                 760                 765

Leu Ile Gly Arg Leu Gln Leu Thr Thr Glu Arg Met Arg Glu Glu Glu
770                 775                 780

Asn Glu Gly Ile Val Gln Leu Arg Ile Leu Arg Thr Gln Glu Ala Ile
785                 790                 795                 800

Ile Gln Ile Met Lys Met Arg Lys Lys Ile Ser Asn Ala Gln Leu Gln
                805                 810                 815

Thr Glu Leu Val Glu Ile Leu Lys Asn Met Phe Leu Pro Gln Lys Lys
                820                 825                 830

Met Ile Lys Glu Gln Ile Glu Trp Leu Ile Glu His Lys Tyr Ile Arg
            835                 840                 845

Arg Asp Glu Ser Asp Ile Asn Thr Phe Ile Tyr Met Ala
850                 855                 860

<210> SEQ ID NO 11
<211> LENGTH: 2469
<212> TYPE: DNA
<213> ORGANISM: Homo sapiens
<220> FEATURE:
<223> OTHER INFORMATION: Cullin APC2

<400> SEQUENCE: 11
atggcggcgg cagttgtggt ggcggagggg gacagcgact cccggcccgg acaggagttg      60
ttagtggcct ggaacaccgt gagcaccggc ctggtgccgc cggctgcgct ggggctggtg     120
tcttcccgga ccagcggtgc agtcccgcca aggaagagg agctccgggc ggcggtggag      180
gttctgaggg ccacgggct acactcggtc ctggaggagt ggttcgtgga ggtgctgcag      240
aacgatctgc aggccaacat ctcccctgag ttctggaatg ccatctccca atgcgagaac     300
tctgcggatg agccccagtg cctttttgcta ctccttgacg cttttggcct gctggagagc     360
cgcctggatc cctacctgcg tagcctagag ctgctggaga atggactcg cctgggcttg      420 ctgatgggca ctggtgctca ggggctgcga agaagtcc acactatgtt gcgcggagtc       480 ttgttctta gcaccccag aaccttccaa gagatgatcc agcgtctgta tgggtgcttc       540
ttgagagtct atatgcagag taagaggaag ggggaagggg gcacagaccc ggaactggaa      600
ggggagctgg acagcggta tgcccgtcgc cggtactacc ggctcctgca gagcccgctg      660
tgtgcagggt gcagcagtga caagcaacag tgctggtgtc gccaggctct ggagcagttc     720
```

-continued

```
catcagctca gccaggtctt acacaggctc agtctgctgg agcgggtcag tgccgaggct    780
gtgaccacca ccctgcacca ggtgacccgg agaggatgg aggaccgttg ccggggcgag     840
tacgagcgct ccttcctgcg tgagttccac aagtggatcg agcgggtggt cggctggctc    900
ggcaaggtgt tcctgcagga cggccccgcc aggcccgcat ctcccgaggc cggcaacacc    960
ctgcgccgct ggcgctgcca cgtgcaaagg ttcttctacc gcatctacgc cagcctgcgc   1020
atcgaggagc tcttcagcat cgtccgagac ttcccagact cccggccagc catcgaggac   1080
ctcaagtact gcctggagag gacgaccag aggcagcagc tgctcgtgtc cctcaaggct    1140
gccctggaga ctcggctcct gcatccaggc gtcaacacgt gtgacatcat caccctctat   1200
atctctgcca tcaaggcgct gcgcgtgctg gacccttcca tggtcatcct ggaggtggcc   1260
tgtgagccta tccgccgcta cctgaggacg cgggaggaca cagtgcggca gattgtggct   1320
gggctgacgg gggactcgga cgggacaggg gacctggctg ttgagctgtc caagaccgac   1380
ccggcgagcc tggagacagg ccaggacagt gaggatgact caggcgagcc agaggactgg   1440
gtcccggacc ctgtggatgc cgatccaggg aagtcgagct ccaagcggcg ttcatcggac   1500
atcatcagcc tgctggtcag catctacggc agcaaggacc tcttcatcaa tgagtaccgc   1560
tcgctgctgg ccgaccgcct gctgcaccag ttcagcttca gccccgagcg ggagatccgc   1620
aacgtggagc tgctgaagct cgctttggc gaggccccaa tgcacttctg tgaagtcatg    1680
ctgaaggaca tggcggactc ccgccgcatc aatgccaaca tccggggagga ggatgagaag   1740
cggccagcag aggagcagcc accgttcggg gtctacgctg tcatcctgtc cagtgagttc   1800
tggccgccct tcaaggacga gaagctggag gtccccgagg atatcagggc agccctggag   1860
gcttactgca agaagtatga gcagctcaag gccatgcgga ccctcagttg gaagcacacc   1920
ctgggcctgg tgaccatgga cgtggagctg gccgaccgca cgctgtctgt ggcggtcacc   1980
ccagtacagg cggtgatctt gctgtatttt caggaccaag ccagctggac cctgaggaa    2040
ctgagcaagg cggtgaaaat gcccgtggcg ctgctgcggc ggcggatgtc cgtgtggctg   2100
cagcagggtg tgctgcgtga ggagccccccc ggcaccttct ctgtcattga ggaggagcgg   2160
cctcaggacc gggacaacat ggtgctcatt gacagtgacg acgagagcga ctccggcatg   2220
gcctcccagg ccgaccagaa ggaggaggag ctgctgctct tctggacgta catccaggcc   2280
atgctgacca acctggagag cctctcactg gatcgtatct acaacatgct ccgcatgttt   2340
gtggtgactg gcctgcact ggccgagatt gacctgcagg agctgcaggg ctacctgcag    2400
aagaaggtgc gggaccagca gctcgtctac tcggccggcg tctaccgcct gcccaagaac   2460
tgcagctga                                                            2469
```

<210> SEQ ID NO 12
<211> LENGTH: 822
<212> TYPE: PRT
<213> ORGANISM: Homo sapiens
<220> FEATURE:
<223> OTHER INFORMATION: Cullin APC2

<400> SEQUENCE: 12

```
Met Ala Ala Val Val Ala Glu Gly Asp Ser Asp Ser Arg Pro
 1               5                  10                  15

Gly Gln Glu Leu Leu Val Ala Trp Asn Thr Val Ser Thr Gly Leu Val
            20                  25                  30

Pro Pro Ala Ala Leu Gly Leu Val Ser Ser Arg Thr Ser Gly Ala Val
        35                  40                  45
```

```
Pro Pro Lys Glu Glu Leu Arg Ala Ala Val Glu Val Leu Arg Gly
    50                  55                  60
His Gly Leu His Ser Val Leu Glu Glu Trp Phe Val Glu Val Leu Gln
 65                  70                  75                  80
Asn Asp Leu Gln Ala Asn Ile Ser Pro Glu Phe Trp Asn Ala Ile Ser
                 85                  90                  95
Gln Cys Glu Asn Ser Ala Asp Glu Pro Gln Cys Leu Leu Leu Leu
                100                 105                 110
Asp Ala Phe Gly Leu Leu Glu Ser Arg Leu Asp Pro Tyr Leu Arg Ser
                115                 120                 125
Leu Glu Leu Leu Glu Lys Trp Thr Arg Leu Gly Leu Leu Met Gly Thr
    130                 135                 140
Gly Ala Gln Gly Leu Arg Glu Glu Val His Thr Met Leu Arg Gly Val
145                 150                 155                 160
Leu Phe Phe Ser Thr Pro Arg Thr Phe Gln Glu Met Ile Gln Arg Leu
                165                 170                 175
Tyr Gly Cys Phe Leu Arg Val Tyr Met Gln Ser Lys Arg Lys Gly Glu
                180                 185                 190
Gly Gly Thr Asp Pro Glu Leu Glu Gly Glu Leu Asp Ser Arg Tyr Ala
                195                 200                 205
Arg Arg Arg Tyr Tyr Arg Leu Leu Gln Ser Pro Leu Cys Ala Gly Cys
    210                 215                 220
Ser Ser Asp Lys Gln Gln Cys Trp Cys Arg Gln Ala Leu Glu Gln Phe
225                 230                 235                 240
His Gln Leu Ser Gln Val Leu His Arg Leu Ser Leu Glu Arg Val
                245                 250                 255
Ser Ala Glu Ala Val Thr Thr Thr Leu His Gln Val Thr Arg Glu Arg
                260                 265                 270
Met Glu Asp Arg Cys Arg Gly Glu Tyr Glu Arg Ser Phe Leu Arg Glu
    275                 280                 285
Phe His Lys Trp Ile Glu Arg Val Val Gly Trp Leu Gly Lys Val Phe
    290                 295                 300
Leu Gln Asp Gly Pro Ala Arg Pro Ala Ser Pro Glu Ala Gly Asn Thr
305                 310                 315                 320
Leu Arg Arg Trp Arg Cys His Val Gln Arg Phe Phe Tyr Arg Ile Tyr
                325                 330                 335
Ala Ser Leu Arg Ile Glu Glu Leu Phe Ser Ile Val Arg Asp Phe Pro
                340                 345                 350
Asp Ser Arg Pro Ala Ile Glu Asp Leu Lys Tyr Cys Leu Glu Arg Thr
                355                 360                 365
Asp Gln Arg Gln Gln Leu Leu Val Ser Leu Lys Ala Ala Leu Glu Thr
    370                 375                 380
Arg Leu His Pro Gly Val Asn Thr Cys Asp Ile Ile Thr Leu Tyr
385                 390                 395                 400
Ile Ser Ala Ile Lys Ala Leu Arg Val Leu Asp Pro Ser Met Val Ile
                405                 410                 415
Leu Glu Val Ala Cys Glu Pro Ile Arg Arg Tyr Leu Arg Thr Arg Glu
                420                 425                 430
Asp Thr Val Arg Gln Ile Val Ala Gly Leu Thr Gly Asp Ser Asp Gly
                435                 440                 445
Thr Gly Asp Leu Ala Val Glu Leu Ser Lys Thr Asp Pro Ala Ser Leu
450                 455                 460
```

Glu Thr Gly Gln Asp Ser Asp Asp Ser Gly Pro Glu Asp Trp
465                 470                 475                 480

Val Pro Asp Pro Val Asp Ala Asp Pro Gly Lys Ser Ser Lys Arg
                485                 490                 495

Arg Ser Ser Asp Ile Ile Ser Leu Leu Val Ser Ile Tyr Gly Ser Lys
            500                 505                 510

Asp Leu Phe Ile Asn Glu Tyr Arg Ser Leu Leu Ala Asp Arg Leu Leu
        515                 520                 525

His Gln Phe Ser Phe Ser Pro Glu Arg Glu Ile Arg Asn Val Glu Leu
    530                 535                 540

Leu Lys Leu Arg Phe Gly Glu Ala Pro Met His Phe Cys Glu Val Met
545                 550                 555                 560

Leu Lys Asp Met Ala Asp Ser Arg Arg Ile Asn Ala Asn Ile Arg Glu
                565                 570                 575

Glu Asp Glu Lys Arg Pro Ala Glu Glu Gln Pro Pro Phe Gly Val Tyr
            580                 585                 590

Ala Val Ile Leu Ser Ser Glu Phe Trp Pro Pro Phe Lys Asp Glu Lys
        595                 600                 605

Leu Glu Val Pro Glu Asp Ile Arg Ala Ala Leu Glu Ala Tyr Cys Lys
610                 615                 620

Lys Tyr Glu Gln Leu Lys Ala Met Arg Thr Leu Ser Trp Lys His Thr
625                 630                 635                 640

Leu Gly Leu Val Thr Met Asp Val Glu Leu Ala Asp Arg Thr Leu Ser
                645                 650                 655

Val Ala Val Thr Pro Val Gln Ala Val Ile Leu Leu Tyr Phe Gln Asp
            660                 665                 670

Gln Ala Ser Trp Thr Leu Glu Glu Leu Ser Lys Ala Val Lys Met Pro
        675                 680                 685

Val Ala Leu Leu Arg Arg Met Ser Val Trp Leu Gln Gln Gly Val
690                 695                 700

Leu Arg Glu Glu Pro Pro Gly Thr Phe Ser Val Ile Glu Glu Glu Arg
705                 710                 715                 720

Pro Gln Asp Arg Asp Asn Met Val Leu Ile Asp Ser Asp Asp Glu Ser
                725                 730                 735

Asp Ser Gly Met Ala Ser Gln Ala Asp Gln Lys Glu Glu Leu Leu
            740                 745                 750

Leu Phe Trp Thr Tyr Ile Gln Ala Met Leu Thr Asn Leu Glu Ser Leu
        755                 760                 765

Ser Leu Asp Arg Ile Tyr Asn Met Leu Arg Met Phe Val Val Thr Gly
770                 775                 780

Pro Ala Leu Ala Glu Ile Asp Leu Gln Glu Leu Gln Gly Tyr Leu Gln
785                 790                 795                 800

Lys Lys Val Arg Asp Gln Gln Leu Val Tyr Ser Ala Gly Val Tyr Arg
                805                 810                 815

Leu Pro Lys Asn Cys Ser
            820

<210> SEQ ID NO 13
<211> LENGTH: 76
<212> TYPE: PRT
<213> ORGANISM: Homo sapiens
<220> FEATURE:
<223> OTHER INFORMATION: human ubiquitin

<400> SEQUENCE: 13

```
Met Gln Ile Phe Val Lys Thr Leu Thr Gly Lys Thr Ile Thr Leu Glu
 1               5                  10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Gln Lys Glu
        50                  55                  60

Ser Thr Leu His Leu Val Leu Arg Leu Arg Gly Gly
 65                  70                  75
```

<210> SEQ ID NO 14
<211> LENGTH: 84
<212> TYPE: PRT
<213> ORGANISM: Artificial Sequence
<220> FEATURE:
<223> OTHER INFORMATION: Description of Artificial Sequence:
      FLAG-ubiquitin

<400> SEQUENCE: 14

```
Met Asp Tyr Lys Asp Asp Asp Asp Lys Gln Ile Phe Val Lys Thr Leu
 1               5                  10                  15

Thr Gly Lys Thr Ile Thr Leu Glu Val Glu Pro Ser Asp Thr Ile Glu
                20                  25                  30

Asn Val Lys Ala Lys Ile Gln Asp Lys Glu Gly Ile Pro Pro Asp Gln
            35                  40                  45

Gln Arg Leu Ile Phe Ala Gly Lys Gln Leu Glu Asp Gly Arg Thr Leu
        50                  55                  60

Ser Asp Tyr Asn Ile Gln Lys Glu Ser Thr Leu His Leu Val Leu Arg
 65                  70                  75                  80

Leu Arg Gly Gly
```

<210> SEQ ID NO 15
<211> LENGTH: 85
<212> TYPE: PRT
<213> ORGANISM: Artificial Sequence
<220> FEATURE:
<223> OTHER INFORMATION: Description of Artificial
     Sequence:FLAG-Cys-ubiquitin

<400> SEQUENCE: 15

```
Met Asp Tyr Lys Asp Asp Asp Lys Cys Gln Ile Phe Val Lys Thr
 1               5                  10                  15

Leu Thr Gly Lys Thr Ile Thr Leu Glu Val Glu Pro Ser Asp Thr Ile
                20                  25                  30

Glu Asn Val Lys Ala Lys Ile Gln Asp Lys Glu Gly Ile Pro Pro Asp
            35                  40                  45

Gln Gln Arg Leu Ile Phe Ala Gly Lys Gln Leu Glu Asp Gly Arg Thr
        50                  55                  60

Leu Ser Asp Tyr Asn Ile Gln Lys Glu Ser Thr Leu His Leu Val Leu
 65                  70                  75                  80

Arg Leu Arg Gly Gly
                85
```

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence:FLAG peptide

<400> SEQUENCE: 16

Asp Tyr Lys Asp Asp Asp Asp Lys
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence:FLAG-Cys

<400> SEQUENCE: 17

Asp Tyr Lys Asp Asp Asp Asp Lys Cys
1               5

<210> SEQ ID NO 18
<211> LENGTH: 86
<212> TYPE: PRT
<213> ORGANISM: Artificial Sequence
<220> FEATURE:
<223> OTHER INFORMATION: Description of Artificial
      Sequence:FLAG-Ala-Cys-ubiquitin

<400> SEQUENCE: 18

Met Asp Tyr Lys Asp Asp Asp Asp Lys Ala Cys Gln Ile Phe Val Lys
1               5                   10                  15

Thr Leu Thr Gly Lys Thr Ile Thr Leu Glu Val Glu Pro Ser Asp Thr
            20                  25                  30

Ile Glu Asn Val Lys Ala Lys Ile Gln Asp Lys Glu Gly Ile Pro Pro
        35                  40                  45

Asp Gln Gln Arg Leu Ile Phe Ala Gly Lys Gln Leu Glu Asp Gly Arg
    50                  55                  60

Thr Leu Ser Asp Tyr Asn Ile Gln Lys Glu Ser Thr Leu His Leu Val
65                  70                  75                  80

Leu Arg Leu Arg Gly Gly
                85

<210> SEQ ID NO 19
<211> LENGTH: 42
<212> TYPE: DNA
<213> ORGANISM: Artificial Sequence
<220> FEATURE:
<223> OTHER INFORMATION: Description of Artificial
      Sequence:FLAG-Cys-ubiquitin site-directed
      mutagenesis primer

<400> SEQUENCE: 19 cccccccaagc tttgcatgca gatttcgtg aagaccctga cc                42

<210> SEQ ID NO 20
<211> LENGTH: 45
<212> TYPE: DNA
<213> ORGANISM: Artificial Sequence
<220> FEATURE:
<223> OTHER INFORMATION: Description of Artificial
      Sequence:FLAG-Ala-Cys-ubiquitin site-directed
      mutagenesis primer

<400> SEQUENCE: 20 cccccccaagc ttgcgtgcat gcagattttc gtgaagaccc tgacc            45

<210> SEQ ID NO 21

```
<211> LENGTH: 6
<212> TYPE: PRT
<213> ORGANISM: Artificial Sequence
<220> FEATURE:
<223> OTHER INFORMATION: Description of Artificial Sequence:N-terminal
      His6-tag

<400> SEQUENCE: 21

His His His His His His
 1               5
```